(12) United States Patent
Barrall

(10) Patent No.: US 11,253,305 B2
(45) Date of Patent: Feb. 22, 2022

(54) SUPRAPECTINEAL QUADRILATERAL BONE PLATING SYSTEM AND METHODS OF MAKING AND USING SAME

(71) Applicant: DePuy Synthes Products, Inc., Raynham, MA (US)

(72) Inventor: Benjamin Barrall, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/843,206

(22) Filed: Apr. 8, 2020

(65) Prior Publication Data

US 2021/0315616 A1 Oct. 14, 2021

(51) Int. Cl.
*A61B 17/88* (2006.01)
*A61B 17/80* (2006.01)
*A61B 17/56* (2006.01)

(52) U.S. Cl.
CPC .......... *A61B 17/88* (2013.01); *A61B 17/8066* (2013.01); *A61B 2017/564* (2013.01)

(58) Field of Classification Search
CPC . A61B 17/80; A61B 17/8061; A61B 17/8066; A61B 17/88
See application file for complete search history.

(56) References Cited

U.S. PATENT DOCUMENTS

| | | | |
|---|---|---|---|
| 4,454,876 A | 6/1984 | Mears | |
| 4,573,458 A | 3/1986 | Lower | |
| 4,762,122 A | 8/1988 | Slocum | |
| 4,800,874 A | 1/1989 | Thomas et al. | |
| 4,815,455 A | 3/1989 | Kim | |
| 4,883,489 A | 11/1989 | Grundei et al. | |
| 4,919,672 A | 4/1990 | Millar et al. | |
| 5,108,397 A | 4/1992 | White | |
| D346,218 S | 4/1994 | White | |
| 5,326,367 A | 7/1994 | Robioneck | |
| 5,527,310 A | 6/1996 | Cole et al. | |
| 5,593,407 A | 1/1997 | Reis | |
| 6,004,353 A | 12/1999 | Masini | |
| 6,306,173 B1 | 10/2001 | Masini | |
| 6,340,362 B1 | 1/2002 | Pierer et al. | |
| 6,440,131 B1 | 8/2002 | Haidukewych | |
| 7,060,069 B2 | 6/2006 | Kozak et al. | |

(Continued)

FOREIGN PATENT DOCUMENTS

| WO | 2016086119 A1 | 6/2016 | |
|---|---|---|---|
| WO | 2016124132 A1 | 8/2016 | |
| WO | WO-2019169292 A1 * | 9/2019 | ......... A61B 17/8061 |

OTHER PUBLICATIONS

International Search Report, dated Jun. 21, 2021 in PCT/IB2021/052332, filed Mar. 19, 2021.

(Continued)

*Primary Examiner* — Larry E Waggle, Jr.
(74) *Attorney, Agent, or Firm* — Dunlap Codding, P.C.

(57) ABSTRACT

The presently disclosed and claimed inventive concept(s) relates generally to the field of bone plates for the reduction and fixation of bone fractures. In particular, the presently disclosed and claimed inventive concept(s) relates to a quadrilateral surface bone plate for the fixation of acetabular fractures having at least one securing port therein and methods of making and using same.

11 Claims, 78 Drawing Sheets

(56) References Cited

U.S. PATENT DOCUMENTS

| | | | |
|---|---|---|---|
| 7,850,732 B2 | 12/2010 | Heinz | |
| 7,857,836 B2 * | 12/2010 | Huebner | A61B 17/8033 606/280 |
| 7,905,883 B2 | 3/2011 | Bruecker et al. | |
| 8,177,785 B2 | 5/2012 | Vaidya | |
| 8,221,428 B2 | 7/2012 | Trieu | |
| 8,348,950 B2 | 1/2013 | Assell et al. | |
| 8,398,635 B2 | 3/2013 | Vaidya | |
| 8,398,637 B2 | 3/2013 | Parsell et al. | |
| 8,591,549 B2 | 11/2013 | Lange | |
| 8,603,091 B2 | 12/2013 | Lutz et al. | |
| 8,702,706 B2 | 4/2014 | Lanz | |
| 8,795,343 B2 | 8/2014 | Stucki et al. | |
| 8,814,866 B2 | 8/2014 | Vaidya | |
| 8,828,009 B2 | 9/2014 | Allen et al. | |
| 8,956,393 B2 | 2/2015 | Ramos Maza | |
| 9,017,407 B2 | 4/2015 | Donner | |
| 9,113,919 B2 | 8/2015 | Assell et al. | |
| 9,345,488 B2 | 5/2016 | Assell et al. | |
| 9,358,053 B2 * | 6/2016 | Guy | A61B 17/8066 |
| 9,439,659 B2 | 9/2016 | Schoenefeld et al. | |
| 9,498,268 B2 | 11/2016 | Ramos Maza | |
| 9,504,577 B2 | 11/2016 | Frederick et al. | |
| 9,713,485 B2 | 7/2017 | Guy et al. | |
| 9,744,045 B2 | 8/2017 | Link | |
| 10,028,737 B2 | 7/2018 | Stucki et al. | |
| 10,117,693 B2 | 11/2018 | Ehler et al. | |
| 10,251,687 B2 | 4/2019 | Guo | |
| 10,307,192 B2 | 6/2019 | Schlatterer | |
| 2005/0165401 A1 * | 7/2005 | Pack | A61B 17/8066 606/281 |
| 2013/0046389 A1 | 2/2013 | Fierlbeck et al. | |
| 2014/0180344 A1 | 6/2014 | Gonzalez-Hernandez | |
| 2014/0249586 A1 | 9/2014 | Guy et al. | |
| 2014/0257407 A1 | 9/2014 | Cai et al. | |
| 2014/0309690 A1 | 10/2014 | Stucki et al. | |
| 2015/0148851 A1 | 5/2015 | Ramos Maza | |
| 2015/0164519 A1 | 6/2015 | Cheng | |
| 2015/0320450 A1 | 11/2015 | Mootien et al. | |
| 2015/0320451 A1 | 11/2015 | Mootien et al. | |
| 2015/0374389 A1 | 12/2015 | Schoenefeld et al. | |
| 2016/0157897 A1 | 6/2016 | Vaidya | |
| 2016/0249963 A1 | 9/2016 | Guy et al. | |
| 2016/0317308 A1 | 11/2016 | Shea et al. | |
| 2016/0338714 A1 | 11/2016 | Schoenefeld et al. | |
| 2017/0086893 A1 | 3/2017 | Ming | |
| 2017/0100174 A1 | 4/2017 | Mishra et al. | |
| 2017/0128216 A1 | 5/2017 | Luck | |
| 2017/0181784 A1 | 6/2017 | Li | |
| 2017/0319249 A1 | 11/2017 | Guo | |
| 2018/0042622 A1 * | 2/2018 | Tang | A61B 17/8052 |
| 2018/0110551 A1 | 4/2018 | Schlatterer | |
| 2018/0263781 A1 | 9/2018 | Anderson et al. | |
| 2018/0296210 A1 | 10/2018 | Stucki et al. | |
| 2019/0029742 A1 | 1/2019 | Jarrett et al. | |
| 2019/0038420 A1 | 2/2019 | Link | |
| 2019/0151098 A1 | 5/2019 | Van Der Wal et al. | |
| 2019/0175793 A1 | 6/2019 | Koenig | |

OTHER PUBLICATIONS

Written Opinion of the International Searching Authority, dated Jul. 21, 2021 in PCT/IB2021/052332, filed Mar. 19, 2021.

* cited by examiner

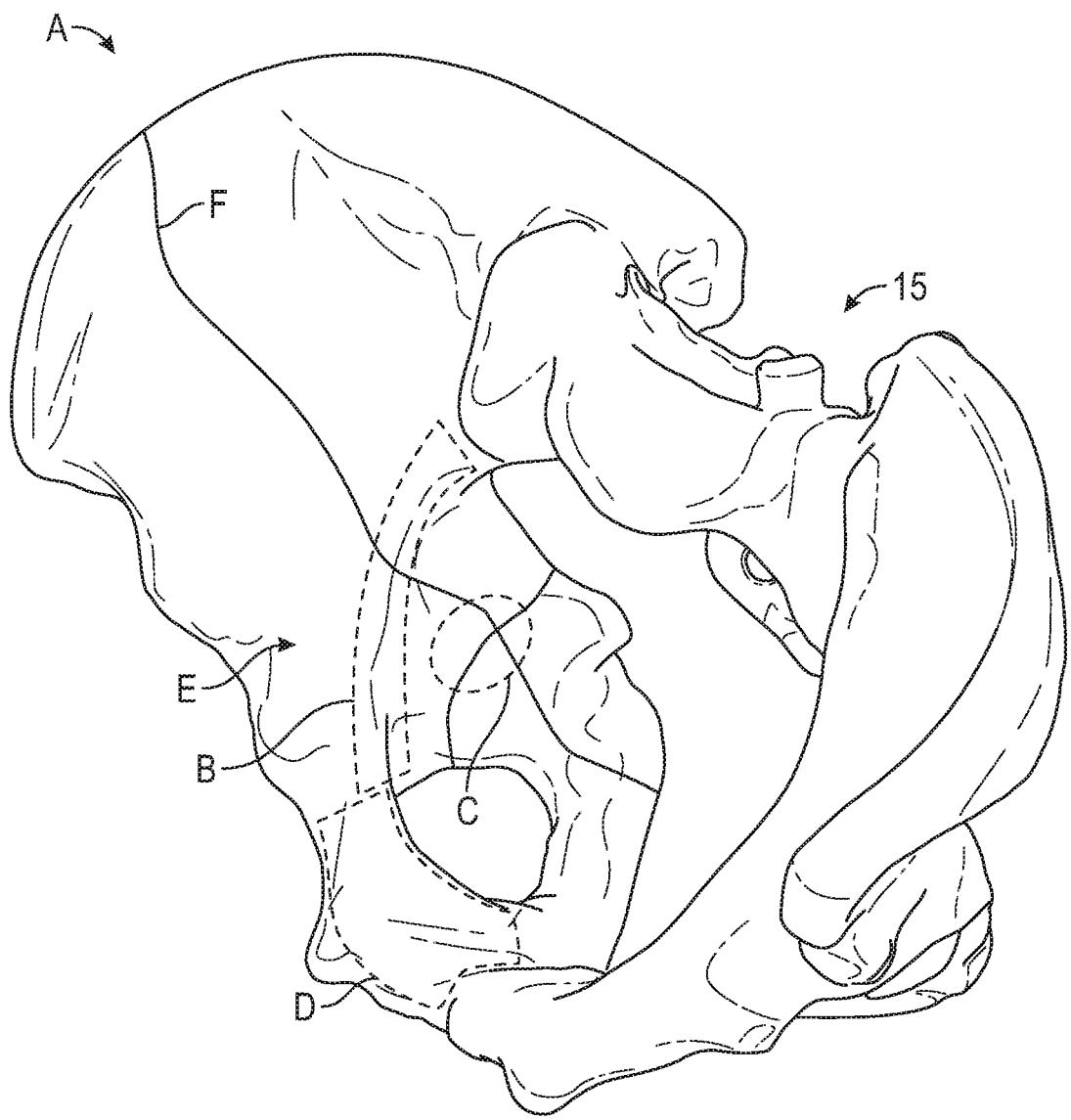
FIG. A

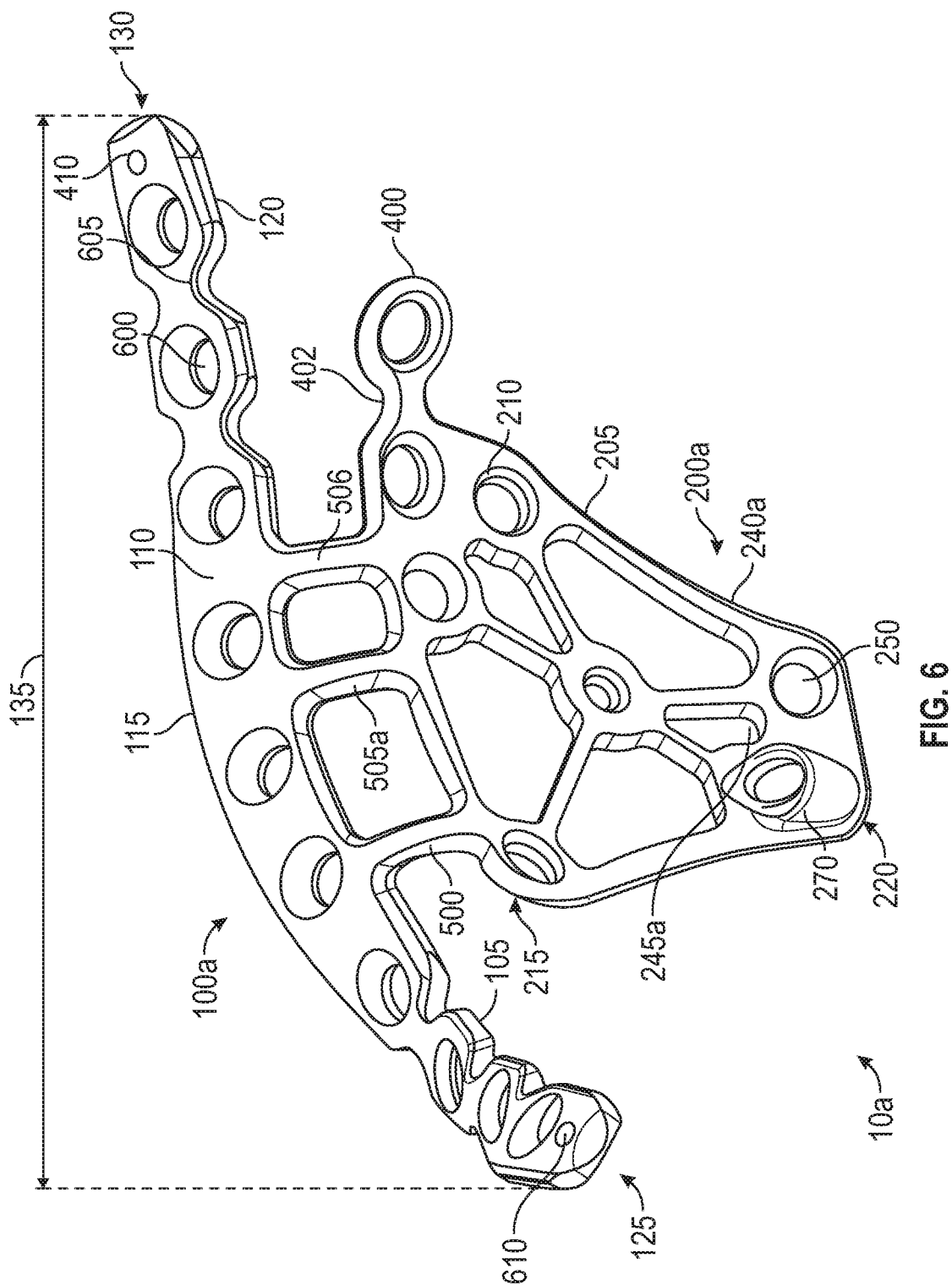

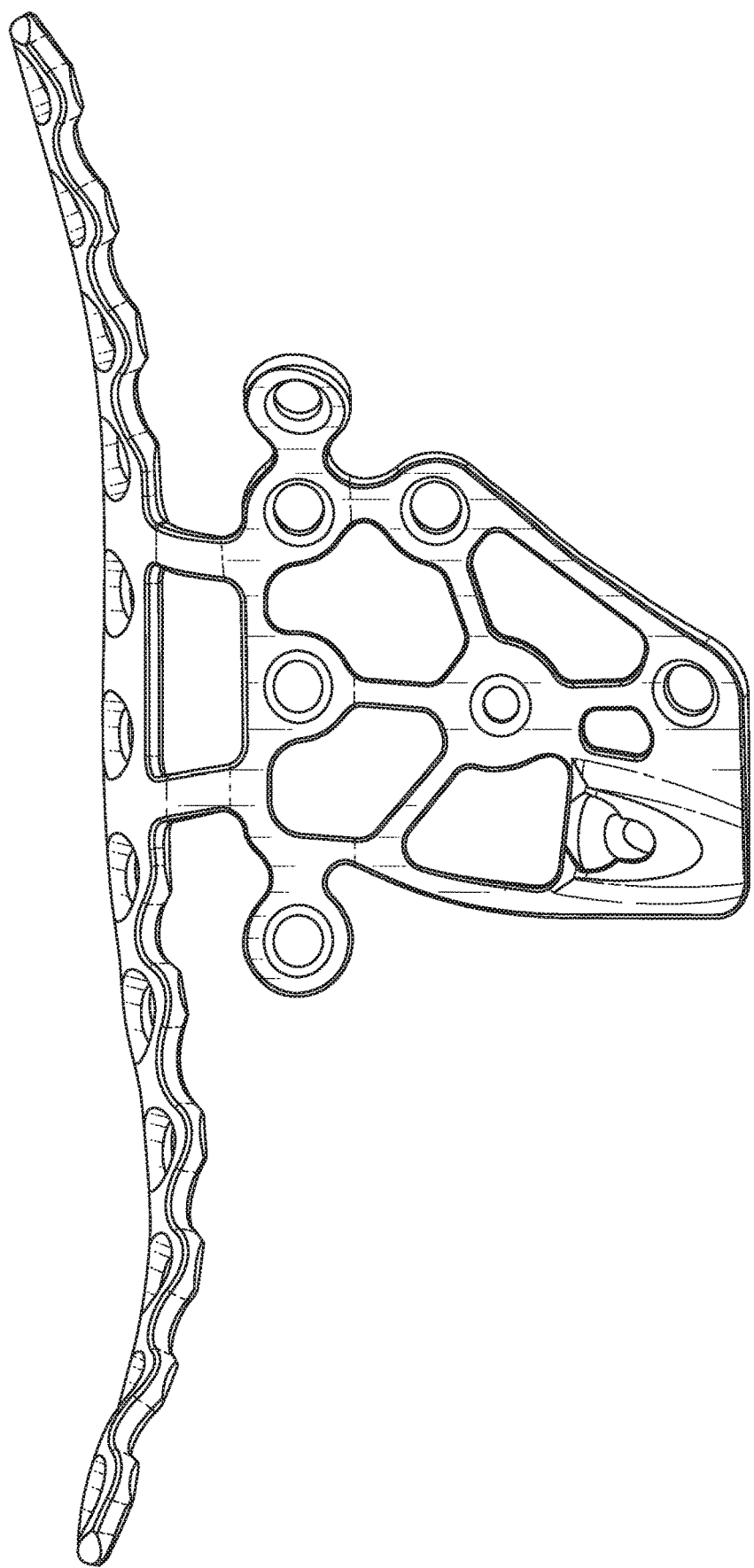

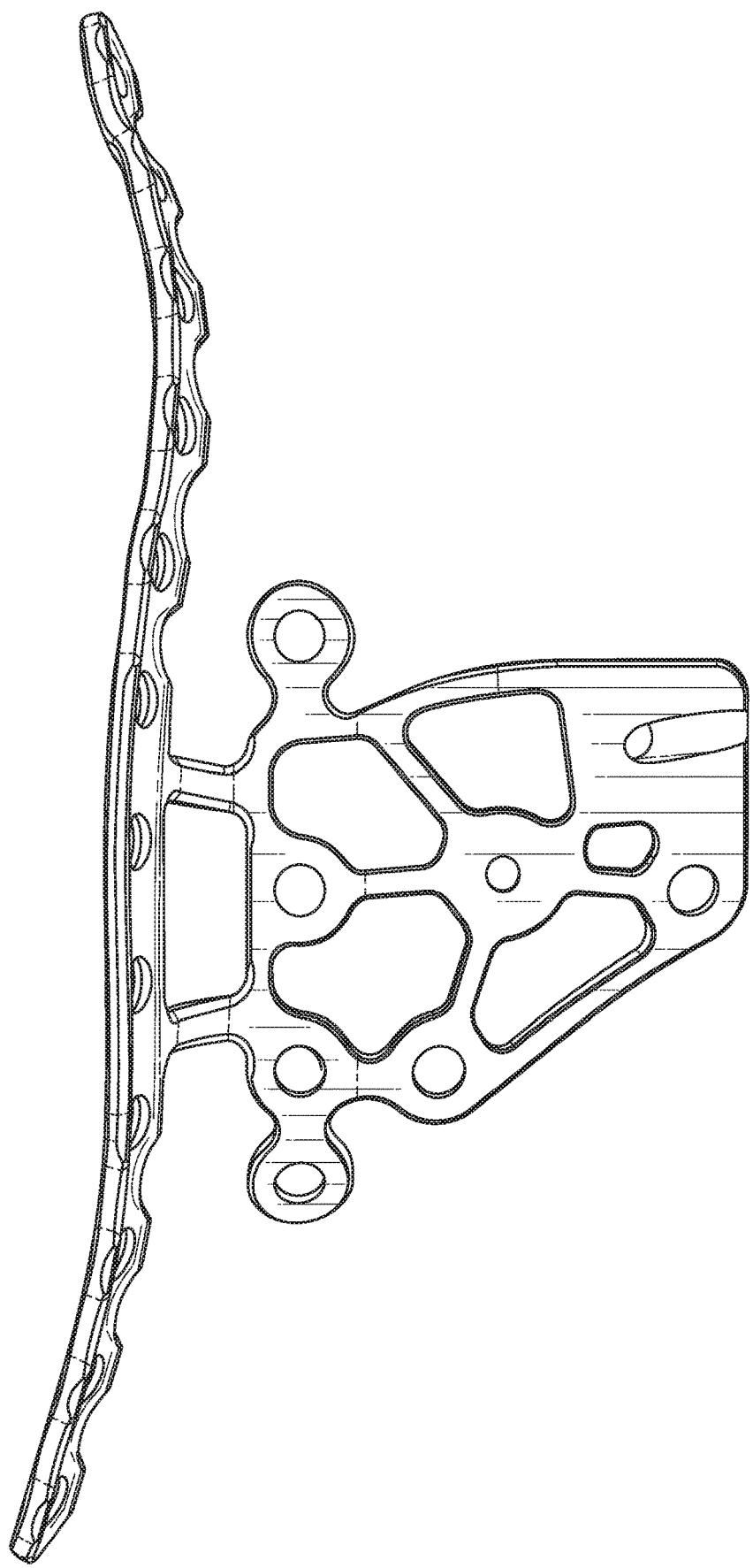

SUPRAPECTINEAL QUADRILATERAL BONE PLATING SYSTEM AND METHODS OF MAKING AND USING SAME

CROSS REFERENCE TO RELATED APPLICATIONS/INCORPORATION BY REFERENCE STATEMENT

Not Applicable.

STATEMENT REGARDING FEDERALLY SPONSORED RESEARCH OR DEVELOPMENT

Not Applicable.

BACKGROUND

1. Field of Invention

The presently disclosed and claimed inventive concept(s) relates generally to the field of bone plates for the reduction and fixation of bone fractures. In particular, the presently disclosed and claimed inventive concept(s) relates to a suprapectineal and quadrilateral surface bone plating system for the fixation of acetabular fractures having at least one securing port therein and methods of making and using same.

2. Description of Background Technology

A pelvis consists of an ilium, an ischium, and a pubis. A big and deep fossa located in the outer lateral side of the pelvis is called the acetabulum, and both the acetabulum and a caput femoris together make up a hip joint. The acetabulum and adjacent structures can be divided into two parts, namely, the anterior column and the posterior column. The anterior column consists of the anterior part of the ilium and the superior part of the pubis, which starts from the anterior superior iliac spine, and goes through a rami ossis pubis, and ends at the symphysis ossium pubis. The posterior column is generally thick and includes the vertical part of the ischium and the posterior part of the ilium connected with the ischium starting from the greater sciatic notch, through the center of the acetabulum, ending at the sciatic tuberosity.

The anterior column and the posterior column together form an upside-down "Y" shape (thereby "holding" the acetabulum), and their inner lateral sides meet at a quadrilateral area, thereby preventing the hip joint from moving inward. The iliac tuberosity at the outer side of the ilium narrows to a columnar area, where the acetabular dome is located and the bone mass thereafter thickens, generally. The anterior and posterior column meet at an angle-generally measured at or about 60 degrees—and form the shape of an arc (i.e., the acetabular dome) which is a weight-bearing area, supporting the articular surface of the hip joint.

Acetabulum fractures are mainly caused by high energy trauma. Currently, the commonly used fracture classification is Letournel-Judet, which divides the acetabulum fractures into 5 simple types and 5 complicated types with surgical treatment requiring anatomical reduction and rigid internal fixation in order to ensure successful restoration of function. Reduction and fixation of acetabulum fractures repair the concentric circles between the acetabulum and the hip joint, thereby allowing free and unimpaired movement of the hip and femur.

The fixation of acetabular fractures involving the quadrilateral area on the inner lateral sides of the acetabulum is complicated by the anatomical structures in line with known and currently used surgical approaches to the quadrilateral area. Such complications are mainly due to: (1) plate screws invading into the joint or vessels, nerves and organs around and within the pelvis, (2) incongruity between the surface of the plates and bones such that the fractures are not reduced resulting in the potential for uneven shear force and sliding displacement between the plate and bone, (3) failure of plates due to repeated bending thereby causing focal points of internal stress causing the plates to break, (4) mismatching of the contours of the plates and bone surfaces that cause the fracture site to loosen, displace, and the resulting non-union or malunion of the fractured bone, and (5) as the quadrilateral area of the acetabulum is adjacent to important anatomical structures (e.g., internal and external iliac arteries and veins, femoral arteries and veins, obturator nerves, obturator arteries and veins) as well as important organs (e.g., intestinal canals, uterus, and bladder), the likelihood of unintended injury during surgical repair is heightened.

In order to overcome some of these known challenges, those working in the field have developed bone plating systems for placement in the quadrilateral area. For example, U.S. Pat. No. 8,603,091. Additionally, others working in the field have developed bone plating systems comprising at least two plate structures attached to one another to form a "T" shape wherein a primarily horizontal portion conforms to the boney anatomical structure of the pelvic brim while a vertical portion extends from the horizontal portion into the quadrilateral area. See, for example, U.S. Patent Application Publication No. 2017/0181784. The horizontal and vertical portions have a plurality of holes for the placement of fixation screws that, when inserted through these holes and into the bone, bring the horizontal and vertical portions tight against the bone and, in some cases, reduce the fracture and position the broken bone fragments into alignment and in contact with one another. A disadvantage to these T shape plates is that the screw holes in the vertical portion are generally oriented 90 degrees to the surface of the vertical portion and allow limited variability of the angular approach of the bone screw to the surface of the bone. This limited angular variability is significant in the quadrilateral area as the insertion of a screw at an angle perpendicular to the surface of the vertical portion has a high rate of impingement of the acetabulum as well as other significant anatomical structures associated with the hip discussed hereinabove. Additionally, in order to insert a bone screw generally perpendicular to the quadrilateral surface and through such a vertical portion of a bone plate, the surgeon must work adroitly within the pelvis, avoiding injury to the important anatomical structures that lie within and about the pelvis and hip.

As such, it is known that the reduction and fixation of quadrilateral surface fractures are difficult and that current surgical systems, approaches, and methods can result in the impairment of the acetabulum. The center of the quadrilateral surface between the inner pelvis and the acetabulum is thin and must be buttressed in order to reduce the fracture and apply fixation-without misplacing a screw through this thin center portion and into significant anatomical structures within and surrounding the acetabulum. The known difficulties and disadvantages of existing quadrilateral fracture fixation systems are overcome by the presently disclosed and claimed inventive concept(s) relating generally to a suprapectineal and quadrilateral surface bone plating system for the fixation of acetabular fractures having at least one securing port therein and methods of making and using same.

BRIEF DESCRIPTION OF THE DRAWINGS

FIG. A is a three-dimensional view of an exemplary patient's pelvis indicating a fracture involving the acetabulum.

FIG. 6 is a perspective view of an additional alternative embodiment of a bone plating system of the present disclosure.

FIG. 16B is a front perspective view of the bone plating system of the present disclosure shown in FIG. 16A.

FIG. 16C is a rear perspective view of the bone plating system of the present disclosure shown in FIG. 16A.

DETAILED DESCRIPTION

Figure 1:
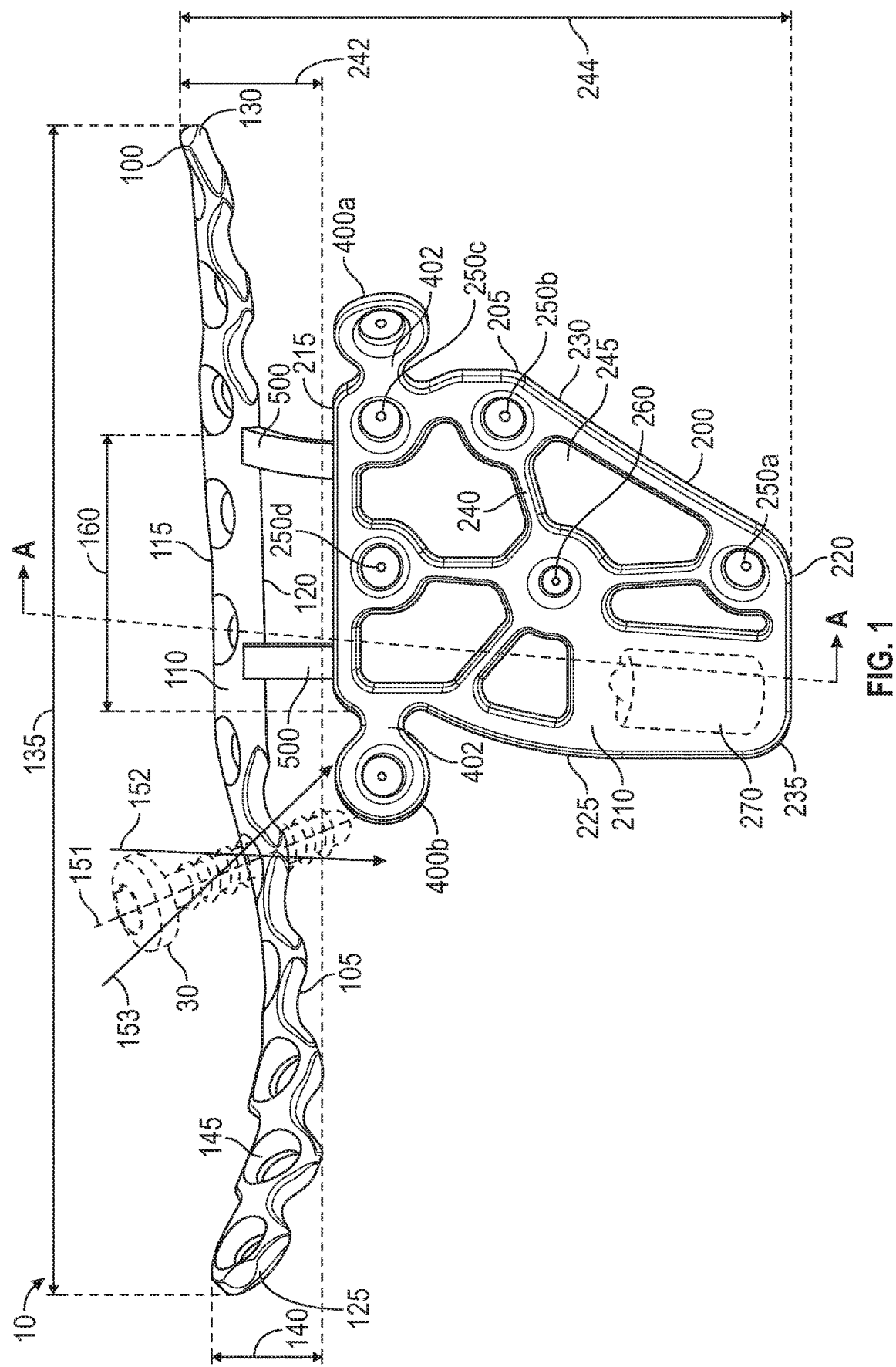
FIG. 1 is a front perspective view of a bone plating system of the present disclosure.

Before explaining at least one embodiment of the presently disclosed and claimed inventive concept(s) (hereinafter referred to as "the present disclosure") in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the medical procedures and techniques of, surgery, anesthesia, wound healing, orthopedic surgery, and infectious control described herein are those well-known and commonly used in the art. Standard techniques are used for orthopedic fracture reduction, fixation, and resolution of orthopedic trauma to the body.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, kits, and/or methods disclosed herein can be made and executed without undue experimentation in light of the present disclosure. While the articles, compositions, kits, and/or methods have been described in terms of particular embodiments, it will be apparent to those of skill in the art that variations may be applied to the articles, compositions, kits, and/or methods and in the steps or in the sequence of steps of the methods described herein without departing from the concept, spirit, and scope of the present disclosure. All such similar substitutes and modifications apparent to those skilled in the art are deemed to be within the spirit, scope, and concept of the present disclosure as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order of importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with" and "coupled to" or "connected with/to" include both direct association/coupling of two items to one another as well as indirect association/coupling of items moieties to one another. Non-limiting examples of associations/couplings include connections in which the connected parts are fixed to each other by atomic or molecular forces. These are non-detachable connections which can only be separated by destruction of the connection. Preferably, the connections are formed monolithically. As such, a bone plating system comprising differing portions formed from a single stamped metal plate would exhibit such properties. With respect to associations/couplings they may also have plastic deformation characteristics with an elasticity that can be pre-defined by dimensioning the cross-sections of the associations/couplings.

As used herein, the term "patient" or "subject" is meant to include all organisms, whether alive or dead, including any species having soft tissues and bones. For example, a method according to the inventive concepts disclosed herein may be used to fix an acetabular fracture within a living human, horse, cow, sheep, cat, dog, and the like.

Certain non-limiting embodiments of the present disclosure are directed to a bone plating system for a patient. The bone plating system includes a first bone plate sized and shaped to conform to a first bone portion of the patient, a second bone plate sized and shaped to conform to a second bone portion of the patient, wherein the second bone plate includes at least one securing port for receiving a fastener at an angle less than about 90 degrees with respect to a surface of the second bone plate, and at least one connecting bridge member configured to attach the first bone plate to the second bone plate. It is contemplated that the first bone plate may be a suprapectineal plate with the second bone plate being a quadrilateral plate. In such an embodiment, the bone plating system may also contain at least one connecting bridge member connecting the suprapectineal plate to the quadrilateral plate. It is further contemplated that the suprapectineal plate may be sized and shaped to conform to a pelvic brim of the patient and the quadrilateral plate is sized and shaped to a quadrilateral surface of the patient.

In certain non-limiting embodiments, the first bone plate has a first edge, a second edge, a first end, and a second end with a width extending generally between the first edge and the second edge, and a length extending between the first end and the second end, with the length being greater than the width. The first end and second end of the first bone plate may be generally rounded having a convex shaped extending generally from a first bone engaging surface to a first tissue engaging surface of the first bone plate. The length of the first bone plate is generally linear. It is contemplated that the length of the first bone plate may have one or more curves or twists that conform the first bone plate to the anatomy of the patient.

In certain non-limiting embodiments, the first bone plate further includes a plurality of screw apertures. The plurality of screw apertures may further include a screw head support surface and a screw shaft clearance surface, with the screw head support surface defining a screw head receiving volume and the screw shaft clearance surface defining a screw shaft receiving volume. The first bone plate may also include a plurality of forming bridges adjacent and between the plurality of screw apertures and the plurality of forming bridges may be plastically deformable thereby providing the first bone plate with a secondary configuration. It is contemplated that the secondary configuration of the first bone plate matches an anatomy of the patient.

In certain non-limiting embodiments, the second bone plate may be generally trapezoid shaped and further includes a distal end, a proximal end, a first side, and a second side wherein the distal end and proximal are generally parallel to one another and the first side and the second side generally diverge from one another. It is contemplated that the second bone plate may include a plurality of secondary screw apertures. The plurality of secondary screw apertures may further include a screw head support surface and a screw shaft clearance surface, with the screw head support surface defining a screw head receiving volume and the screw shaft clearance surface defining a screw shaft receiving volume. It is contemplated that the second bone plate may include a plurality of internal struts defining a plurality of through-holes extending from a second bone engaging surface to a second tissue engaging surface of the second bone plate. It is further contemplated that the second bone plate may include at least one reduction engaging aperture for receiving a surgical instrument capable of applying a force to the second bone plate.

In certain non-limiting embodiments, the at least one securing port includes a bore extending from a second tissue engaging surface of the second bone plate to a second bone engaging surface of the second bone plate, the bore extending in a direction substantially oriented toward a distal end of the second bone plate and away from a proximal end of the second bone plate. The bore may further include a bore central axis extending through a center of the bore in a direction substantially oriented toward the distal end of the second bone plate and away from the proximal end of the second bone plate. The at least one securing port may further include a wall surrounding the bore, wherein the wall defines (i) a fastener support surface defining a head receiving volume adjacent the second tissue engaging surface, and (ii) a shaft clearance surface defining a generally frustoconical shaped shaft receiving volume, whereby the head receiving volume is generally spherically shaped and the shaft clearance surface is generally ellipse shaped. It is contemplated that the fastener support surface is adjacent and abuts the shaft clearance surface at a bore vertex extending generally the entire circumference of the bore.

In certain non-limiting embodiments, the at least one securing port may further include a fastener support axis generally adjacent the bore vertex, wherein the fastener support axis extends at a first angle that is less than or equal to 90 degrees relative to a bone engaging axis of the second bone plate. It is contemplated that the first angle may be from about 1 to about 15 degrees, from about 15 to about 35 degrees, from about 35 to about 60 degrees, from about 60 to about 75 degrees, and from about 75 to about 90 degrees.

Certain further non-limiting embodiments of the present disclosure are directed to a bone plating system for a patient having (a) a substantially rectangular shaped first bone plate sized and shaped to conform to a first bone portion of the patient, the first bone plate having a first bone engaging surface, a first tissue engaging surface, a first edge, and a second edge; (b) a substantially trapezoidal shaped second bone plate sized and shaped to conform to a second bone portion of the patient, the second bone plate having a second bone engaging surface, a second tissue engaging surface, a proximal end, a distal end, and an outer peripheral edge; and (c) at least one connecting bridge member having a first end and a second end, wherein the first end of the at least one connecting bridge member is connected to the second edge of the first bone plate and the second end of the at least one connecting bridge member is connected to the proximal end of the second bone plate.

In certain non-limiting embodiments, the proximal end of the second bone plate is spaced a first distance away from the second edge of the first bone plate, and the distal end of the second bone plate is spaced a second distance away from the second edge of the first bone plate, with the second distance being larger than the first distance. The second bone engaging surface of the second bone plate may have a bone engaging axis extending from the proximal end of the second bone plate to the distal end of the second bone plate, the bone engaging axis being a straight line fit to a series of data points representing the second bone engaging surface of the second bone plate. Further, the second bone plate may have at least one securing port for receiving a fastener, the at least one securing port having a bore extending from the second tissue engaging surface to the second bone engaging surface in a direction substantially oriented toward the outer peripheral edge and away from an interior portion of the second bone plate.

In certain non-limiting embodiments, the at least one securing port may have a wall surrounding the bore, the wall having a fastener support surface defining a head receiving volume of the bore adjacent to the second tissue engaging surface, and a shaft clearance surface defining a substantially frustoconical shaped shaft receiving volume of the bore adjacent to the second bone engaging surface. It is contemplated that the fastener support surface is adjacent to the shaft clearance surface such that the fastener support surface and the shaft clearance surface have a common vertex extending around at least a portion of the bore, the fastener support surface having a fastener support axis adjacent to the common vertex, the fastener support axis extending at an angle less than or equal to 90 degrees relative to the bone engaging axis. It is further contemplated, that when the first bone plate is positioned on the first bone portion, the second bone plate is positioned on the second bone portion, and a shaft of a fastener is disposed through the bore and into the second bone portion, a head of the fastener engages the fastener support surface and applies a first force vector to the second bone plate thereby drawing the second bone engaging surface against the second bone portion of the patient's bone. It is also contemplated that the bone plating system includes at least one secondary surgery instrument for implanting the bone plating system in the patient in another non-limiting embodiment.

Certain non-limiting embodiments of the present disclosure are further directed to a method of implanting a bone plating system into a patient. It is contemplated that the method includes the step of surgically accessing a pelvic cavity of the patient and implanting a bone plating system in the patient. The bone plating system in certain embodiments includes: (a) a substantially rectangular shaped first bone plate sized and shaped to conform to a first bone portion of the patient, the first bone plate having a first bone engaging surface, a first tissue engaging surface, a first edge, and a second edge; (b) a substantially trapezoidal shaped second bone plate sized and shaped to conform to a second bone portion of the patient, the second bone plate having a second bone engaging surface, a second tissue engaging surface, a proximal end, a distal end, and an outer peripheral edge; and (c) at least one connecting bridge member having a first end and a second end, wherein the first end of the at least one connecting bridge member is connected to the second edge of the first bone plate and the second end of the at least one connecting bridge member is connected to the proximal end of the second bone plate.

In certain non-limiting embodiments of the method, the proximal end of the second bone plate is spaced a first distance away from the second edge of the first bone plate, and the distal end of the second bone plate is spaced a second distance away from the second edge of the first bone plate, with the second distance being larger than the first distance. The second bone engaging surface of the second bone plate may have a bone engaging axis extending from the proximal end of the second bone plate to the distal end of the second bone plate, the bone engaging axis being a straight line fit to a series of data points representing the second bone engaging surface of the second bone plate. Further, the second bone plate may have at least one securing port for receiving a fastener, the at least one securing port having a bore extending from the second tissue engaging surface to the second bone engaging surface in a direction substantially oriented toward the outer peripheral edge and away from an interior portion of the second bone plate.

In further certain non-limiting embodiments of the method, the at least one securing port may have a wall surrounding the bore, the wall having a fastener support surface defining a head receiving volume of the bore adjacent to the second tissue engaging surface, and a shaft clearance surface defining a substantially frustoconical shaped shaft receiving volume of the bore adjacent to the second bone engaging surface. It is contemplated that the fastener support surface is adjacent to the shaft clearance surface such that the fastener support surface and the shaft clearance surface have a common vertex extending around at least a portion of the bore, the fastener support surface having a fastener support axis adjacent to the common vertex, the fastener support axis extending at an angle less than or equal to 90 degrees relative to the bone engaging axis. It is further contemplated, that when the first bone plate is positioned on the first bone portion, the second bone plate is positioned on the second bone portion, and a shaft of a fastener is disposed through the bore and into the second bone portion, a head of the fastener engages the fastener support surface and applies a first force vector to the second bone plate thereby drawing the second bone engaging surface against the second bone portion of the patient's bone.

Turning now to the drawings, FIG. A is a three-dimensional view of an exemplary human pelvis A from a perspective looking inclined downwards from the left side of the pelvis to the right side of the pelvis. In FIG. A, a pelvic brim is roughly framed with a dashed line and indicated with reference letter B, a quadrilateral surface is roughly encircled with a dashed line and indicated with reference letter C, a posterior column is roughly framed with a dashed line and indicated with reference letter D, and an acetabulum is indicated with reference letter E. Further, an exemplary fracture F is shown, which runs across the pelvis A and passes through the quadrilateral surface C. As one of ordinary skill in the art would appreciate, the fracture F is only one example of such a fracture that can occur, and other fractures are likely in which the quadrilateral surface C is comminuted such as those types of fractures outlined by Letournel-Judet mentioned hereinabove.

Figure 1A:
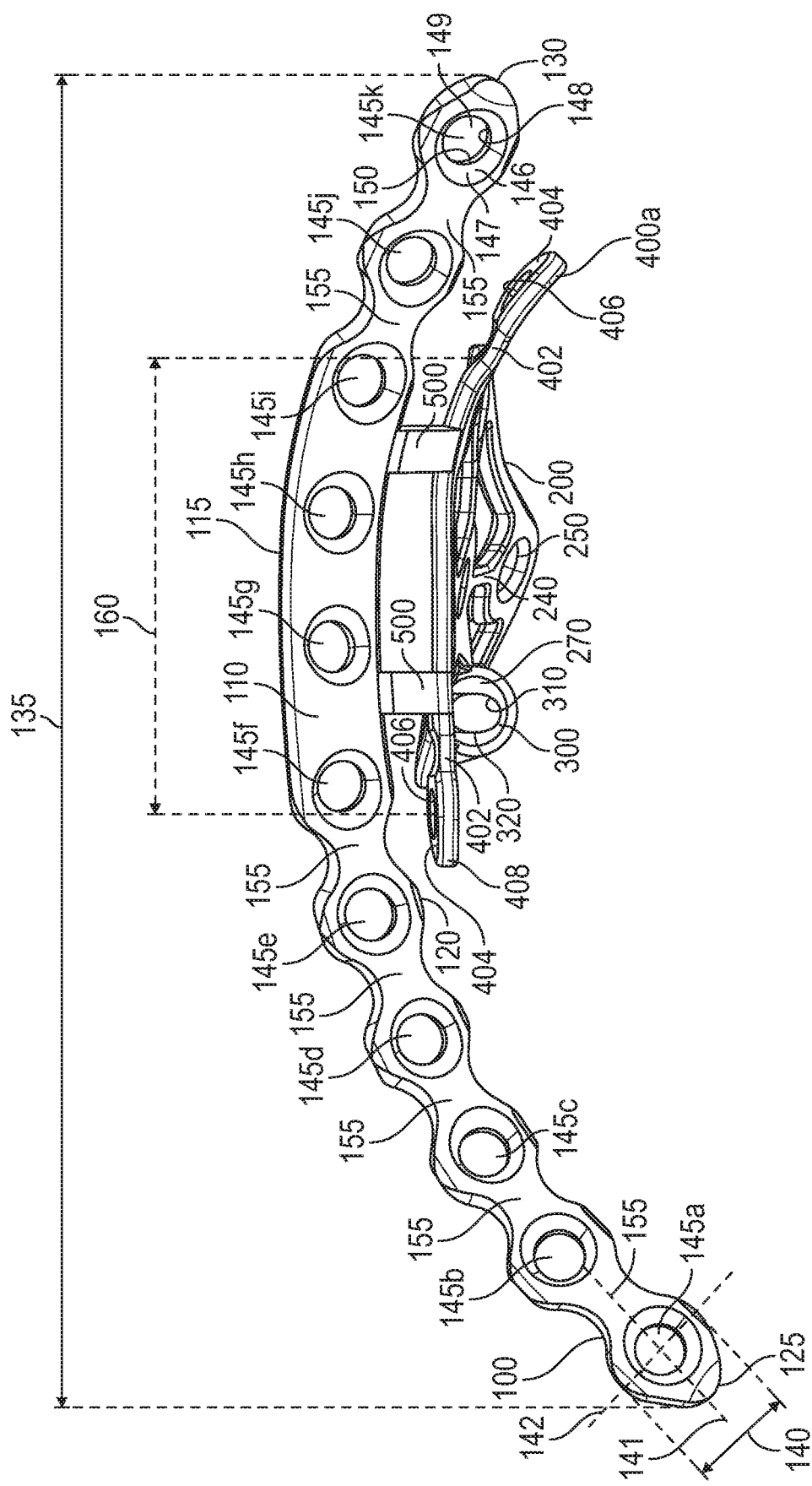
FIG. 1A is a top perspective view of the bone plating system of the present disclosure as shown in FIG. 1.
Figure 1B:
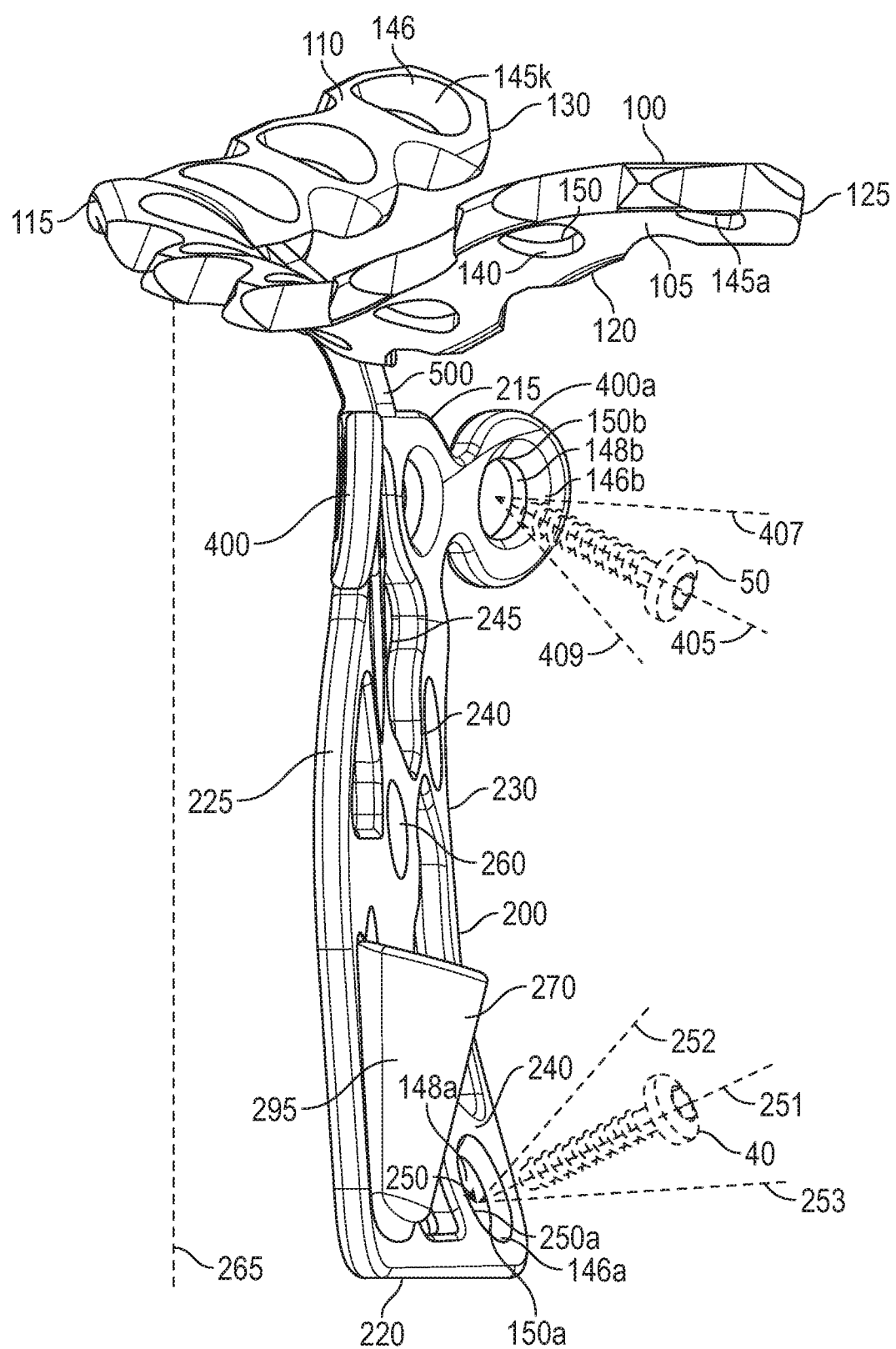
FIG. 1B is a side perspective view of the bone plating system of the present disclosure as shown in FIG. 1.
Figure 1C:
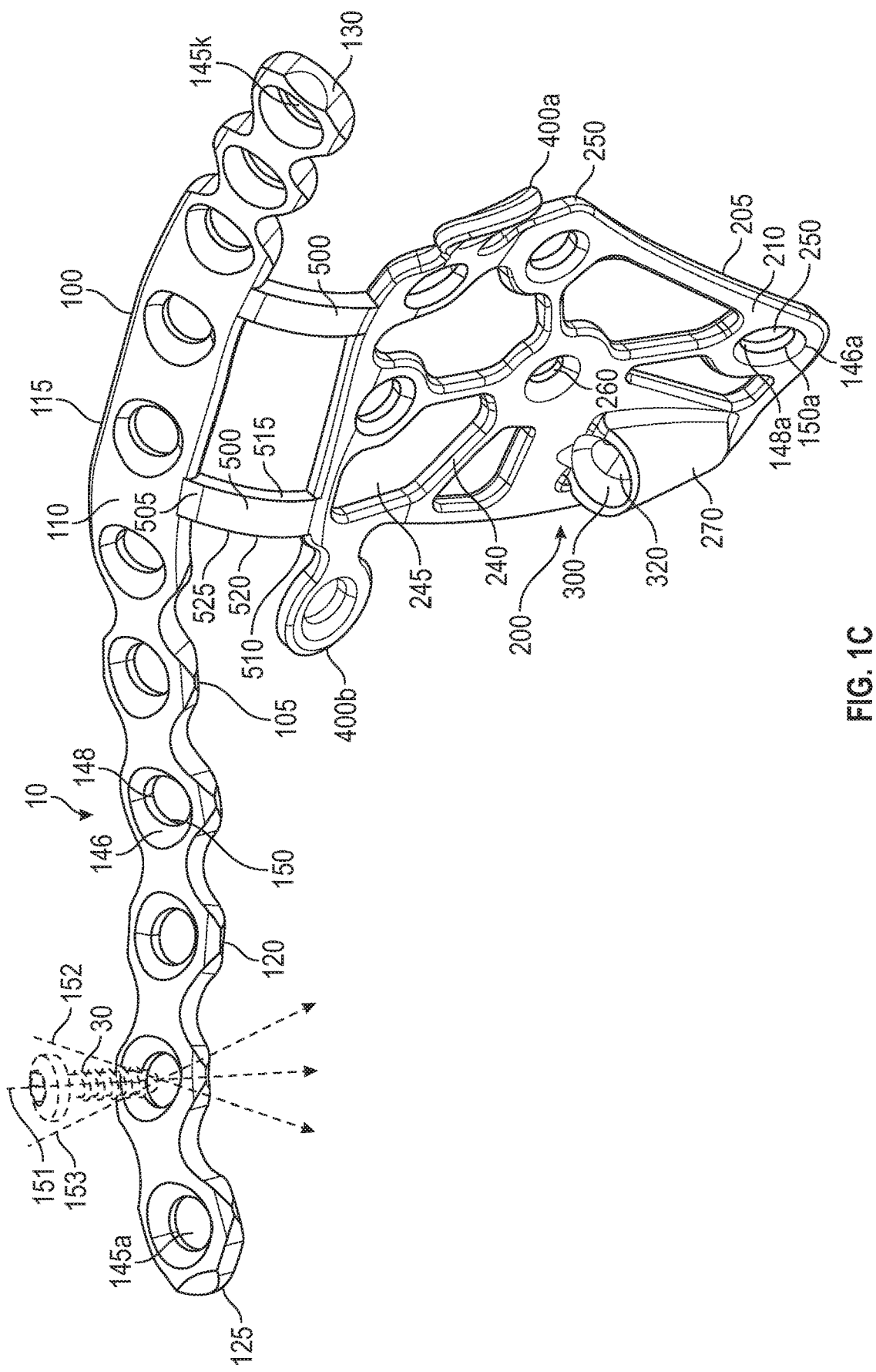
FIG. 1C is a perspective view of the bone plating system of the present disclosure as shown in FIG. 1.
Figure 1D:
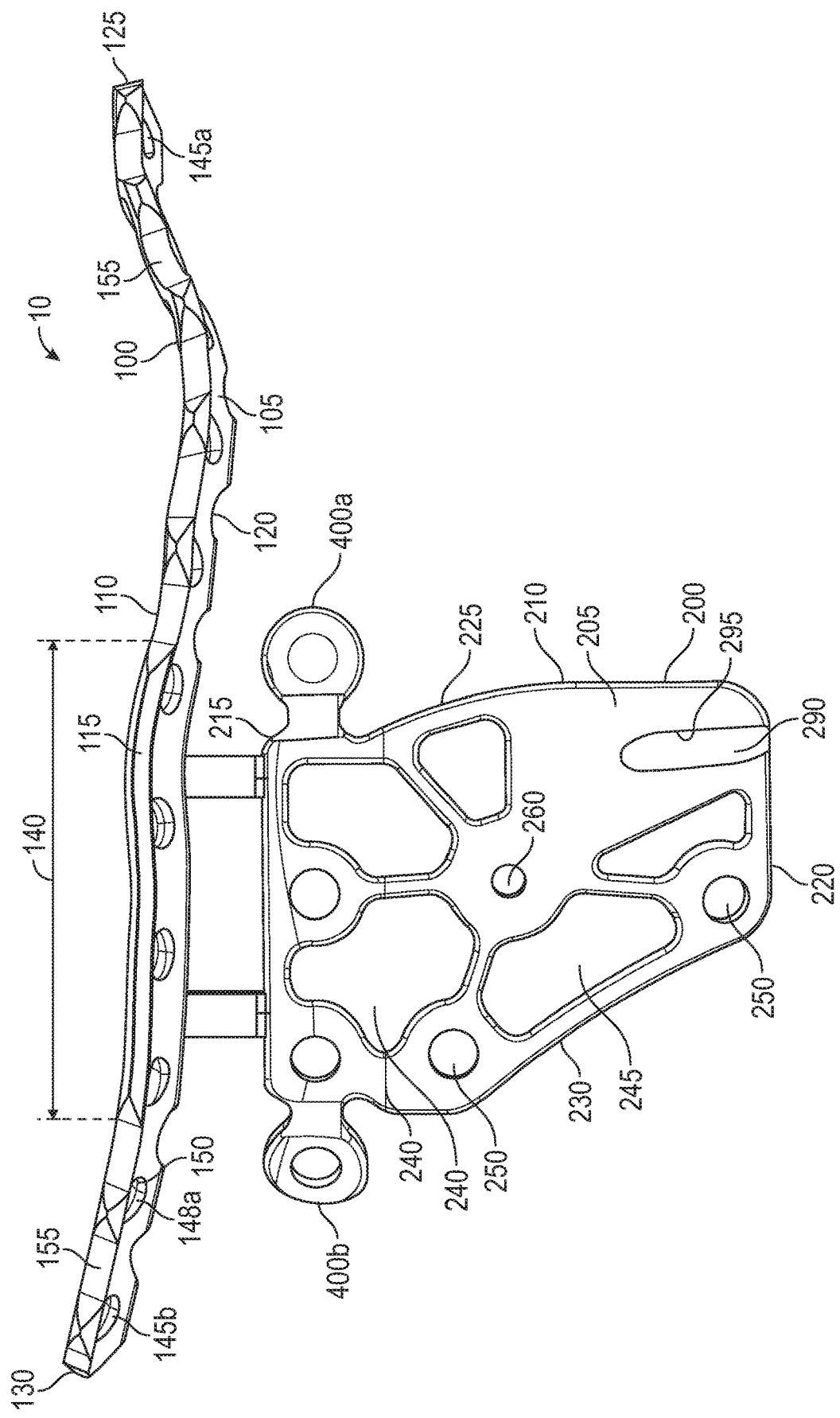
FIG. 1D is a rear-perspective view of the bone plating system of the present disclosure as shown in FIG. 1.

With regard to FIGS. 1-1D, shown therein is a bone plating system 10 constructed in accordance with the present disclosure. The bone plating system 10 includes a first bone plate 100, sometimes known in the art generally as a suprapectineal plate, a second bone plate 200, sometimes known in the art generally as a quadrilateral plate, and at least one connecting bridge member 500 (with two connecting bridge members 500 shown in FIG. 1). The first bone plate 100 is connected to the second bone plate 200 generally via the at least one connecting bridge member 500 to form generally a T-shape. The bone plating system 10 can be used in repairing fractures of the acetabulum E and, more particularly, in repairing fractures running through at least a portion of the quadrilateral surface C (FIG. A). Additionally, the bone plating system 10 can be used to repair fractures of the acetabulum E that include fractures having an anterior column D component in addition to a fracture of the quadrilateral surface C.

Figure 3:
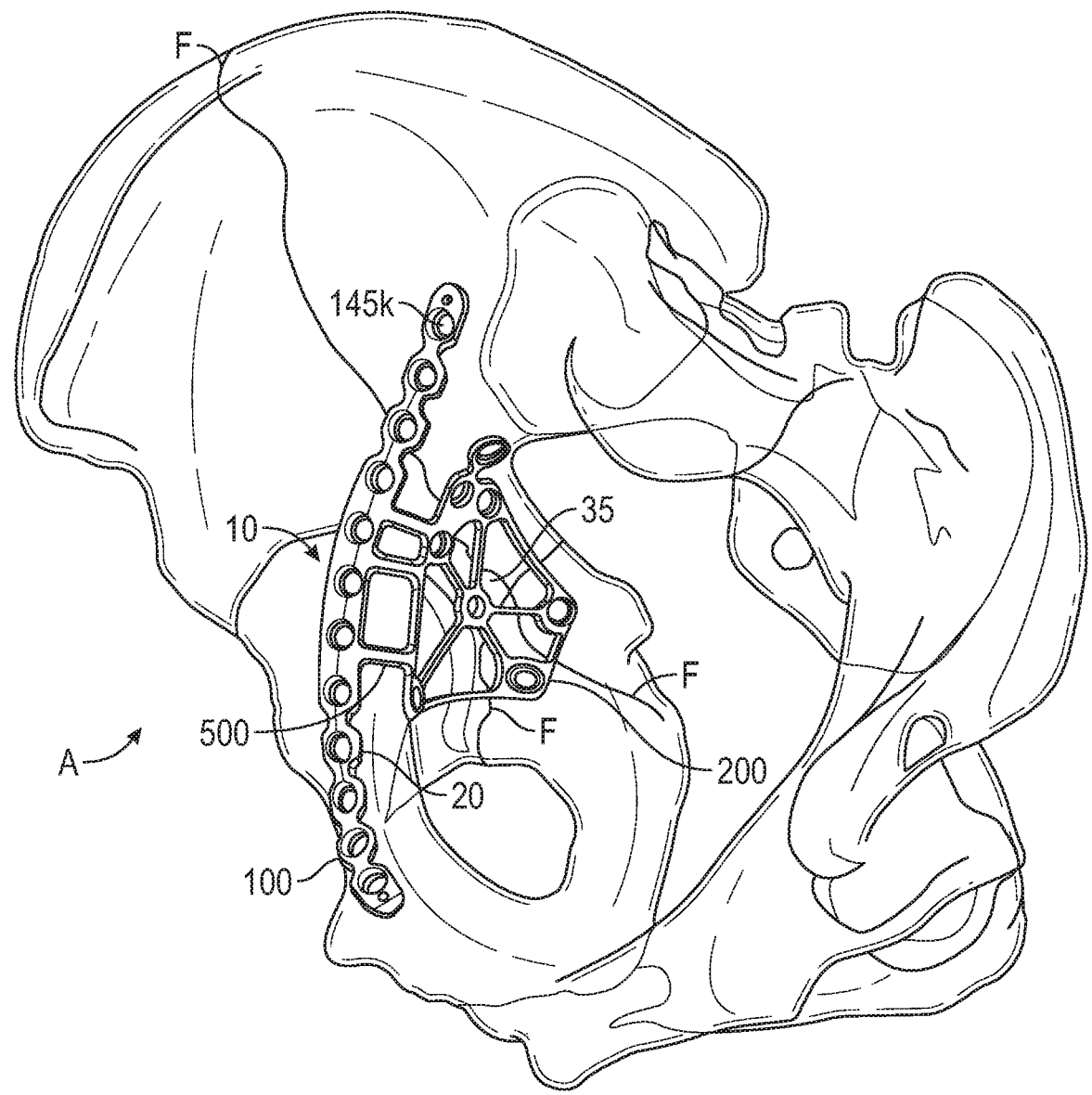
FIG. 3 is a three-dimensional view of the bone plating system of the present disclosure as shown in FIG. 1 intraoperatively placed within a patient's pelvis.
Figure 4:
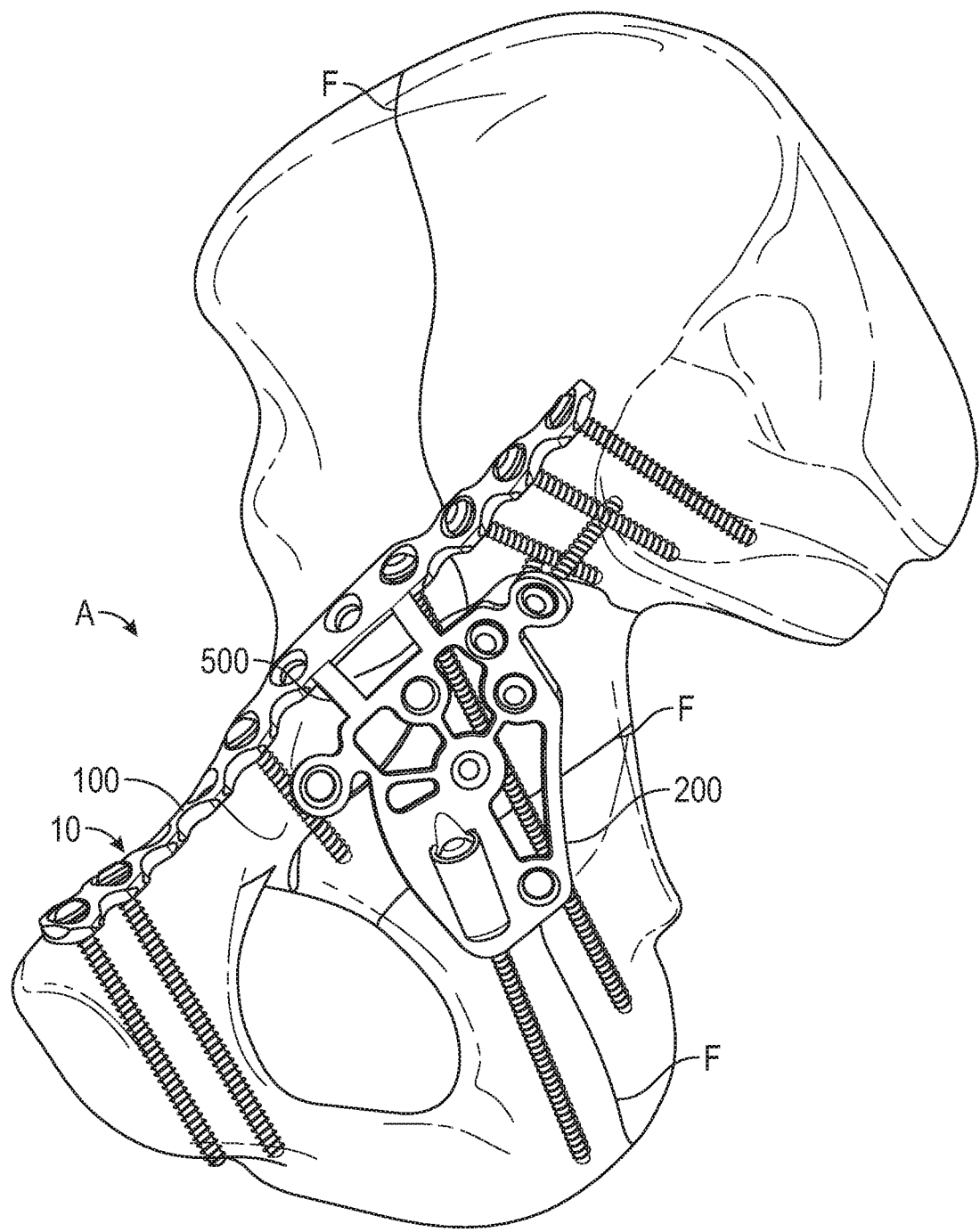
FIG. 4 is a three-dimensional view of the bone plating system of the present disclosure as shown in FIG. 1 intraoperatively placed within a patient's pelvis and showing the insertion of a plurality bone screws in combination with the bone plating system.

FIGS. 3 and 4, described in further detail hereinafter, show the bone plating system 10 according to the embodiment of the present disclosure according to FIG. 1 being located at the implanting position within the human pelvis A of a patient 15. The bone plating system 10 may come in one or more sizes and shapes, differentiated to account for morphological differences between subpopulations of patients (e.g. for male and female anatomy), and may be supplied in kit form with one or more additional surgical tools.

The first bone plate 100 is generally elongated and rectangular in shape and is sized and shaped to conform to a first bone portion 20 (generally, along the pelvic brim B) of the pelvis A of the patient 15 (as shown in FIGS. A, 3, and 4). As can be ascertained from the figures, the first bone plate 100 while being generally rectangular in shape itself may overall take on a configuration generally resembling the letters J or C when shaped and sized to fit a specific patient's anatomy and/or when supplied to the surgeon in a pre-arranged shape. The first bone plate 100 includes a first bone engaging surface 105, a first tissue engaging surface 110, a first edge 115, a second edge 120, a first end 125, and a second end 130. The first bone plate 100 has a length 135 extending from the first end 125 to the second end 130, and a width 140 extending from the first edge 115 to the second edge 120. The length 135 is greater than the width 140. The first end 125 and the second end 130 are generally rounded in shape and are shown as having a blunt nose configuration in FIGS. 1 through 1D—i.e., the first end 125 and the second end 130 are defined by a generally convex shape extending from the first bone engaging surface 105 to the first tissue engaging surface 110. Additionally, the first end 125 and the second end 130 can be shaped in any configuration (for example, but not by way of limitation, a "knife-edge," a squared edge, and a rounded edge) and the shape of first end 125 may be different from that of second end 130. One of ordinary skill in the art would appreciate, however, that the first bone plate 100 can be sized and shaped in various configurations to conform to the first bone portion 20 of the patient. For example, but not by way of limitation, the first bone plate 100 can be shaped with curves and twists along its length 135 as shown in detail in FIG. 1 and in particular detail in FIGS. 1A and 1B—i.e., generally in the shape of the letters J or C as described hereinabove or in a more circular or serpentine configuration.

The first bone plate 100 has a plurality of screw apertures 145 (as shown in detail as having eleven such screw apertures 145 in FIG. 1-1D) for accepting bone screws, such as screw 30 (FIGS. 1 and 1C), extending from the first tissue engaging surface 110 to the first bone engaging surface 105. The plurality of screw apertures 145 are provided along the length 135 of the first bone plate 100 in substantially equal intervals. Spaced between at least a portion of the plurality of screw apertures 145, along the length 135 of the first bone plate 100, are a series of forming bridges 155 that are deformable in three axes and have sufficient memory such that a surgeon or other medical practitioner can bend and twist the first bone plate 100 into a new configuration that conforms to the first bone portion 20 of the patient without deforming or otherwise encroaching upon the structural integrity and configuration of the plurality of screw apertures 145 themselves and/or the first bone plate 100.

The deformation of the forming bridges 155 is preferably performed solely by hand force without further measures, such as heating of the material before bending, or the like. More preferably, the forming bridges 155 can also be constructed such that bending tools (not shown) are required and/or preferable for use in deforming the first bone plate 100 and are either separately provided or paired or included as part of a kit containing the bone plating system 10. In another embodiment, the material comprising the bone plating system 10 generally, and the forming bridges 155 more specifically, can be formed from a material that requires heating in order to be deformable. It is contemplated that the bone plating system 10—including the first bone plate 100, the second bone plate 200, and the connecting bridge members 500—is provided alone or as part of a kit in an appropriately pre-bent shape from the manufacturer. In such a pre-bent configuration, the bone plating system 10 may or may not include deformable components that the surgeon or other medical practitioner can shape to fit the specific patient anatomy.

Each of the plurality of screw apertures 145 include a screw head support surface 146 defining a screw head receiving volume 147 (shown with perspective in respect to screw aperture 145*k* in FIG. 1A) adjacent the first tissue engaging surface 110, and a screw shaft clearance surface 148 defining a screw shaft receiving volume 149 adjacent the first bone engaging surface 105. The screw shaft clearance surface 148 has a diameter less than a spherical diameter of the screw head support surface 146—for example, an exemplary spherical diameter of the screw head support surface 146 is from about 6 to about 9 mm, while an exemplary diameter of the screw shaft clearance surface 148 is from about 3 to about 5.5 mm. A vertex 150 exists within each of the plurality of screw apertures 145 where the screw shaft clearance surface 148 meets the screw head support surface 146. As such, each screw aperture 145 is formed as a countersunk hole. This "countersunk hole" configuration of the screw aperture 145 is such that the screw head support surface 146 is provided with a curved fillet in one embodiment or a conical chamfer in an alternative embodiment. In such a "countersunk hole" configuration of the screw aperture 145, a head of the screw 30 is generally seated within the screw head receiving volume 147 and does not interact or engage substantially with tissue that may come into contact with the first tissue engaging surface 110 of the first bone plate 100.

Each of the plurality of screw apertures 145 have a central axis 151 running through a center of the screw head receiving volume 147 and the screw shaft receiving volume 149 from the first tissue engaging surface 110 to the first bone engaging surface 105—i.e., the central axis 151 of each of the screw apertures 145 is positioned substantially at a point where a longitudinal centerline 141 of the first bone plate 100 intersects with a latitudinal centerline 142 running through each of the screw apertures 145 from the first edge 115 to the second edge 120 of the first bone plate 100.

As shown in FIG. 1, the central axis 151 is oriented generally at a 90-degree angle with respect to at least one of the first bone engaging surface 105 and the first tissue engaging surface 110 of the first bone plate 100. Alternatively, the central axis 151 may be oriented at an angle of from about 45-degrees to about 90-degrees with respect to at least one of the first bone engaging surface 105 and the first tissue engaging surface 110 of the first bone plate 100 as depicted in the embodiment of FIG. 5. In use, a bone fastener such as the screw 30 (FIGS. 1 and 1C) is inserted through the screw aperture 145 along the central axis 151—in a direction from the first tissue engaging surface 110 to the first bone engaging surface 105—and into at least a portion of the first bone portion 20 of the patient. In alternate embodiments, which will be appreciated by those of ordinary skill in the art given the present disclosure, the screw 30 can be inserted through the screw aperture 145 at an angle less than or greater than that of the central axis 151. For example, but not by way of limitation, the screw 30 can be inserted through the screw aperture 145 at an angle deviating from the central axis 151 from about 1 degree to about 40 degrees. As such, the angle at which the screw 30 can be inserted through the screw aperture 145 can be +/−40 degrees from the central axis 151 as indicated by insertion vectors 152, 153. In preferred embodiments, the angle from which the screw 30 can deviate from the central axis 151 while being inserted through the screw apertures 145 is from about 1 to about 10 degrees; more preferably from about 10 to about 20 degrees; and more preferably from about 20 to about 40 degrees. The screw 30 may be of any width, size, or length and is generally chosen by the surgeon according to the thickness and physical characteristics of the bone into which the screw 30 is inserted. It is unnecessary for all of the plurality of screw apertures 145 to have screws 30 inserted therein—the choice of where to insert screws 30 being within the purview of the surgeon given the patient's anatomy and fracture geometry.

As can be appreciated from FIG. 4, the placement of screws 30 within the screw apertures 145 can be at any number of insertion vectors deviating from the central axis 151 and between insertion vectors 152, 153. The choice of the placement of screws 30 within the screw apertures 145 is within the skill and judgment of the surgeon and may be dictated, generally, by the anatomy of the patient's pelvis A as well as the nature of the pattern of fracture F (FIG. A). Screws 30, as shown in FIG. 4, are generally placed through the screw apertures 145 in a manner that joins pieces of fractured bone and/or acquires sufficient purchase within the bone to hold the first bone plate 100 securely to the first bone portion 20 of the patient. The screw 30 can be a cortex screw, for example but not by way of limitation.

A bridging portion 160 is shown in FIGS. 1 and 1A as a generally central portion of the first bone plate 100. The bridging portion 160 generally lacks the presence of forming bridges 155 as the bridging portion 160 retains a substantially linear configuration while in use and is not generally deformable by the surgeon although in certain embodiments, the bridging portion 160 may be deformable by the surgeon. The bridging portion 160 is generally adjacent to the connecting bridge members 500. In the example shown, the bridging portion 160 extends across and between the two connecting bridge members 500.

The second bone plate 200 (shown with particularity in FIGS. 1, 1C, and 1D) is generally trapezoid in shape and is sized and shaped to conform to the second bone portion 35 of the patient (as shown in FIGS. A, 3, and 4) and, in particular, to the posterior column D of the pelvis A of the patient and, more particularly, to the quadrilateral surface C of the pelvis A of the patient. The second bone plate 200 includes a second bone engaging surface 205, a second tissue engaging surface 210, a proximal end 215, a distal end 220, a first side 225, and a second side 230, with the proximal end 215, the distal end 220, the first side 225, and the second side 230 defining a peripheral edge 235 of the second bone plate 200. The proximal end 215 is generally parallel to the distal end 220 while the first side 225 and the second side 230 generally diverge from the distal end 220 to the proximal end 215, although this configuration should not be considered to be limiting to the potential range of different acceptable shapes for the second bone plate 200. The second bone plate 200 further comprises a plurality of internal struts 240 connected to one another in a web-like pattern to define the general structure of the second bone plate 200. Where the internal struts 240 intersect, a plurality of secondary screw apertures 250 are placed. The internal struts 240 are deformable in three axes (similar to the forming bridges 155) and have sufficient memory such that a surgeon or other medical practitioner can bend, deform, or otherwise twist the second bone plate 200 into a new configuration that conforms the second bone plate 200 to the particular anatomical characteristics of the second bone portion 35 of the patient without deforming or otherwise encroaching upon the structural integrity and configuration of the plurality of secondary screw apertures 250 themselves and/or the second bone plate 200 itself.

The internal struts 240 further define a plurality of through holes 245 extending through the second bone plate 200 from the second tissue engaging surface 210 to the second bone engaging surface 205. The through holes 245 allow a surgeon to visualize the second bone portion 35 while placing the second bone plate 200 into position and/or allow a surgeon to visualize the second bone portion 35 via radiographic techniques without the generally radiopaque second bone plate 200 interrupting the surgeon's view. Although shown as a generally trapezoid shape, one of ordinary skill in the art would appreciate that the second bone plate 200 can be sized and shaped in various configurations to conform to the second bone portion 35 of the patient 15. For example, but not by way of limitation, the second bone plate 200 can be curved with respect to a plane defined by the second bone engaging surface 205, as shown with particularity in FIGS. 1A and 1B. Further, the shape, size, and configuration of the internal struts 240, as shown in the figures, is not intended to be considered as limiting and the internal struts 240 can be shaped, sized, and configured in any manner that provides the second bone plate 200 the rigidity and strength needed to reduce and fix fractures of the quadrilateral surface C of the patient 15, for example. See, for example, the alternative embodiments of the bone plating system 10 in FIGS. 4, and 7-9, discussed hereinafter.

The plurality of secondary screw apertures 250 (shown in detail in FIGS. 1B and 1C) extend from the second tissue engaging surface 210 to the second bone engaging surface 205. The secondary screw apertures 250 are similar in construction and operation to the screw apertures 145 in the first bone plate 100. In particular, each of the plurality of secondary screw apertures 250 include a screw head support surface 146a defining a screw head receiving volume 147a adjacent the second tissue engaging surface 210, and a screw shaft clearance surface 148a defining a screw shaft receiving volume 149a adjacent the second bone engaging surface 205. The screw shaft clearance surface 148a has a diameter less than a spherical diameter of the screw head support surface 146a—for example, an exemplary spherical diameter of the screw head support surface 146a is from about 6 to about 9 mm, while an exemplary diameter of the screw shaft clearance surface 148a is from about 3 to about 5.5 mm. A vertex 150a exists within each of the plurality of secondary screw apertures 250 where the screw shaft clearance surface 148a meets the screw head support surface 146a. (As shown in FIG. 1C) As such, each secondary screw aperture 250 is formed as a countersunk hole. This "countersunk hole" configuration of the secondary screw aperture 250 is such that the screw head support surface 146a is provided with a curved fillet in one embodiment or a conical chamfer in an alternative embodiment. In such a "countersunk hole" configuration of the secondary screw aperture 250, a head of the screw 40 is generally seated within the screw head receiving volume 147a and does not interact or engage substantially with tissue that may come into contact with the second tissue engaging surface 210 of the second bone plate 200.

Each of the plurality of second screw apertures 250 have a secondary central axis 251 running through a center of the screw head receiving volume 147a and the screw shaft receiving volume 149a from the second tissue engaging surface 210 to the first bone engaging surface 105.

As shown in FIG. 1B, the secondary central axis 251 is oriented at a 90-degree angle with respect to at least one of the second bone engaging surface 205 and the second tissue engaging surface 210 of the second bone plate 200. Alternatively, the secondary central axis 251 may be oriented at an angle of from about 45-degrees to about 90-degrees with respect to at least one of the second bone engaging surface 205 and the second tissue engaging surface 210 of the second bone plate 200 as depicted in the embodiment of FIG. 5. In use, a bone fastener such as a screw 40 (FIG. 1B) is inserted through one or more of the secondary screw apertures 250 along the secondary central axis 251—in a direction from the second tissue engaging surface 210 to the second bone engaging surface 205—and into the second bone portion 35 of the patient. In alternate embodiments, which will be appreciated by those of ordinary skill in the art given the present disclosure, the screw 40 can be inserted through one or more of the secondary screw apertures 250 at an angle less than or greater than that of the secondary central axis 251. For example, but not by way of limitation, the screw 40 can be inserted through the secondary screw apertures 250 at an angle deviating from the secondary central axis 251 from about 1 degree to about 40 degrees. As such, the angle at which the screw 40 can be inserted through the secondary screw apertures 250 can be +/−40 degrees from the secondary central axis 251 as indicated by secondary insertion vectors 252, 253. In preferred embodiments, the angle from which the screw 40 can deviate from the secondary central axis 251 while being inserted through the secondary screw apertures 250 is from about 1 to about 10 degrees; more preferably from about 10 to about 20 degrees; and more preferably from about 20 to about 40 degrees. The screw 40 may be of any width, size, or length and is generally chosen by the surgeon according to the thickness and physical characteristics of the bone into which the screw 40 is inserted. It is unnecessary for all of the plurality of secondary screw apertures 250 to have screws 40 inserted therein—the choice of where to insert screws 40 being within the purview of the surgeon given the patient's anatomy and fracture geometry.

As can be appreciated from FIG. 4, the placement of screws 40 within the secondary screw apertures 250 can be at any number of insertion vectors deviating from the secondary central axis 251 and between insertion vectors 252, 253. The choice of the placement of screws 40 within the secondary screw apertures 250 is within the skill and judgment of the surgeon and may be dictated, generally, by the anatomy of the patient's pelvis A as well as the nature of the pattern of fracture F (FIG. A). Screws 40, as shown in FIG. A, are generally placed through the secondary screw apertures 250 in a manner that joins pieces of fractured bone and/or acquires sufficient purchase within the bone to hold the second bone plate 200 securely to the second bone portion 35 of the patient. The screw 40 can be a cortex screw, for example but not by way of limitation.

The second bone plate 200 further includes at least one reduction instrument engaging aperture 260 for receiving a surgical instrument (such as a ball spike, not shown) capable of applying a force vector 261 generally at a 90 degree angle to the second tissue engaging surface 210 of the second bone plate 200 to urge or bring the second bone engaging surface 205 of the second bone plate 200 into contact with and generally adjacent to the second bone portion 35 (e.g., the quadrilateral surface C) of the patient. The reduction instrument engaging aperture 260 may also be configured to accept other reduction and fixation instrumentation such as forceps, clamps, and other such devices, which may be individual tools or provided as part of a kit with the bone plating system 10.

Figure 2:
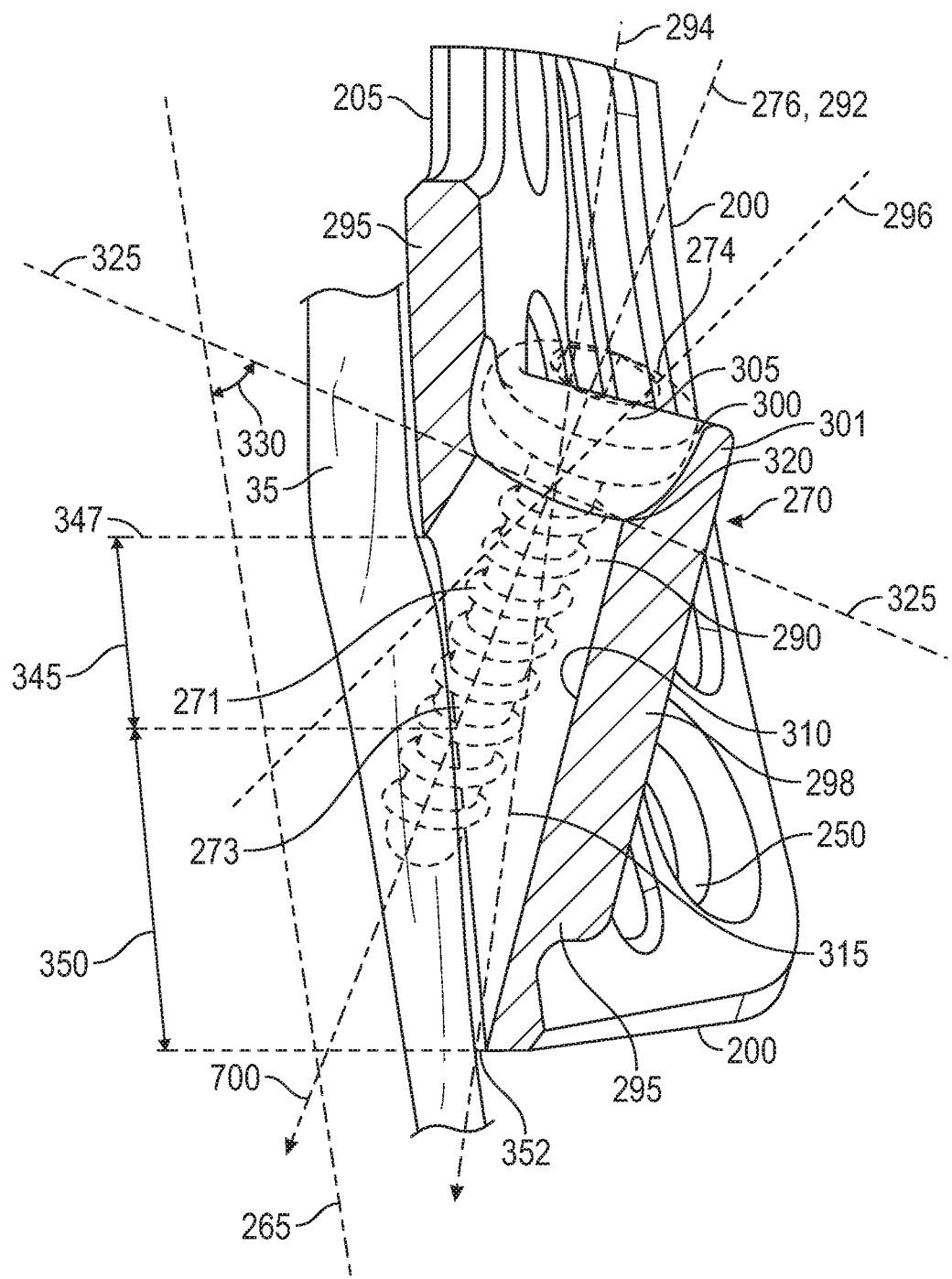
FIG. 2 is a cross-sectional view along line A-A of FIG. 1 of the bone plating system of the present disclosure as shown in FIG. 1.

As shown in FIG. 1, the proximal end 215 of the second bone plate 200 is spaced a first distance 242 away from the second edge 120 of the first bone plate 100 and the distal end 220 of the second bone plate 200 is spaced a second distance 244 away from the second edge 120 of the first bone plate 100 with the second distance 264 being larger than the first distance 262. As shown in FIGS. 1B and 2, the second bone engaging surface 205 of the second bone plate 200 includes a bone engaging axis 265 extending from the proximal end 215 of second bone plate 200 to the distal end 220 of the second bone plate 200. The bone engaging axis 265 is generally a straight line fit to a series of data points representing the second bone engaging surface 205 of the second bone plate 200.

Figure 2A:
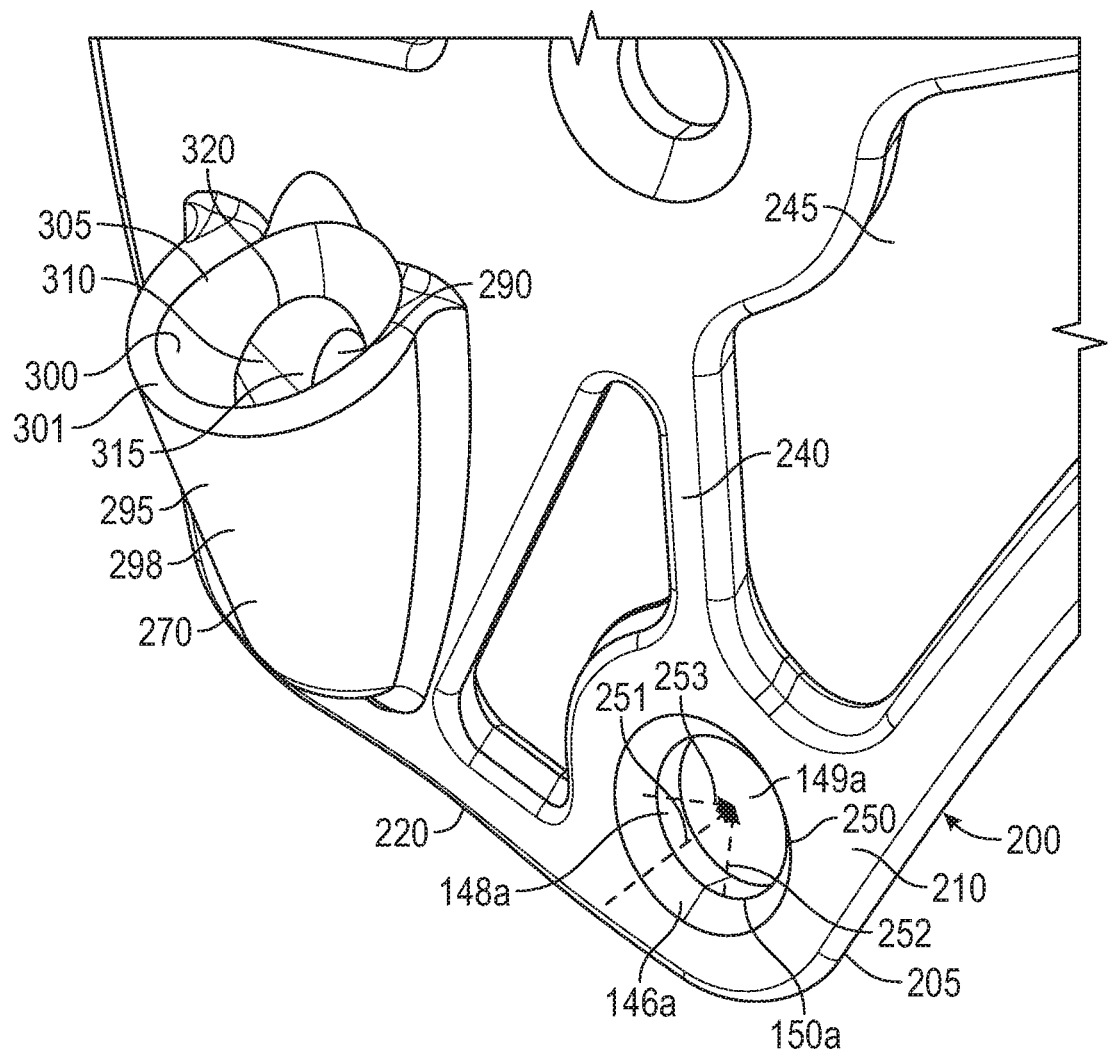
FIG. 2A is a detailed perspective view of the distal end of the second bone plate of the bone plating system of the present disclosure as shown in FIG. 1.

The second bone plate 200 includes at least one securing port 270 with one such securing port being shown in FIGS. 1-1D. The at least one securing port 270 of the second bone plate 200 is shown more particularly in cross-section in FIG. 2 along a line A-A of FIG. 1 (and in close-up detail in FIG. 2A) and with respect to a fastener 271 (shown in dashed line in FIG. 2) and the second bone portion 35, where the fastener 271 has a shaft 273 and a head 274. The fastener 271 can be a cortex screw, for example but not by way of limitation. A fastener central axis 276 runs through a center of the fastener 271—i.e., the fastener central axis 276 is a line extending longitudinally through a center of the head 274 and a center of the shaft 273 of the fastener 271. The securing port 270 includes a bore 290 extending from the second tissue engaging surface 210 to the second bone engaging surface 205 in a direction substantially oriented toward the distal end 220 and away from the proximal end 215 of the second bone plate 200. In alternative embodiments, the bore 290 may extend from the second tissue engaging surface 210 to the second bone engaging surface 205 in a direction substantially oriented toward the peripheral edge 235 and away from an inner portion of the second bone plate 200 with the inner portion being generally defined in one embodiment as a point on the second bone plate 200 that is equidistant from all points along the peripheral edge 235. In an additional embodiment, shown more particularly in FIG. 8, for example but not by way of limitation, the bore 290 may extend from the second tissue engaging surface 210 to the second bone engaging surface in a direction substantially oriented toward the peripheral edge 235 and away from an offset point (not shown) of the second bone plate. The offset point is generally defined as a point that is part of the interior of the second bone plate 200 and is not equidistant from all points along the peripheral edge 235. A bore central axis 292 runs through a center of the bore 290—i.e., the bore central axis 292 is a line extending longitudinally through a center of the bore 290 in a direction substantially oriented toward the distal end 220 and away from the proximal end 215 of the second bone plate 200. As shown in FIG. 2, when the fastener 271 is within the at least one securing port 270 in at least one configuration, the fastener central axis 276 is adjacent to and/or coextensive with the bore central axis 292.

In alternate embodiments, which will be appreciated by those of ordinary skill in the art given the present disclosure, the fastener 271 can be inserted into the bore 290 of the at least one securing port 270 at an angle less than or greater than that of the bore central axis 292. For example, but not by way of limitation, the fastener 271 can be inserted through the bore 290 at an angle deviating from the bore central axis 292 from about 1 degree to about 75 degrees. As such, the angle at which the fastener 271 can be inserted through the bore 290 can be +/−75 degrees from the bore central axis 292 as indicated generally by fastener insertion vectors 294, 296. In preferred embodiments, the angle from which the fastener 271 can deviate from the bore central axis 292 while being inserted through the bore 290 is from about 1 to about 10 degrees; from about 10 to about 20 degrees; from about 20 to about 35 degrees; from about 35 to about 50 degrees; from about 50 to about 65 degrees; and from about 60 to about 75 degrees. In particular, it is contemplated that insertion of the fastener 271 can deviate from the bore central axis 292 in an amount ranging from where insertion vector 296 is at an angle of about 10 degrees measured from the bone engaging axis 265 and insertion vector 294 is at an angle of about 90 degrees measured from the bone engaging axis 265. In an alternate embodiment, insertion of fastener 271 can deviate from the bore central axis 292 in an amount ranging from where insertion vector 296 is at an angle of about 15 degrees measured from the bone engaging axis 265 and insertion vector 294 is at an angle of about 33 degrees measured from the bone engaging axis 265.

In further detail, the securing port 270 has a wall 295 surrounding the bore 290. The wall 295 has an exterior surface 298. The wall 295 defines a fastener head support surface 300 opposite to the exterior surface 298 of the wall 295. The fastener head support surface 300 defines a fastener head receiving volume 305 of the bore 290 adjacent to the second tissue engaging surface 210. In the embodiment of FIG. 2 (and as shown in further detail in FIG. 2A), the exterior surface 298 is spaced from the fastener head support surface 300 by a lip portion 301 of the wall 295. The fastener head support surface 300 defines a fastener head receiving volume 305 of the bore 290 adjacent to the second tissue engaging surface 210. The wall 295 also defines a fastener shaft clearance surface 310 defining a generally frustoconical shaped fastener shaft receiving volume 315 of the bore 290 adjacent to the second bone engaging surface 205. In use, when the fastener 271 is placed within the bore 290, the head 274 of the fastener 271 is in a "shrouded" configuration—i.e., the head 274 of the fastener 271 is nested within the fastener head receiving volume 305 and does not extend (or does not substantially extend depending upon the embodiment and/or configuration of the fastener 271) into tissue adjacent the second tissue engaging surface 210 of the second bone plate 200. In one embodiment, a spherical diameter of the fastener head support surface 300 is from about 6 mm to about 9 mm. The fastener shaft clearance surface 310 is generally shaped as an ellipse and has a length along a major radius of from about 3 mm to about 9 mm and a length along a minor radius of from about 3 mm to about 6 mm at an upper edge of the fastener shaft clearance surface 310 near the second tissue engaging surface 310 and a length along a major radius of from about 3 mm to about 23 mm and a length along a minor radius of from about 3 mm to about 6 mm at a lower edge of the fastener shaft clearance surface 310 near the second bone engaging surface 305. As at least one of the length along the major radius and the length along the minor radius found at the upper edge of the fastener shaft clearance surface 310 are smaller than at least one of the length along the major radius and the length along the minor radius found at the lower edge of the fastener shaft clearance surface 310, the frustoconical shape of the fastener shaft clearance surface 310 can be appreciated. Further, the lengths along the major and minor radii found at the upper edge of the fastener shaft clearance surface 310 may be identical to the lengths along the major and minor radii of the lower edge of the fastener shaft clearance surface 310. In this manner, the fastener head receiving volume 305 is formed as a countersunk hole. This "countersunk hole" configuration is such that the fastener head support surface 300 is provided with a curved fillet in one embodiment or a conical chamfer in an alternative embodiment. In such a "countersunk hole" configuration of the fastener head receiving volume 305, the head 274 of the fastener 271 is generally seated within the fastener head receiving volume 305 and does not interact or engage substantially with tissue that may come into contact with the second tissue engaging surface 210 of the second bone plate 200. As shown in the configuration of FIG. 1, the bore central axis 292 is a line extending longitudinally through a center of the fastener head receiving volume 305 and a center of the fastener shaft receiving volume 315 of the bore 290.

The fastener head support surface 300 is adjacent to the fastener shaft clearance surface 310 such that the fastener head support surface 300 and the fastener shaft clearance surface 310 have a bore vertex 320 extending around at least a portion of the bore 290. The fastener head support surface 300 has a fastener support axis 325 adjacent to the bore vertex 320. The fastener support axis 325 extends at a first angle 330 that is less than or equal to 90 degrees relative to the bone engaging axis 265. In one embodiment, the first angle 330 can be between 1 and 15 degrees. In other embodiments, the first angle 330 can be between 15 and 35 degrees, 35 and 60 degrees, 60 and 75 degrees, and 75 and 90 degrees. In a preferred embodiment, the first angle 330 is between 45 and 80 degrees, preferentially being between 55 and 75 degrees.

The generally frustoconical shape of the fastener shaft receiving volume 315 can be appreciated from the view of the bore 290 of FIG. 2 wherein a first distance 345 measured from the bore central axis 292 to a first portion 347 of the fastener shaft clearance surface 310 near the proximal end 215 of the second bone plate 200 is less than a second distance 350 measured from the bore central axis 292 to a second portion 352 of the fastener shaft clearance surface 310 near the distal end 220 of the second bone plate 200. As one of ordinary skill in the art would appreciate from the present disclosure, the first distance 345 and the second distance 350 can vary depending on the angle at which the fastener 271 is placed within the bore 290 and there may be a configuration wherein the first distance 345 and the second distance 350 are identical yet the fastener shaft receiving volume 315 retains its generally frustoconical shape as defined by the fastener shaft clearance surface 315 extending from the bore vertex 320 to the second bone engaging surface 205 of the second bone plate 200. The frustoconical shape of the fastener shaft receiving volume 315 allows the fastener 271 to approach the second bone portion 35 at an angle that deviates from the bore central axis 292 by +/−40 degrees.

Figure 2B:
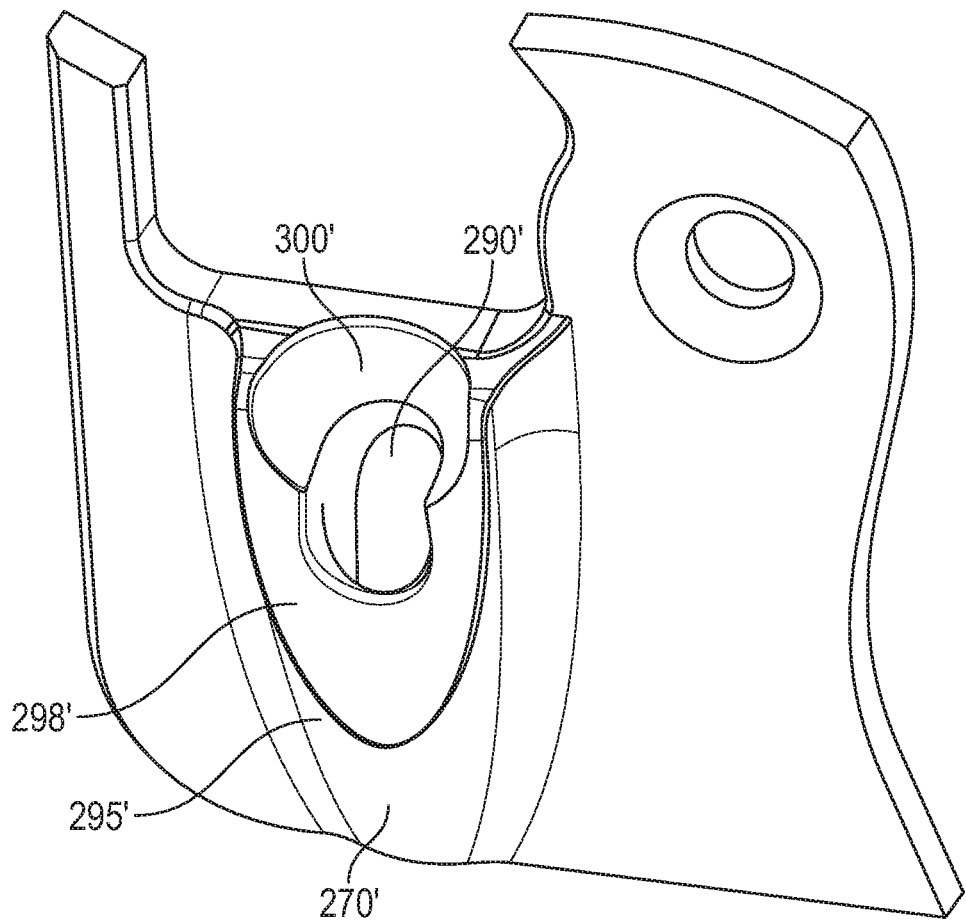
FIG. 2B is a detailed perspective view of an alternative embodiment of the distal end of the second bone plate of the bone plating system of the present disclosure as shown in FIG. 1.

Shown in FIG. 2B is a securing port 270' that is constructed identical to the securing port 270, except as discussed below. For purposes of brevity, the securing port 270' will use similar reference numerals to the securing port 270, but such reference numerals will include a "'" suffix. Also, for purposes of clarity, common elements between the securing port 270 and the securing port 270' will not be described, but such are incorporated herein by reference. The securing port 270 is provided with a wall 295' surrounding a bore 290'. The wall 295' has an exterior surface 298'. The wall 295' also defines a fastener head support surface 300' intersecting the exterior surface 298' of the wall 295'. Because the fastener head support surface 300' intersects the exterior surface 298' (i.e., being devoid of the lip portion 301), the securing port 270' can be fabricated from thinner material making the securing port 270' less costly to manufacture. The exterior surface 298' may have a planar configuration as depicted in FIG. 2B.

The second bone plate 200 in certain embodiments further includes one or more tertiary fastening members 400 with two such tertiary fastening members 400 being shown in the embodiment of the bone plating system 10 of FIGS. 1-1D. As shown in FIG. 1, the tertiary fastening members 400 are coextensive with the peripheral edge 235 of the second bone plate 200 near the proximal end 215 thereof. Although in other contemplated embodiments the tertiary fastening members 400 may be coextensive with the peripheral edge 235 near the distal end 220 or coextensive with the peripheral edge 235 near both the distal and proximal ends 220, 215, respectively, of the second bone plate 200. In particular, the tertiary fastening members 400 are connected to the second bone plate 200 via external struts 402 extending from the first side 225 and second side 230 of the second bone plate 200 and connecting with the tertiary fastening members 400. Like the forming bridges 155 and the internal struts 240, the external struts 402 are deformable by the surgeon in at least two axes (and in certain embodiments, three axes) thereby allowing the tertiary fastening members 400 to be placed into a configuration such that a bone contacting surface 404 (shown in detail in FIG. 1A) of the tertiary fastening members 400 is in contact with the second bone portion 35. The tertiary fastening members 400 include at least one tertiary screw aperture 406 constructed in a similar manner as the screw apertures 145 and the secondary screw apertures 250 thereby allowing the placement of a bone screw 50 (as shown in FIG. 1B) through the tertiary screw apertures 400 and into the second bone portion 35. The bone screw 50 may be a polyaxial bone screw.

Figure 8:
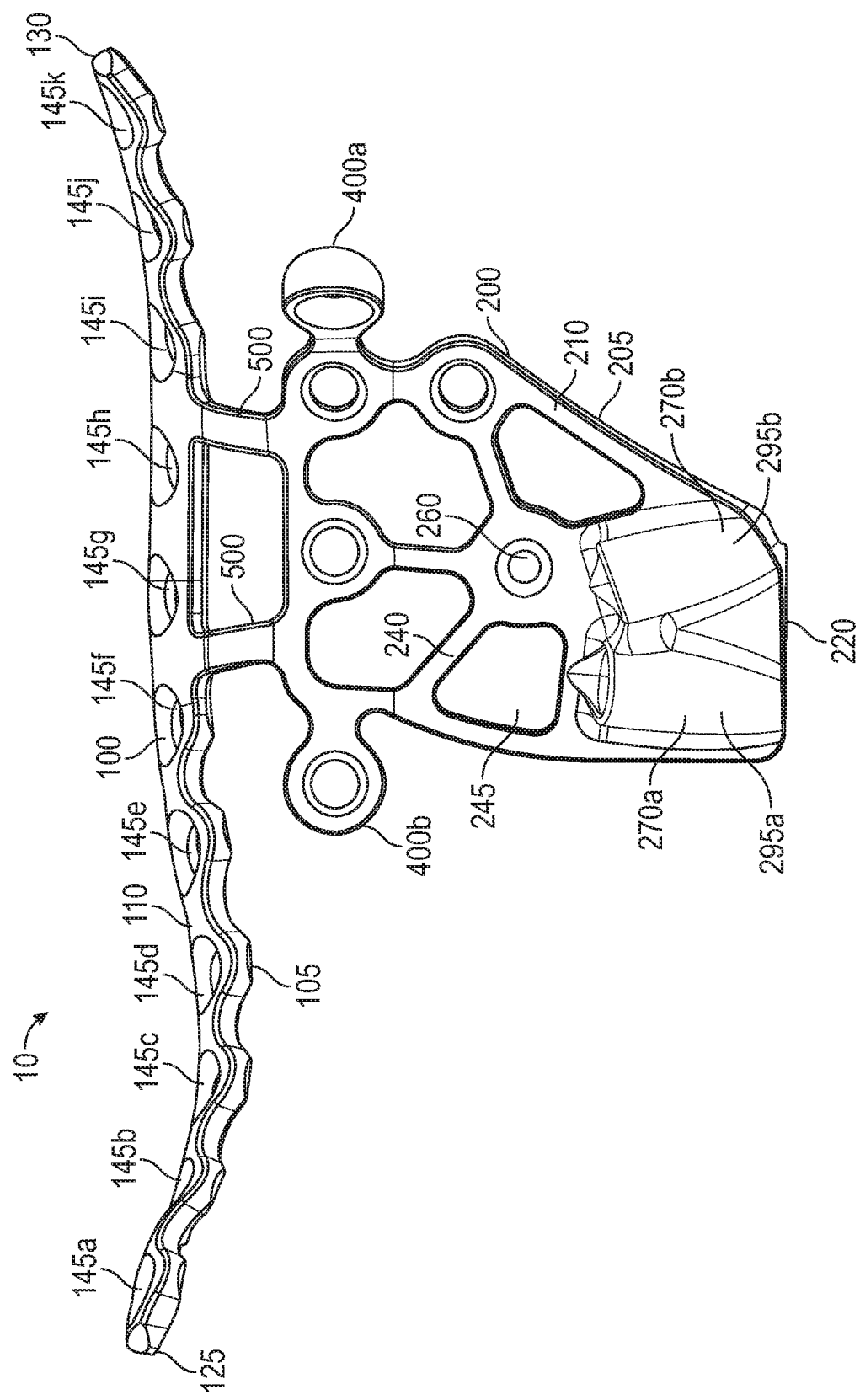
FIG. 8 is a front perspective view of an additional alternative embodiment of a bone plating system of the present disclosure.

In certain further embodiments shown in FIGS. 5A-5D and 8, the second bone plate 200 particularly includes two securing ports 270a, 270b. Although it is shown in FIGS. 5A-5D and 8 that the two securing ports 270a, 270b are adjacent to one another at the distal end 220 of the second bone plate 200, one of ordinary skill in the art will appreciate that the two securing ports 270a, 270b can be placed at any location within the second bone plate 200 either together, adjacent, or separately and that the two securing ports 270a, 270b need not be placed in a parallel configuration with respect to one another. In particular, the two securing ports 270a, 270b may be placed at an angle to one another such that the two securing ports 270a, 270b converge and or diverge from one another depending on the angular positioning of each to the other as shown in FIG. 8, for example but not by way of limitation. Furthermore, the second bone plate 200 may include three, four, five, six, or any number of securing ports with the number of such securing ports only being limited by the size and configuration of the second bone plate 200. The two securing ports 270a, 270b are generally identical to the at least one securing port 270. With respect to the views of the two securing ports 270a, 270b shown in FIGS. 5A-5D it should be readily apparent that the wall 295a of the securing port 270a has a height that is greater than a height of the wall 295b of the securing port 270b. Furthermore, each of securing ports 270a, 270b of FIGS. 5A-5D and 8 have a concomitant fastener central axis 276 generally adjacent bore vertex 320. The first angle 330 residing between the fastener support axis 325 and the bone engaging axis 265 of the second bone plate 200 may be identical in the securing ports 270a, 270b, or the first angle 330 may be different in each of securing ports 270a, 270b. In this manner, the second bone plate is provided with two securing ports 270a, 270b that each may have fastener support axes 325 that intersect with the bone engaging axis 265 of the second bone plate 200 at first angles 330 that are identical or different than one another.

The at least one connecting bridge member 500, with two connecting bridge members 500 shown in FIGS. 1-1D, comprise a proximal end 505, a distal end 510, a first side 515, and a second side 520 with the proximal end 505, the distal end 510, the first side 515, and the second side 520 defining an outer peripheral edge 525. The connecting bridge members 500 are capable of being deformed in three axes, with deformation in two axes being generally preferred, and have sufficient memory such that a surgeon or other medical practitioner can bend and twist the connecting bridge members 500 such that the first bone plate 100 and the second bone plate 200 are placed into a new configuration with respect to one another that conforms the bone plating system 10 to the anatomy of the pelvis A of the patient 15. The connecting bridge members 500 are shown as being substantially rectangular in shape with the proximal end 505 and the distal end 510 being spaced a distance away from and generally parallel to one another, while the first side 515 and the second side 520 being spaced a distance away from and generally parallel to one another. The proximal end 505 of the connecting bridge member 500 is adjacent to, in contact with, or connected to the second edge 120 along the bridging portion 160 of the first bone plate 100.

As one of ordinary skill in the art will appreciate, the connecting bridge member 500, while shown as generally rectangular in shape in FIGS. 1-1D, could be any shape or configuration—e.g., trapezoid, triangle, square, frustoconical, conical, circular, or fanciful-so long as the connecting bridge member 500 is capable of connecting the first bone plate 100 to the second bone plate 200 in a manner that allows the first and second bone plates 100, 200, respectively, to be configured with respect to one another so as to fit the anatomy of the pelvis A of the patient 15, for example. Additionally, it can be appreciated from FIGS. 1B and 1C that connecting bridge member 500 can be curved or in a configuration having an arc running a length of the connecting bridge member 500 from the distal end 510 to the proximal end 505 thereby allowing the first bone plate 100 to be generally adjacent the first bone portion 20 (e.g., the pelvic brim B of FIG. A) while the second bone plate 200 is generally adjacent the second bone portion 35 (e.g., the quadrilateral surface C of FIG. A) within the patient 15.

The first bone plate 100, second bone plate 200, and the connecting bridge members 500 are preferably monolithically formed of titanium, implant grade stainless steel, or composites and alloys of same. In one embodiment, the first bone plate 100, the second bone plate 200, and the connecting bridge members 500 are formed of annealed stainless steel. As mentioned herein, the forming bridges 155, internal struts 240, external struts 402, and connecting bridge members 500 are capable of being bent, twisted, and otherwise deformed by a surgeon in order to change the configuration of the bone plating system 10 to a new configuration more closely approximating the patient's specific anatomy. It should be understood by one of ordinary skill in the art that while the forming bridges 155, internal struts 240, external struts 402, and connecting bridge members 500 have some elasticity, the remaining structure of the bone plating system 10 should be rigid enough for appropriately fulfilling its fracture reduction and bone support functions, i.e., that the bone plating system 10 is rigid enough to sufficiently stabilize the first and second bone portions 20, 35, respectively, and thereby reduce and stabilize the fracture F running through the first and second bone portions 20, 35, of the patient 15 respectively.

Figure 7:
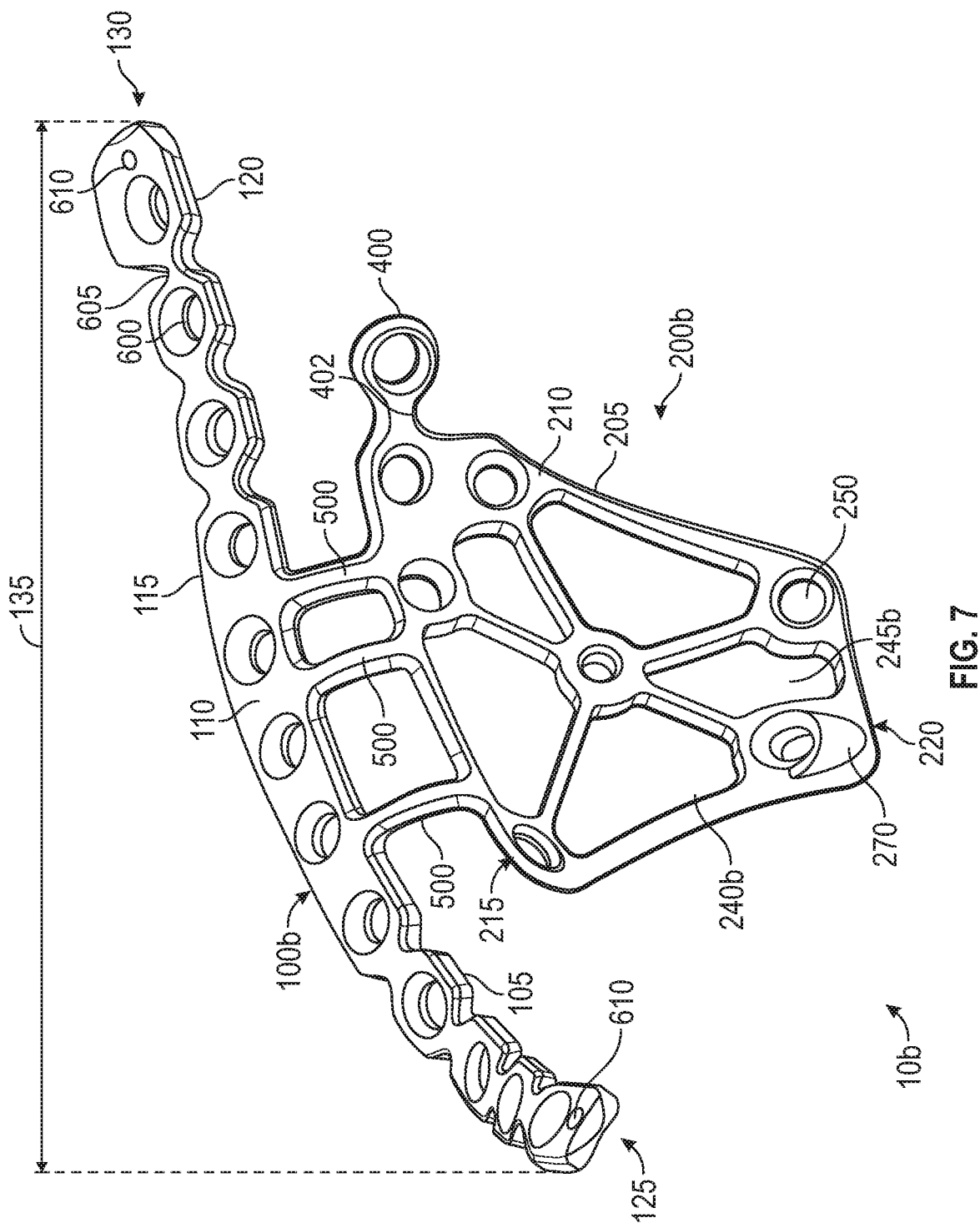
FIG. 7 is a perspective view of a further alternative embodiment of a bone plating system of the present disclosure.

Alternative embodiments of the bone plating system 10 are shown in FIGS. 6-7 and indicated via reference numerals 10a and 10b, respectively. The bone plating systems 10a and 10b are generally the same as bone plating system 10 with several of the individual components being found in greater or lesser numbers. Additionally, the shape and configuration of the first and second bone plates 100a, 200a respectively are sized and shaped differently than the first and second bone plates 100, 200.

The bone plating system 10a shown in FIG. 6 includes a first bone plate 100a, a second bone plate 200a, a tertiary fastening member 400, and three connecting bridge members 500. The first bone plate 100a includes a first bone engaging surface 105, a tissue engaging surface 110, a first edge 115, a second edge 120, a first end 125, and a second end 130. A length 135 extends from the first end 125 to the second end 130 of the first bone plate 100a. Spaced equally along a longitudinal axis running along the length 135 of the first bone plate 100a are a plurality of screw apertures 600 and forming bridges 605 generally placed between the screw apertures 600. In the embodiment of FIG. 6, the first bone plate 100a comprises ten screw apertures 600 and five forming bridges 605. The screw apertures 600 are identical to the screw apertures 145, and the forming bridges 605 are identical to the forming bridges 155 in shape, function, structure, and positioning considering the differences in the number of each.

The first bone plate 100a includes at least one securing channel 610 with two such securing channels 610 being shown in the embodiment of FIG. 6. The securing channels 610 are positioned generally on the first end 125 and the second end 130 of the first bone plate 100a and define a channel through the first bone plate 100a extending from the first tissue engaging surface 110 to the first bone engaging surface 105. The securing channels 610 allow the placement of a stabilizing tool (not shown), such as a K-wire, probe, or other surgical instrument, to be placed through the first bone plate 100a and into the first bone portion 20 thereby positioning and holding/locking the first bone plate 100a adjacent the first bone portion 20.

The second bone plate 200a includes a second bone engaging surface 205, a second tissue engaging surface 210, a proximal end 215, and a distal end 220. The second bone plate 200a further includes internal struts 240a, through holes 245a, and secondary screw apertures 250. The internal struts 240a are generally identical to internal struts 240 albeit the internal struts 240a are arranged in a different web-like pattern than internal struts 240. Likewise, the through holes 245a are generally identical to through holes 245 albeit the through holes 245a are shaped and sized differently than the through holes 245. The second bone plate 200a also includes at least one securing port 270 and at least one tertiary fastening member 400 connected to the second bone plate 200a via an external strut 402. Further, the bone plating system 10a includes a plurality of connecting bridge members 500 connecting the first bone plate 100a to the second bone plate 200a with three such connecting bridge members 500 shown in the embodiment of the bone plating system 10a shown in FIG. 6. In use, the bone plating system 10a is placed within the pelvis A of a patient in the same manner using the same tools and screws 30, 40, 50 and fastener 271 as bone plating system 10 with the one difference that a stabilizing tool (such as a K-wire, not shown) can be inserted within the securing channels 610 through the first bone plate 100a and into the first bone portion 20 to hold the first bone plate 100a in position against the first bone portion 20 during the surgical procedure.

The bone plating system 10b shown in FIG. 7 includes a first bone plate 100b, a second bone plate 200b, a tertiary fastening member 400, and three connecting bridge members 500. The first bone plate 100b includes a first bone engaging surface 105, a tissue engaging surface 110, a first edge 115, a second edge 120, a first end 125, and a second end 130. A length 135 extends from the first end 125 to the second end 130 of the first bone plate 100b. Spaced equally along a longitudinal axis running along the length 135 of the first bone plate 100b are a plurality of screw apertures 600 and forming bridges 605 generally placed between the screw apertures 600. In the embodiment of FIG. 7, the first bone plate comprises twelve screw apertures 600 and seven forming bridges 605. In general and with respect to all embodiments of the first bone plate (for example, first bone plate 100, 100a, or 100b, but not by way of limitation) shown and described herein, the number of screw apertures 145 and/or 600 may range from 1 to 15, although the number of such screw apertures 145 and/or 600 should not be considered as limiting with respect to the intended scope of the present disclosure. The screw apertures 600 are identical to the screw apertures 145 and the forming bridges 605 are identical to the forming bridges 155 in shape, function, structure, and positioning considering the differences in the number of each.

The first bone plate 100b includes at least one securing channel 610 with two such securing channels 610 being shown in the embodiment of FIG. 7. The securing channels 610 are positioned generally on the first end 125 and the second end 130 of the first bone plate 100b and define a channel through the first bone plate 100b extending from the first tissue engaging surface 110 to the first bone engaging surface 105. The securing channels 610 allow the placement of a stabilizing tool (not shown), such as a K-wire, probe, or other surgical instrument, to be placed through the first bone plate 100b and into the first bone portion 20 thereby positioning and holding/locking the first bone plate 100b adjacent the first bone portion 20.

The second bone plate 200b includes a second bone engaging surface 205, a second tissue engaging surface 210, a proximal end, and a distal end 220. The second bone plate 200b further includes internal struts 240b, through holes 245b, and secondary screw apertures 250. The internal struts 240b are generally identical to internal struts 240 albeit the internal struts 240b are arranged in a different web-like pattern than internal struts 240. Likewise, the through holes 245b are generally identical to through holes 245 albeit the through holes 245b are shaped and sized differently than the through holes 245. The second bone plate 200b also includes at least one securing port 270 and at least one tertiary fastening member 400 connected to the second bone plate 200a via an external strut 402. Further, the bone plating system 10b includes a plurality of connecting bridge members 500 connecting the first bone plate 100a to the second bone plate 200a with three such connecting bridge members 500 shown in the embodiment of the bone plating system 10b shown in FIG. 7. In use, the bone plating system 10b is placed within the pelvis A of a patient in the same manner using the same tools and screws 30, 40, 50 and fastener 271 as bone plating system 10 with the one difference that a stabilizing tool (not shown) can be inserted within the securing channels 610 through the first bone plate 100b and into the first bone portion 20 to hold the first bone plate 100b in position against the first bone portion 20 during the surgical procedure.

Figure 9A:
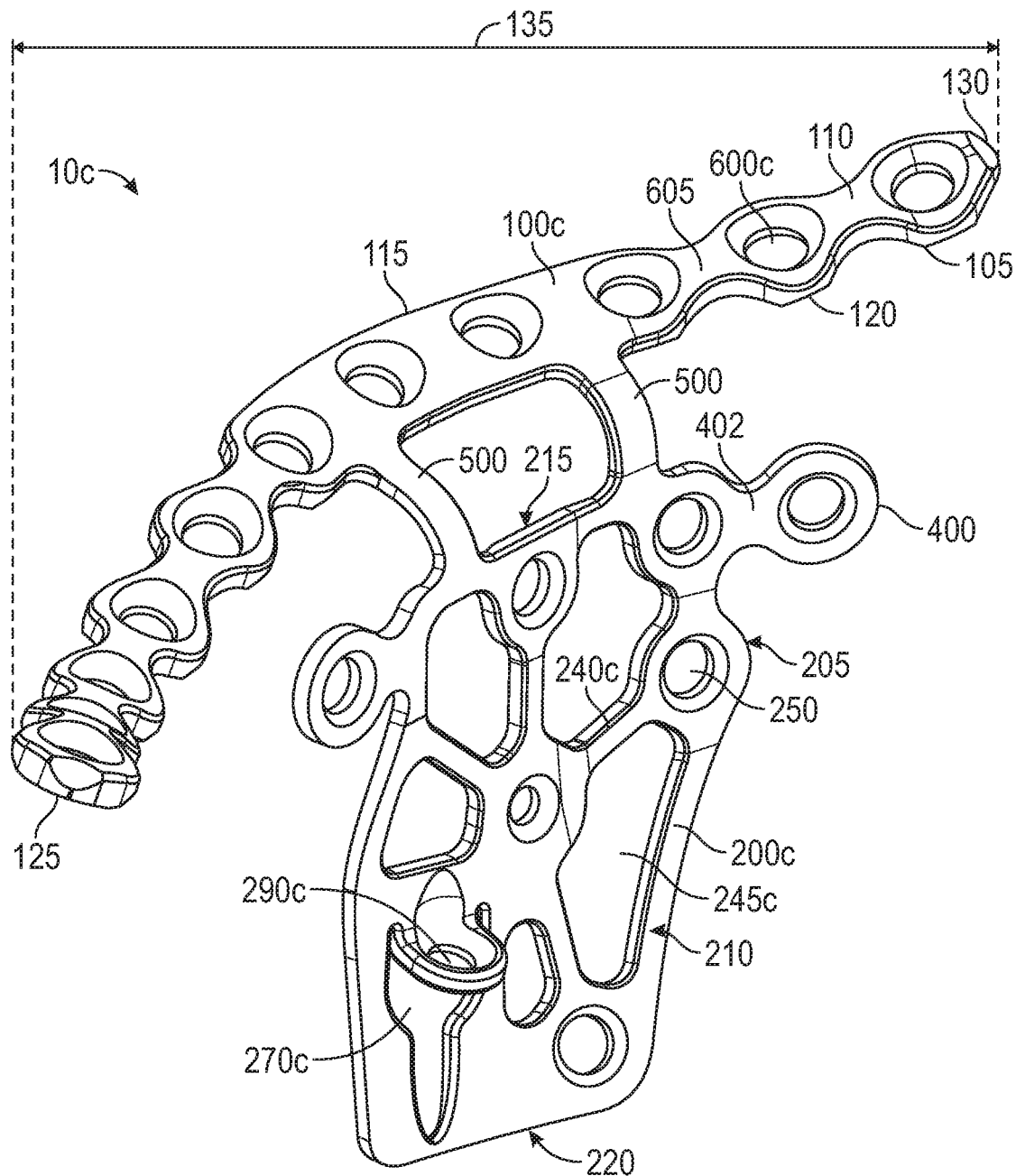
FIG. 9A is a front perspective view of an alternative embodiment of a bone plating system of the present disclosure.
Figure 9B:
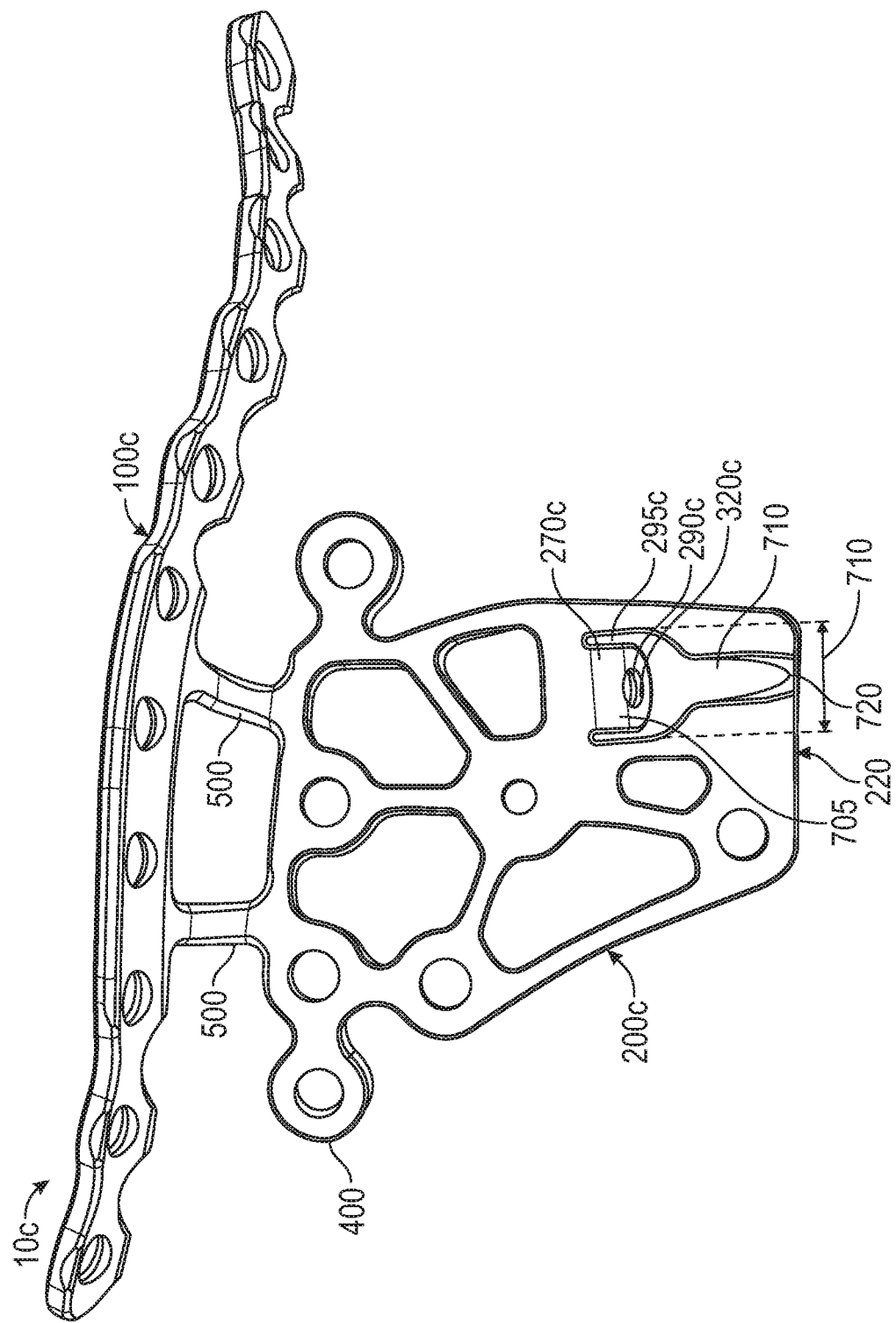
FIG. 9B is a rear perspective view of the bone plating system of the present disclosure as shown in FIG. 9A.
Figure 9C:
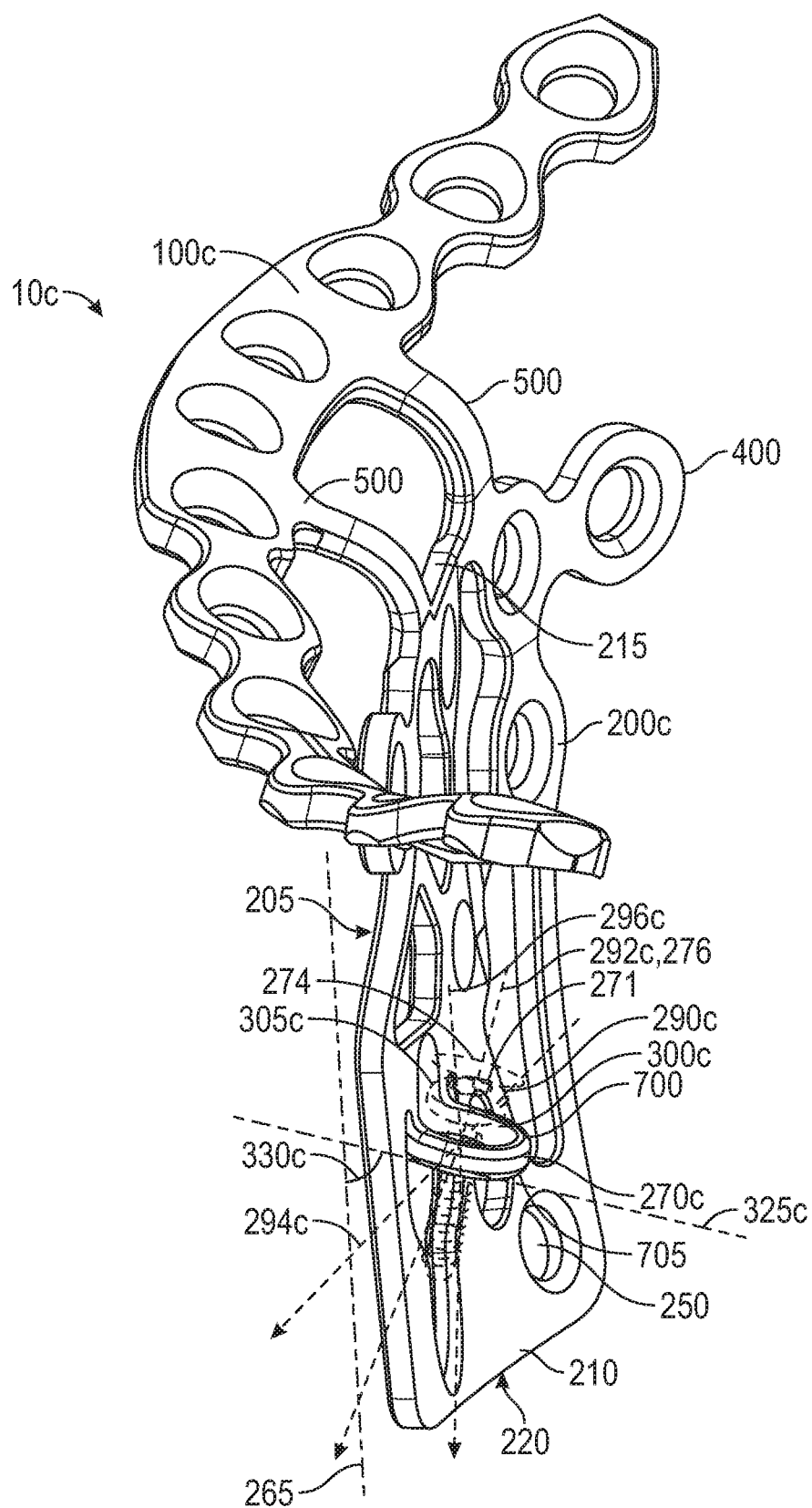
FIG. 9C is a side perspective view of the bone plating system of the present disclosure as shown in FIG. 9A.
Figure 10A:
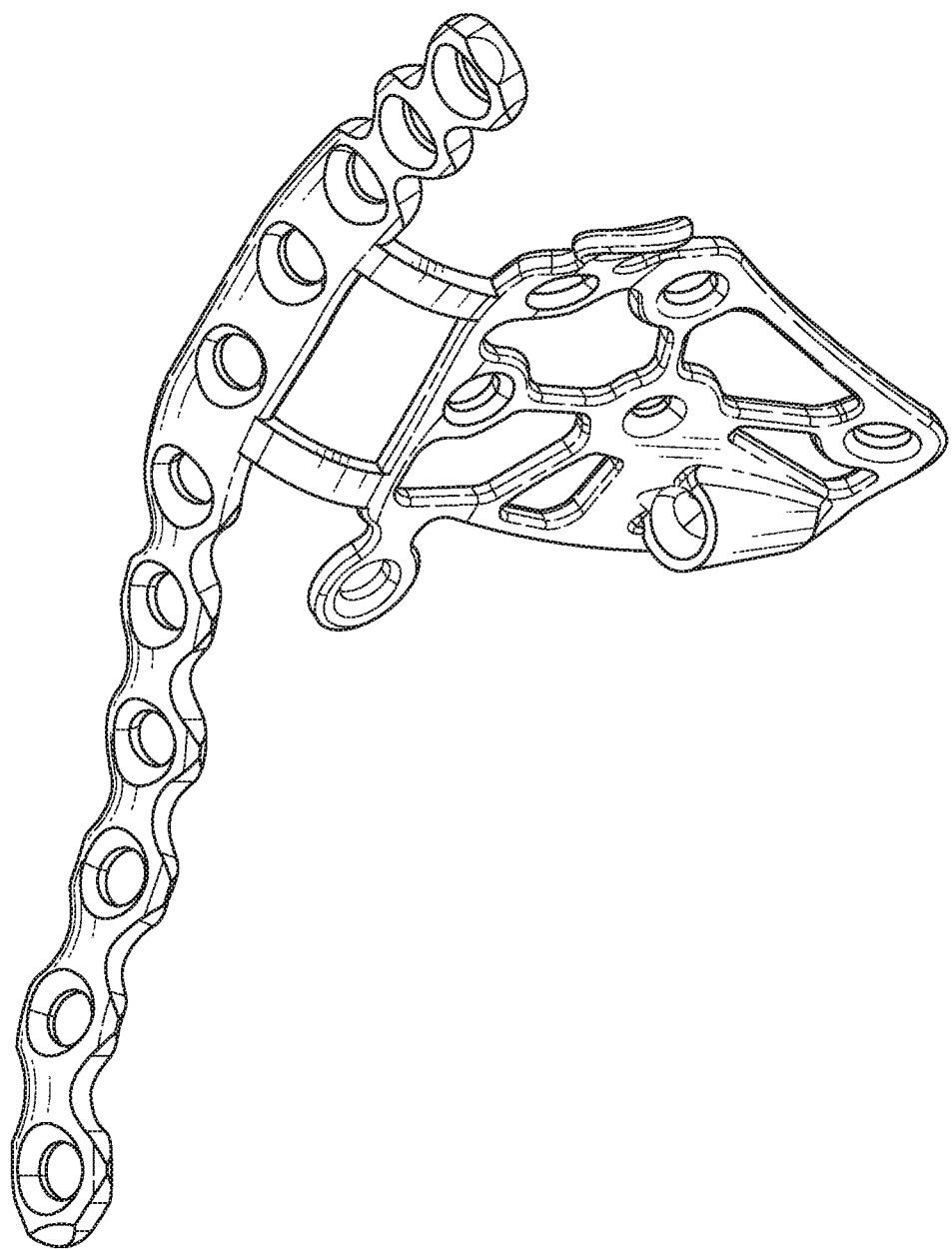
FIG. 10A is a perspective view of an embodiment of a bone plating system of the present disclosure.
Figure 10B:
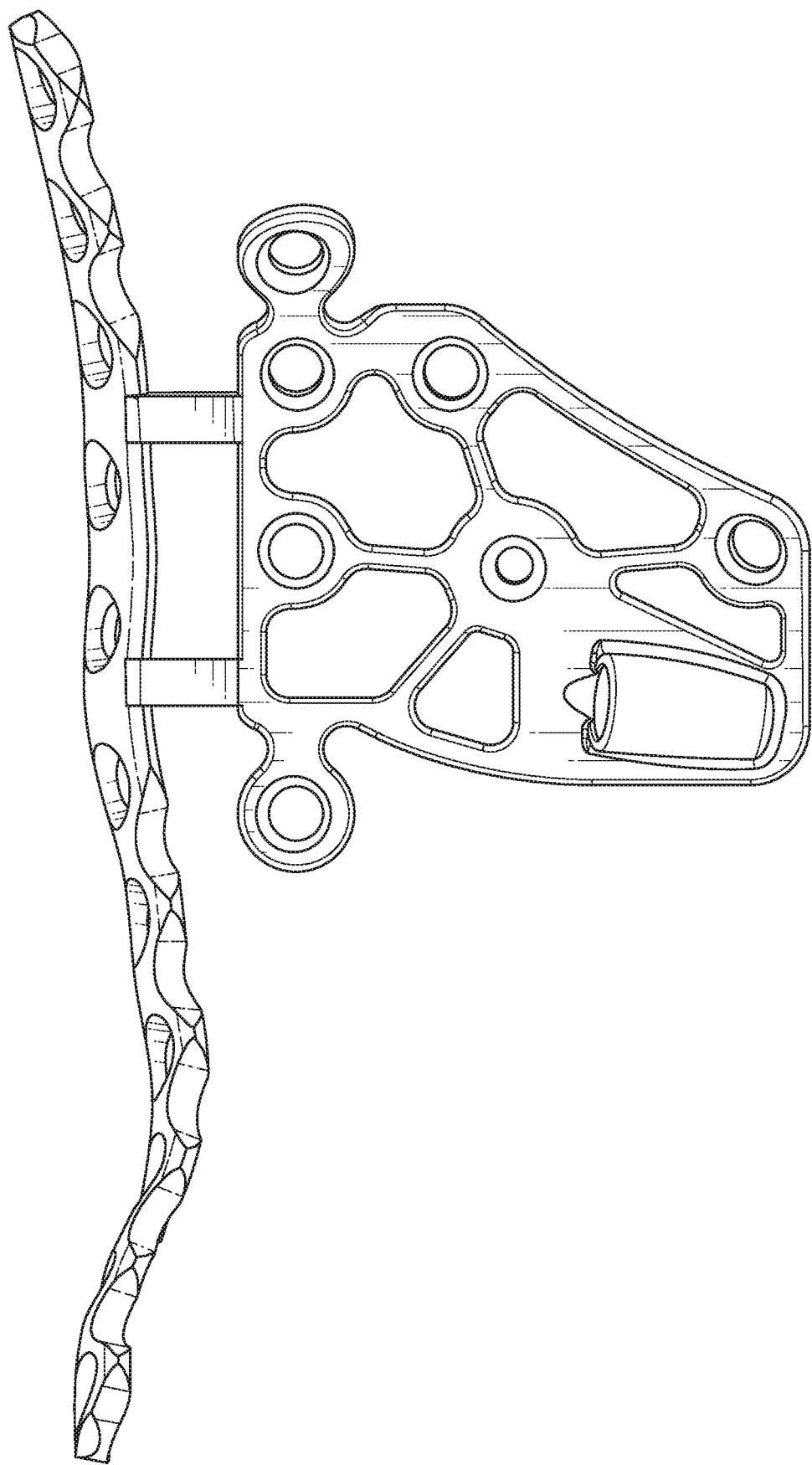
FIG. 10B is front perspective view of the bone plating system of the present disclosure as shown in FIG. 10A.
Figure 10C:
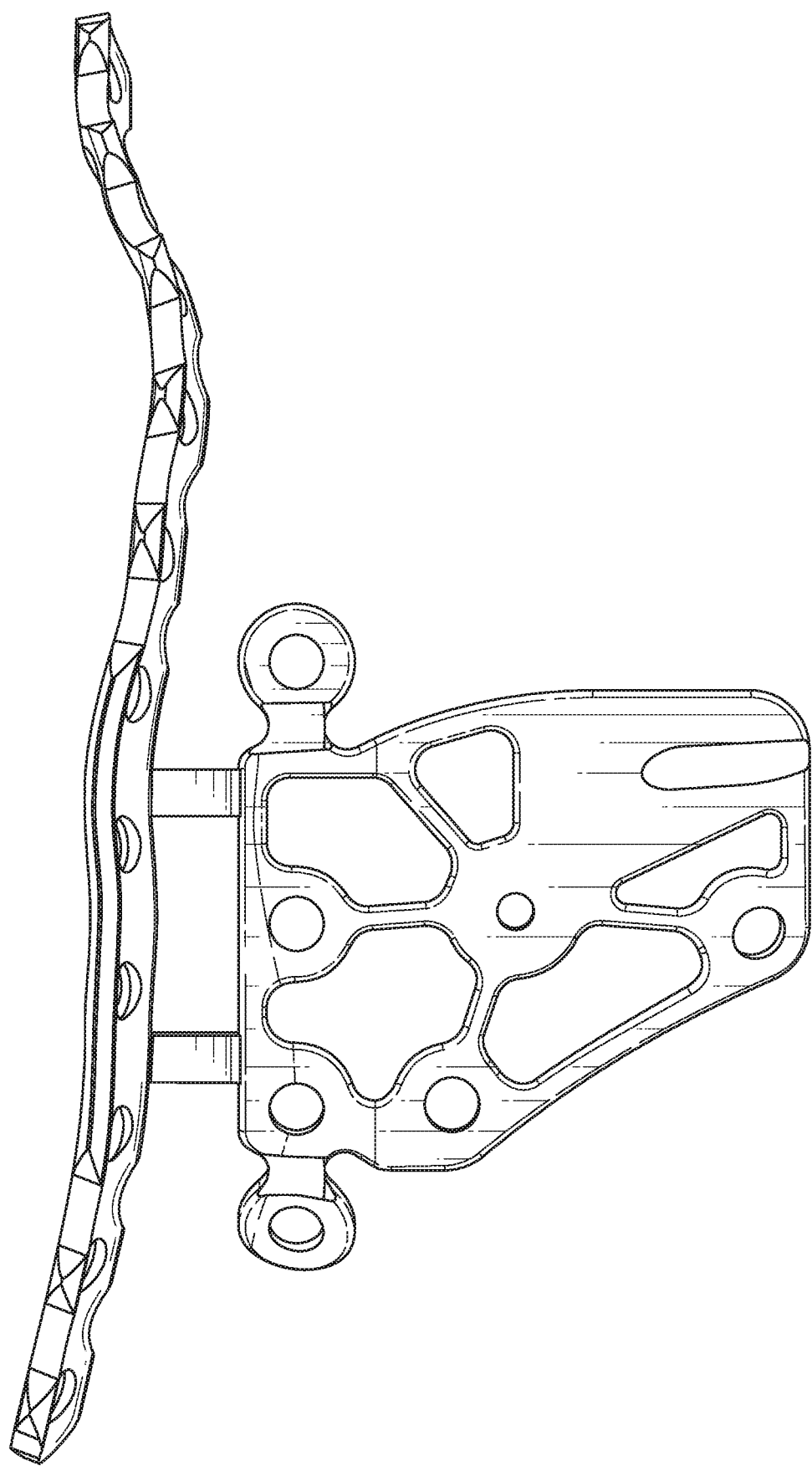
FIG. 10C is a rear perspective view of the bone plating system of the present disclosure as shown in FIG. 10A.
Figure 10D:
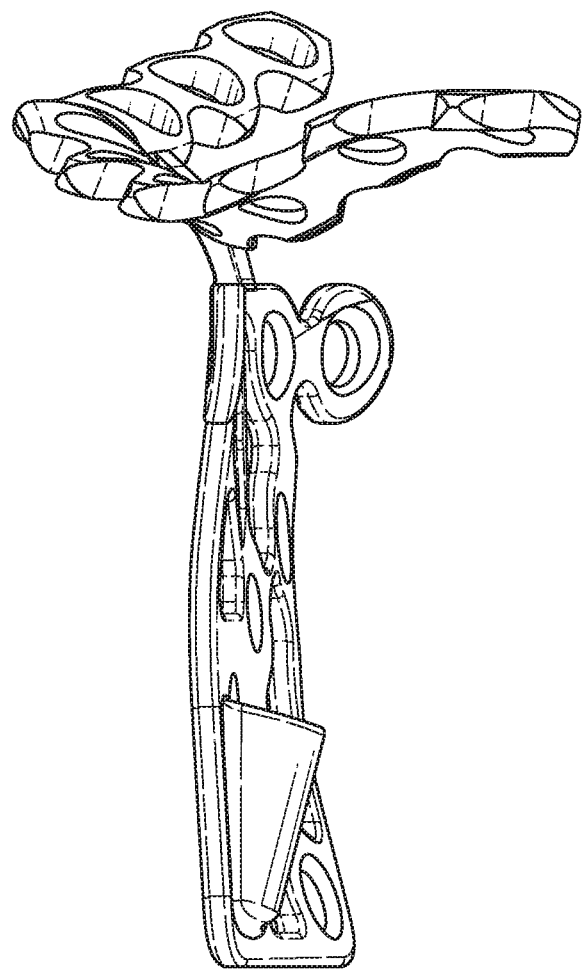
FIG. 10D is a first side perspective view of the bone plating system of the present disclosure as shown in FIG. 10A.
Figure 10E:
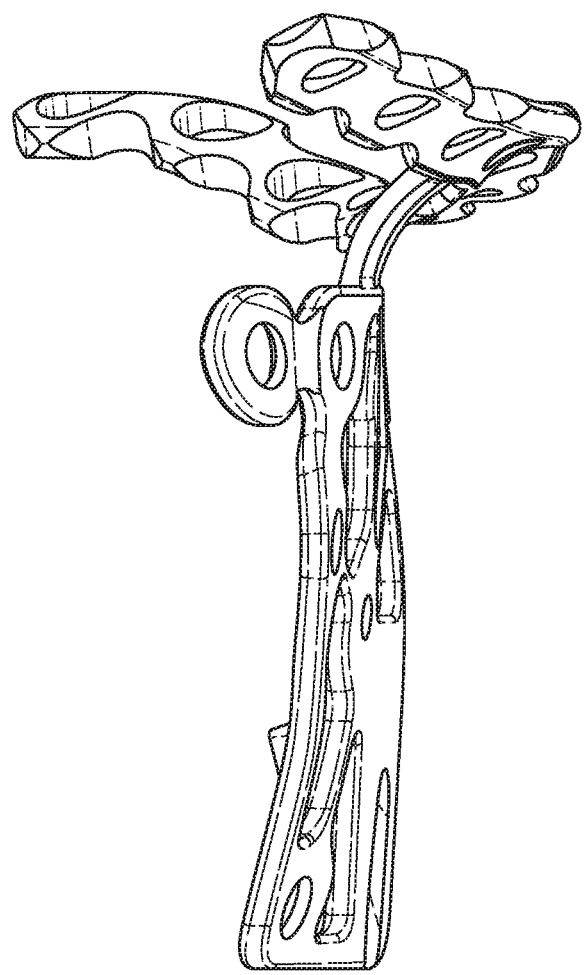
FIG. 10E is a second side perspective view of the bone plating system of the present disclosure as shown in FIG. 10A.
Figure 10F:
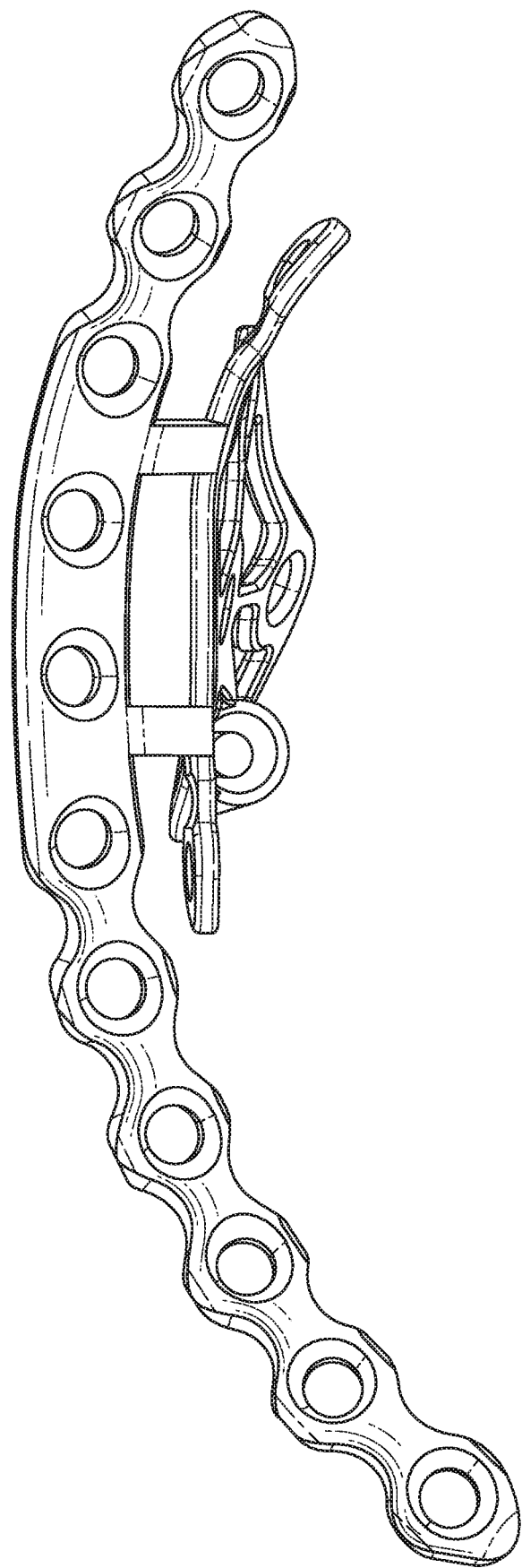
FIG. 10F is a top perspective view of the bone plating system of the present disclosure as shown in FIG. 10A.
Figure 10G:
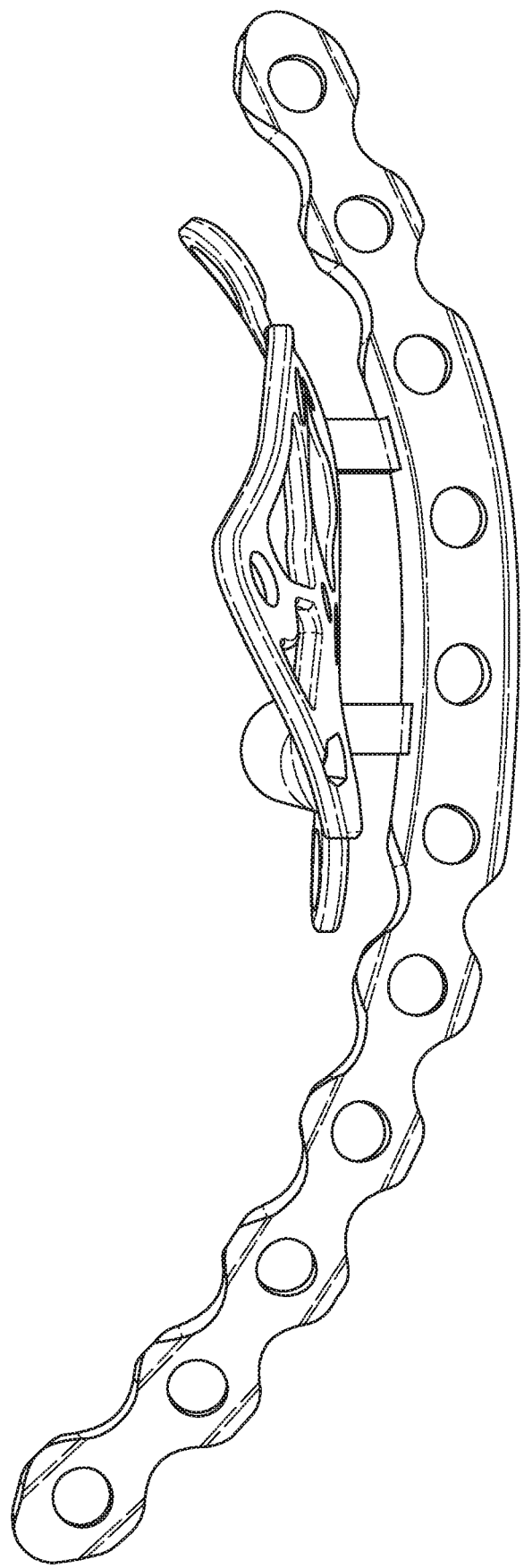
FIG. 10G is a bottom perspective view of the bone plating system of the present disclosure as shown in FIG. 10A.
Figure 11A:
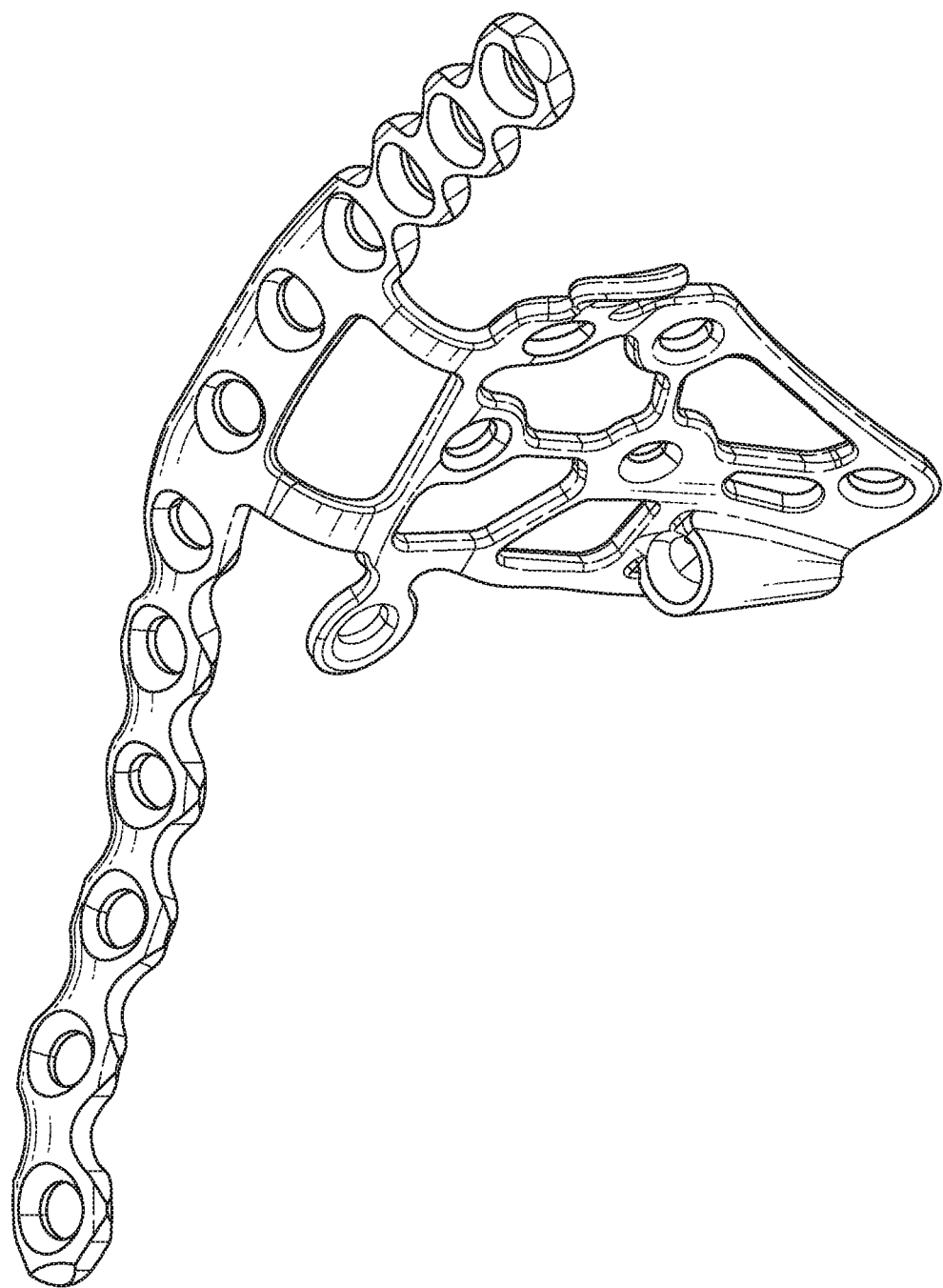
FIG. 11A is a perspective view of an alternative embodiment of a bone plating system of the present disclosure.
Figure 11B:
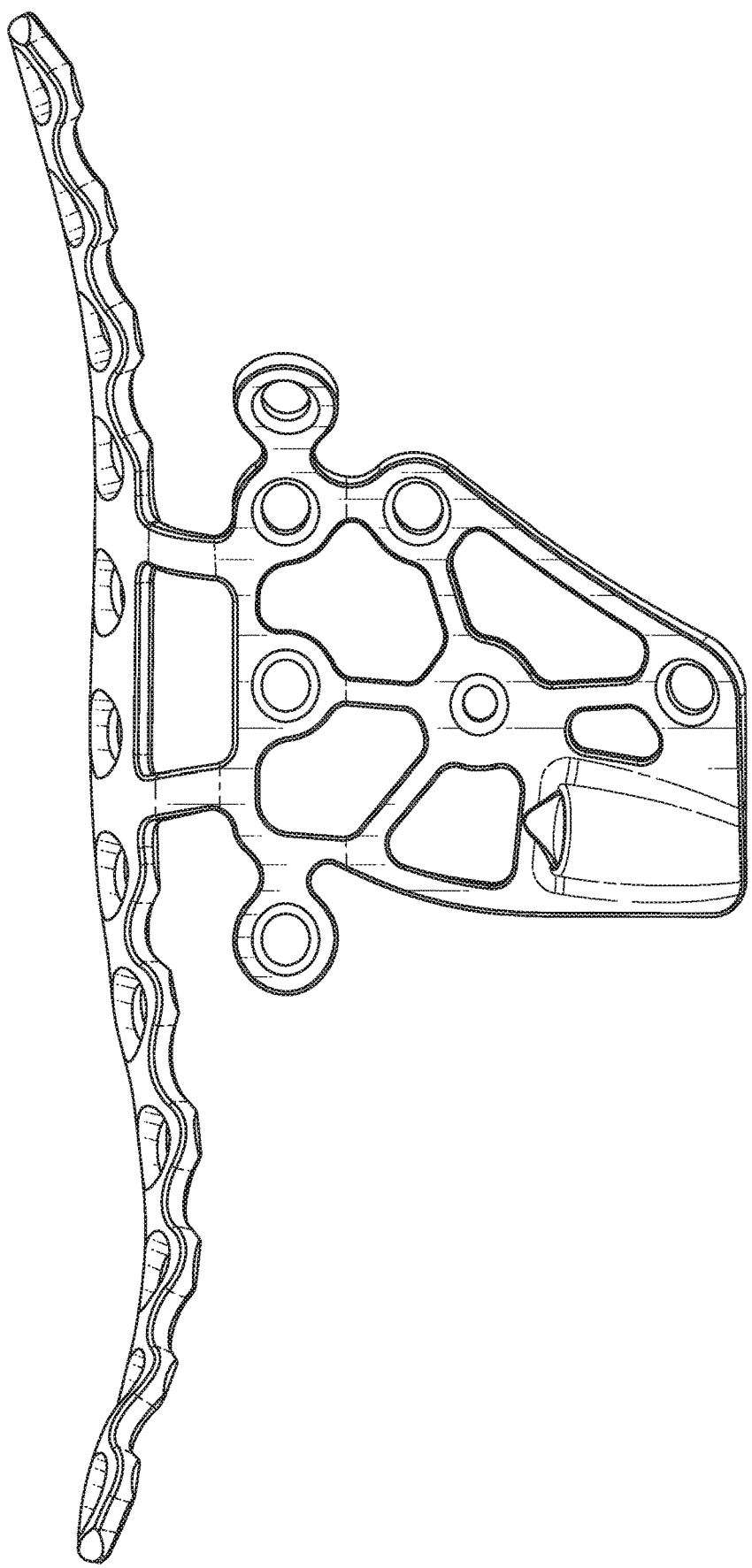
FIG. 11B is a front perspective view of the bone plating system of the present disclosure as shown in FIG. 11A.
Figure 11C:
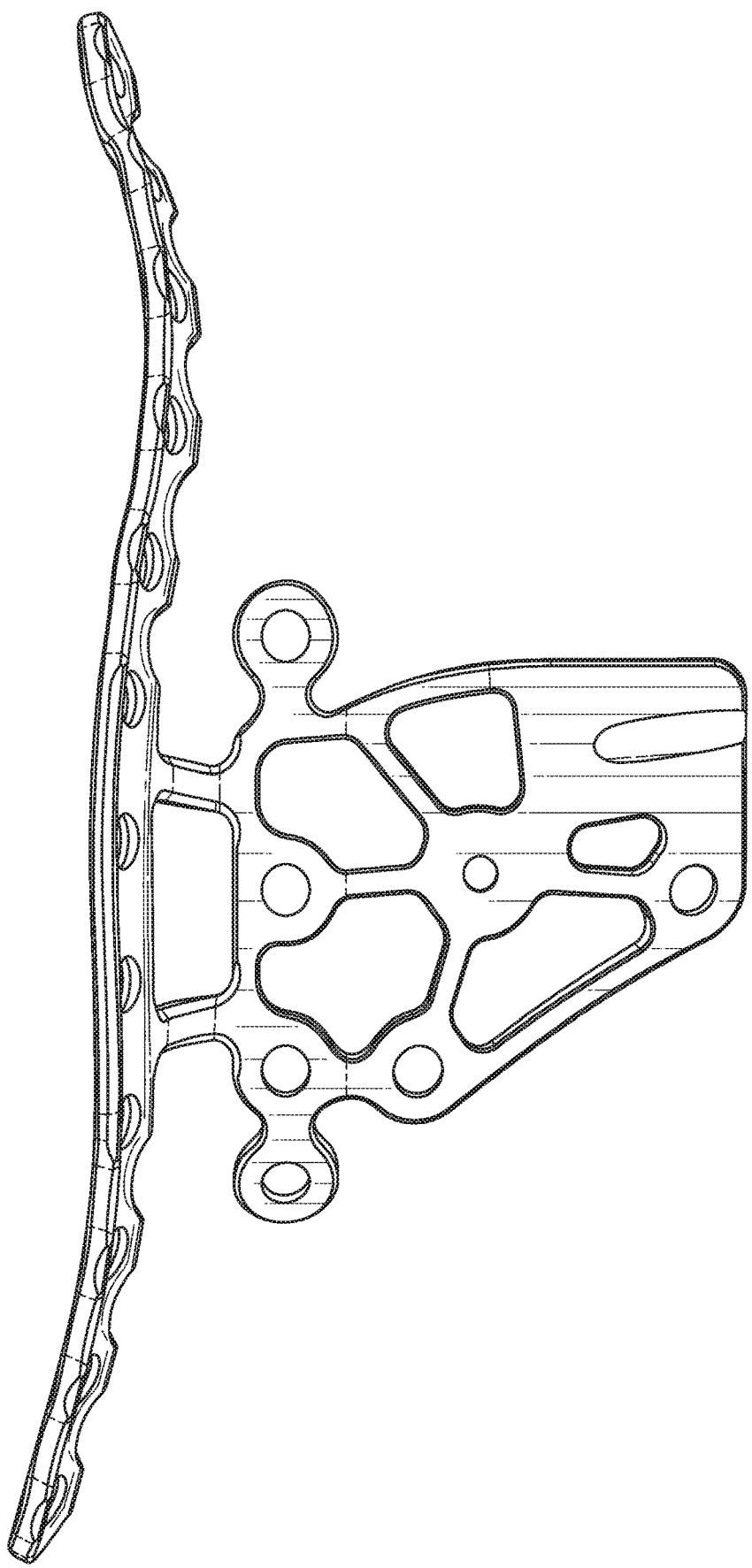
FIG. 11C is a rear perspective view of the bone plating system of the present disclosure as shown in FIG. 11A.
Figure 11D:
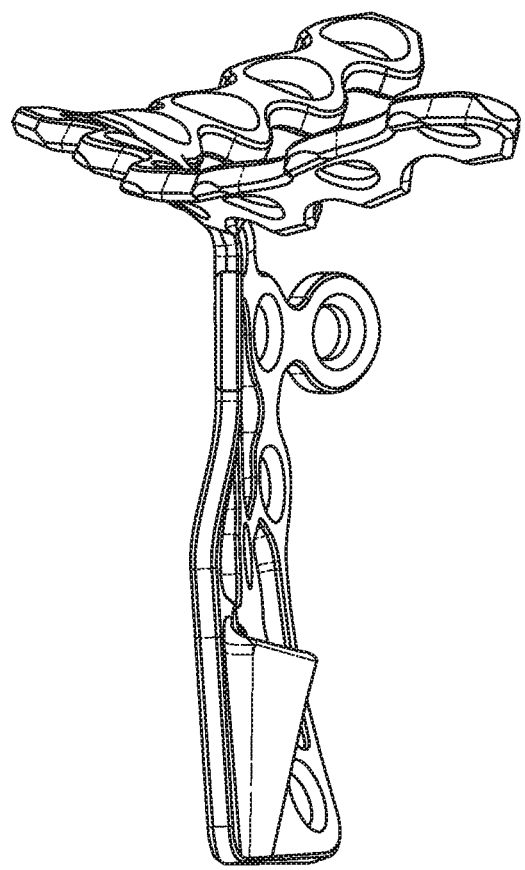
FIG. 11D is a first side perspective view of the bone plating system of the present disclosure as shown in FIG. 11A.
Figure 11E:
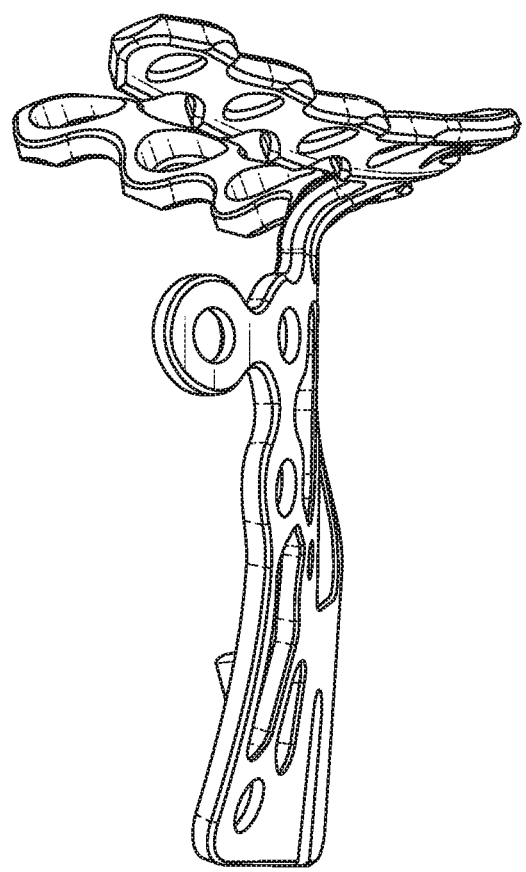
FIG. 11E is a second side perspective view of the bone plating system of the present disclosure as shown in FIG. 11A.
Figure 11F:
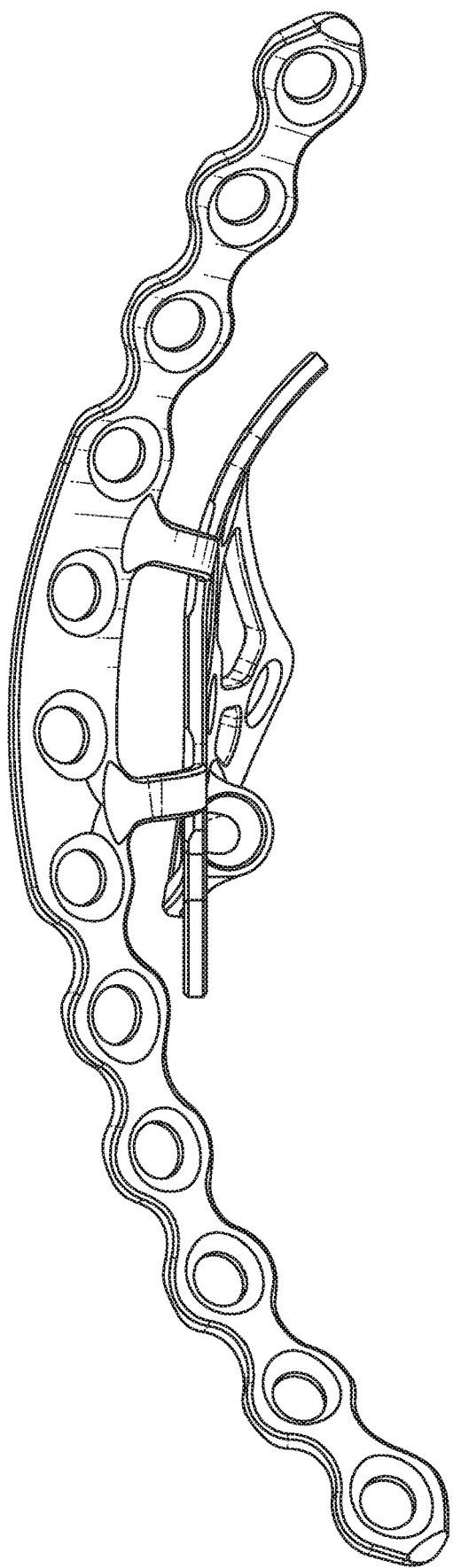
FIG. 11F is a top perspective view of the bone plating system of the present disclosure as shown in FIG. 11A.
Figure 11G:
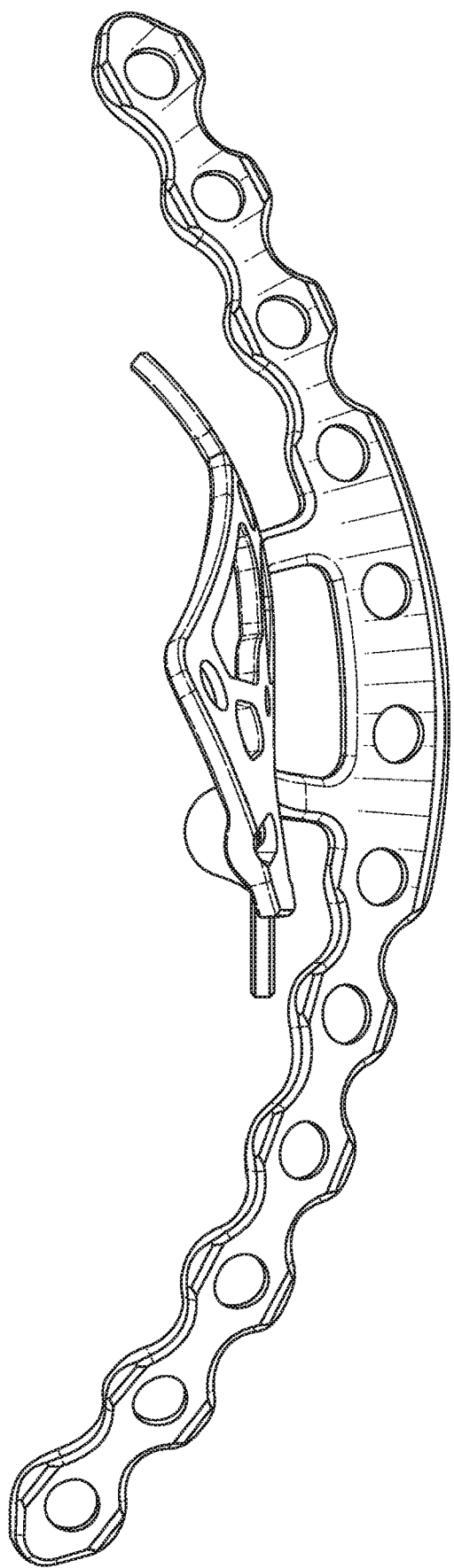
FIG. 11G is a bottom perspective view of the bone plating system of the present disclosure as shown in FIG. 11A.
Figure 12A:
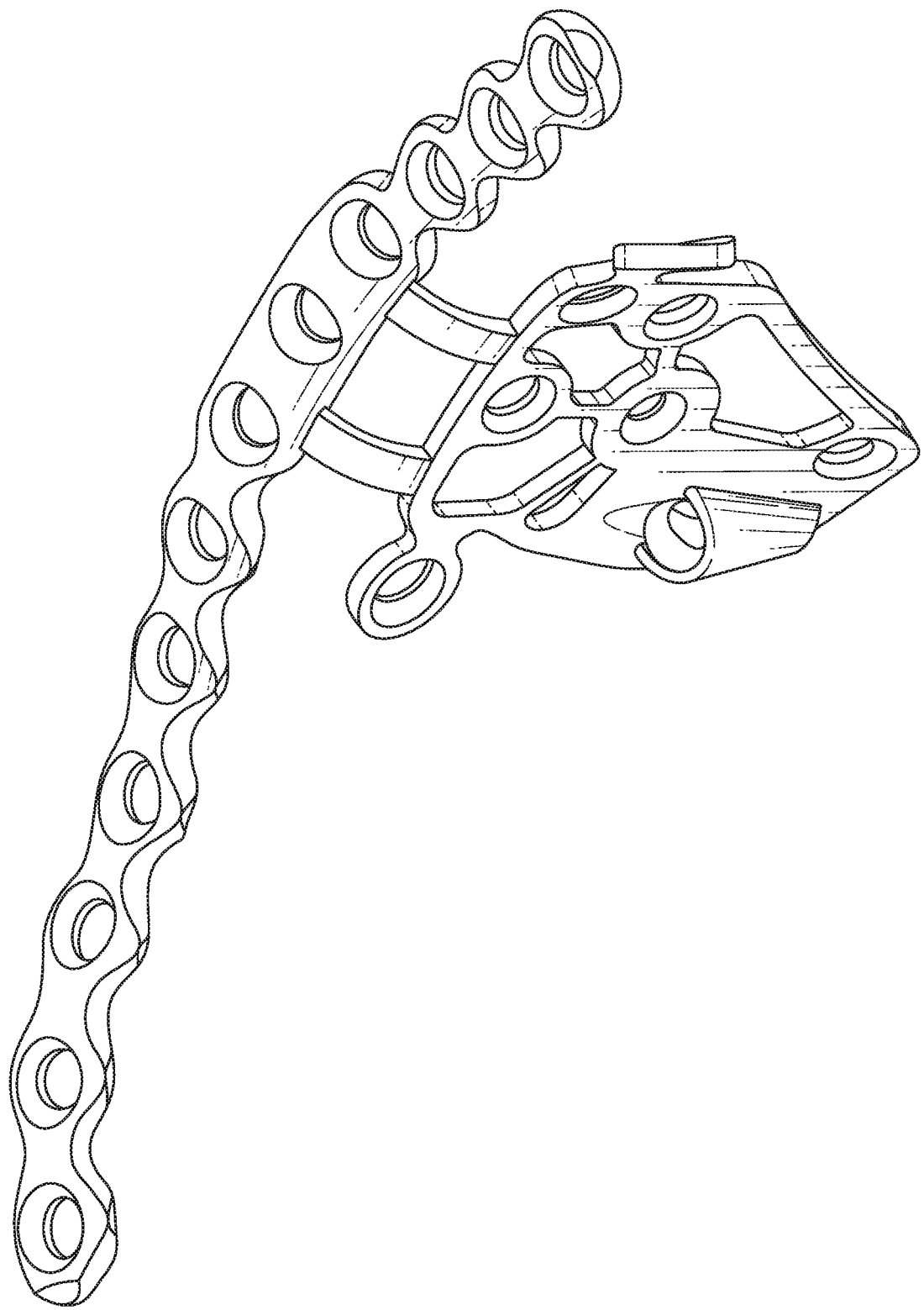
FIG. 12A is a perspective view of an alternative embodiment of a bone plating system of the present disclosure.
Figure 12B:
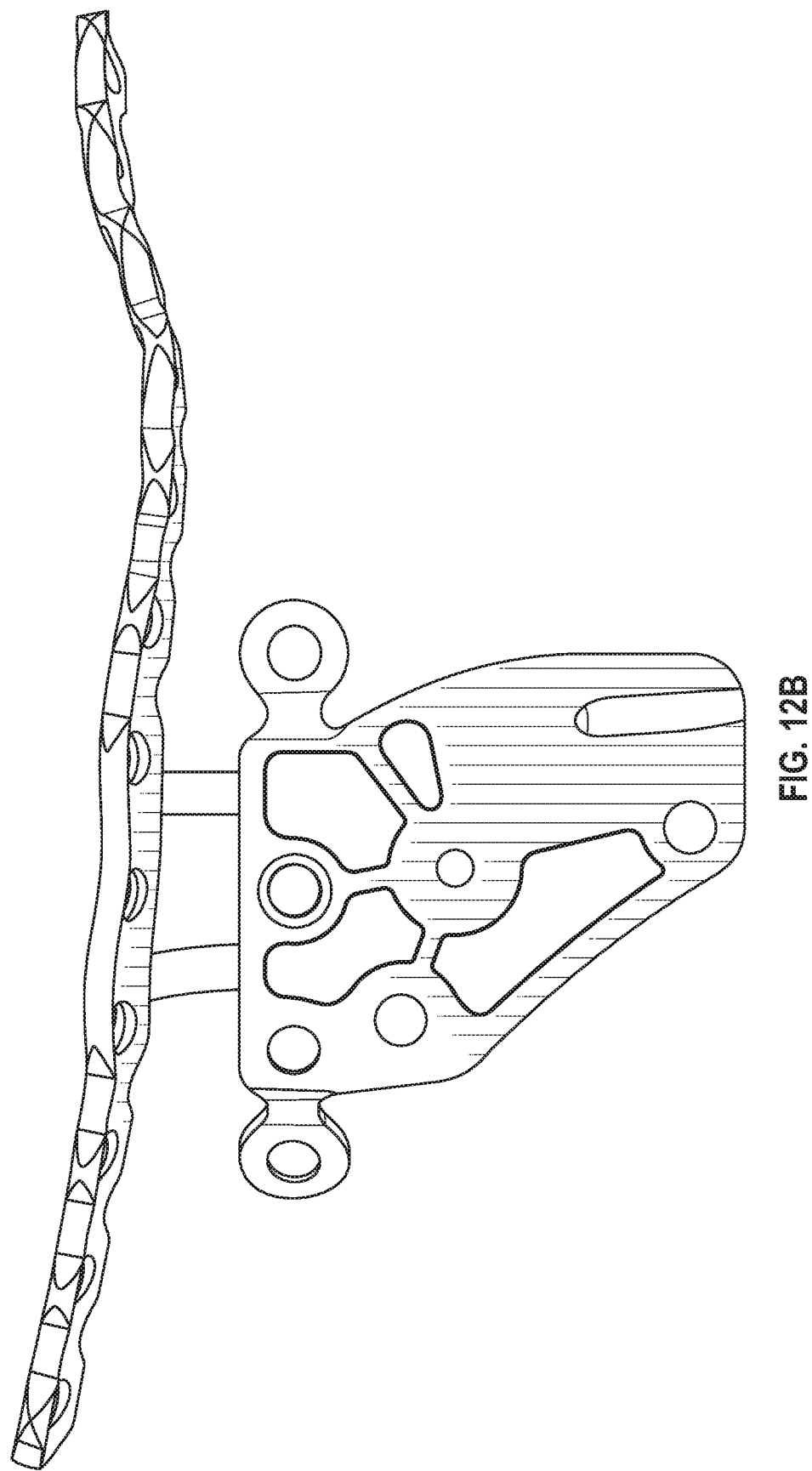
FIG. 12B is a rear perspective view of the bone plating system of the present disclosure as shown in FIG. 12A.
Figure 12C:
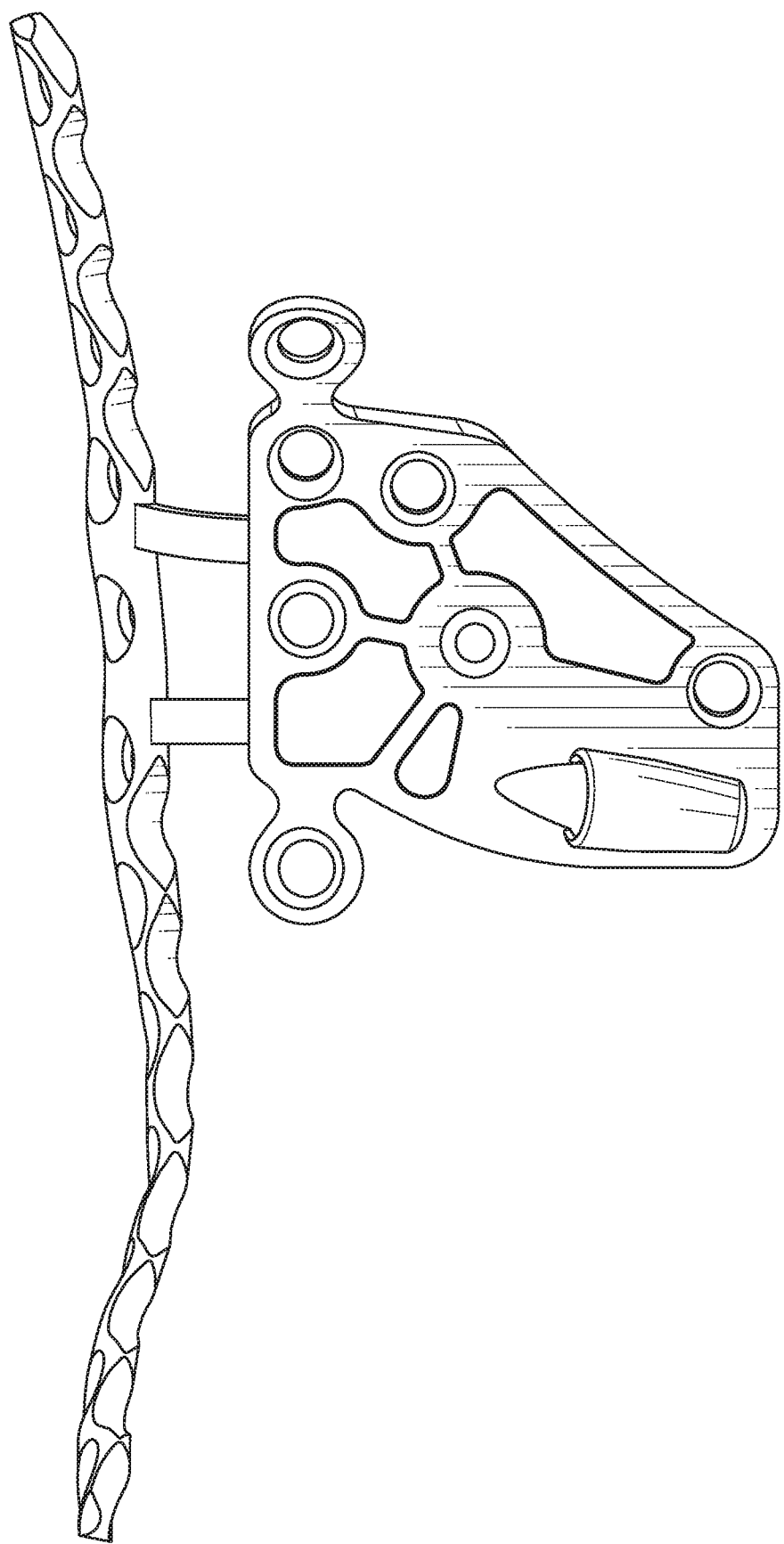
FIG. 12C is a front perspective view of the bone plating system of the present disclosure as shown in FIG. 12A.
Figure 12D:
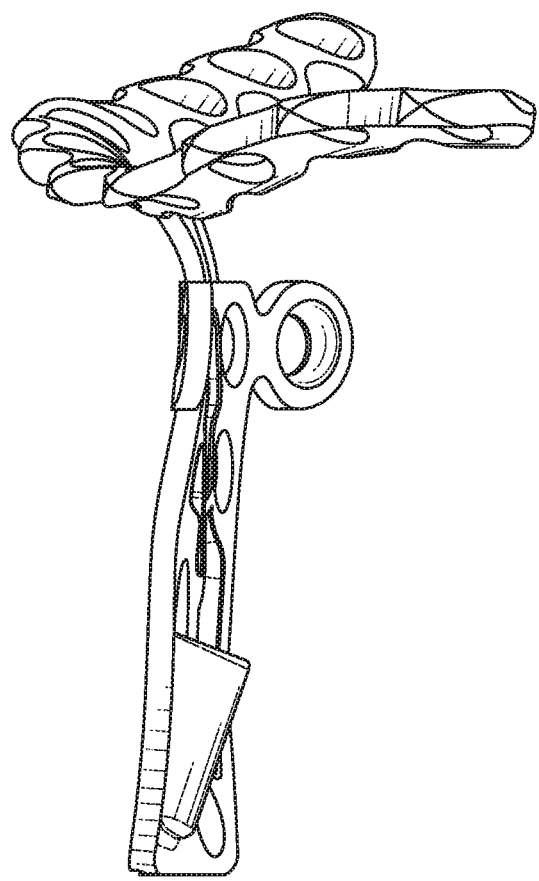
FIG. 12D is a first side perspective view of the bone plating system of the present disclosure as shown in FIG. 12A.
Figure 12E:
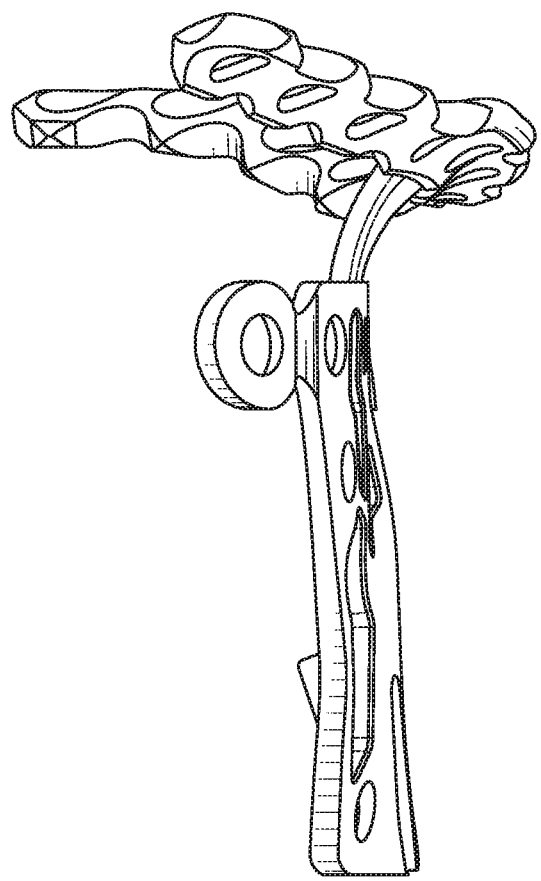
FIG. 12E is a second side perspective view of the bone plating system of the present disclosure as shown in FIG. 12A.
Figure 12F:
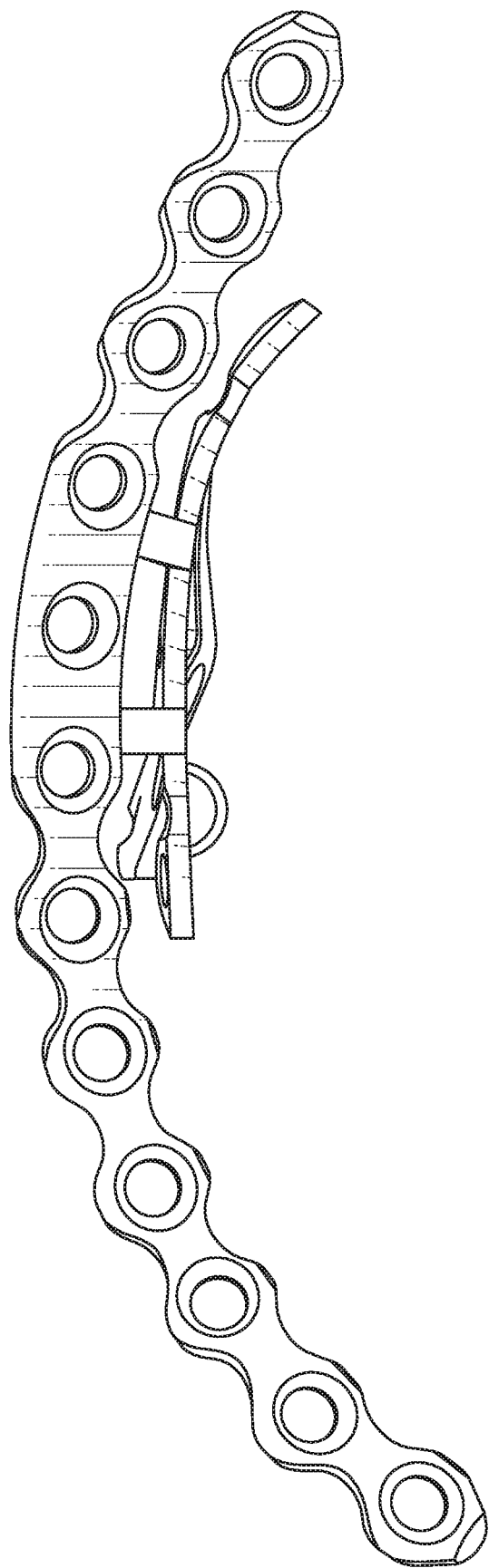
FIG. 12F is a top perspective view of the bone plating system of the present disclosure as shown in FIG. 12A.
Figure 12G:
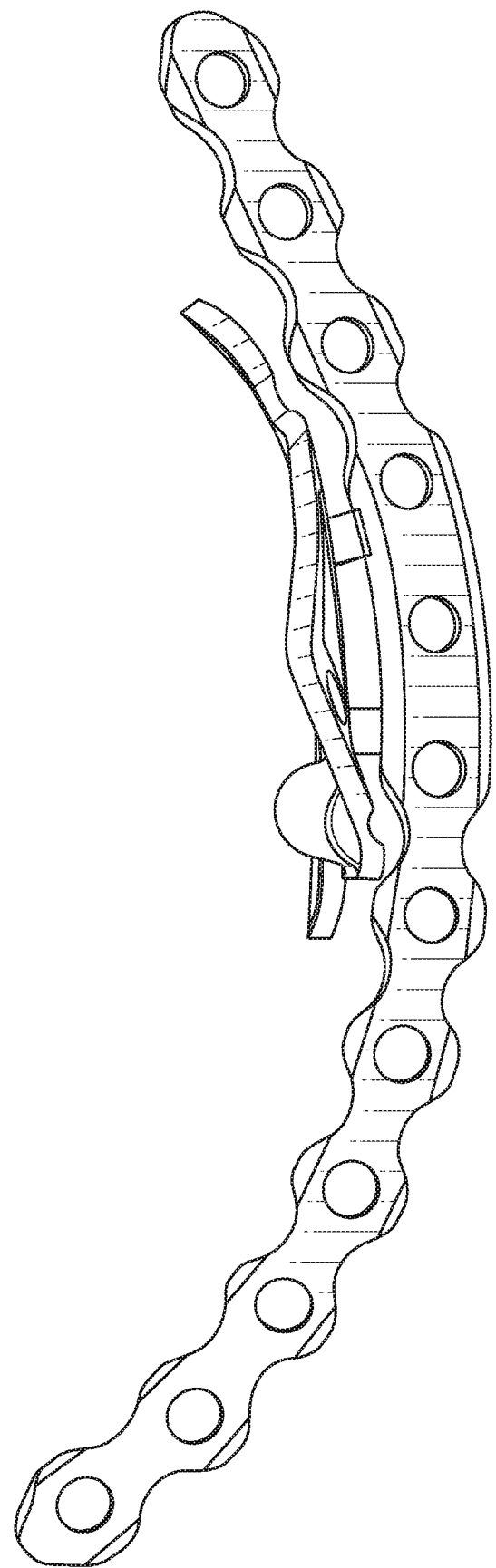
FIG. 12G is a bottom perspective view of the bone plating system of the present disclosure as shown in FIG. 12A.
Figure 13A:
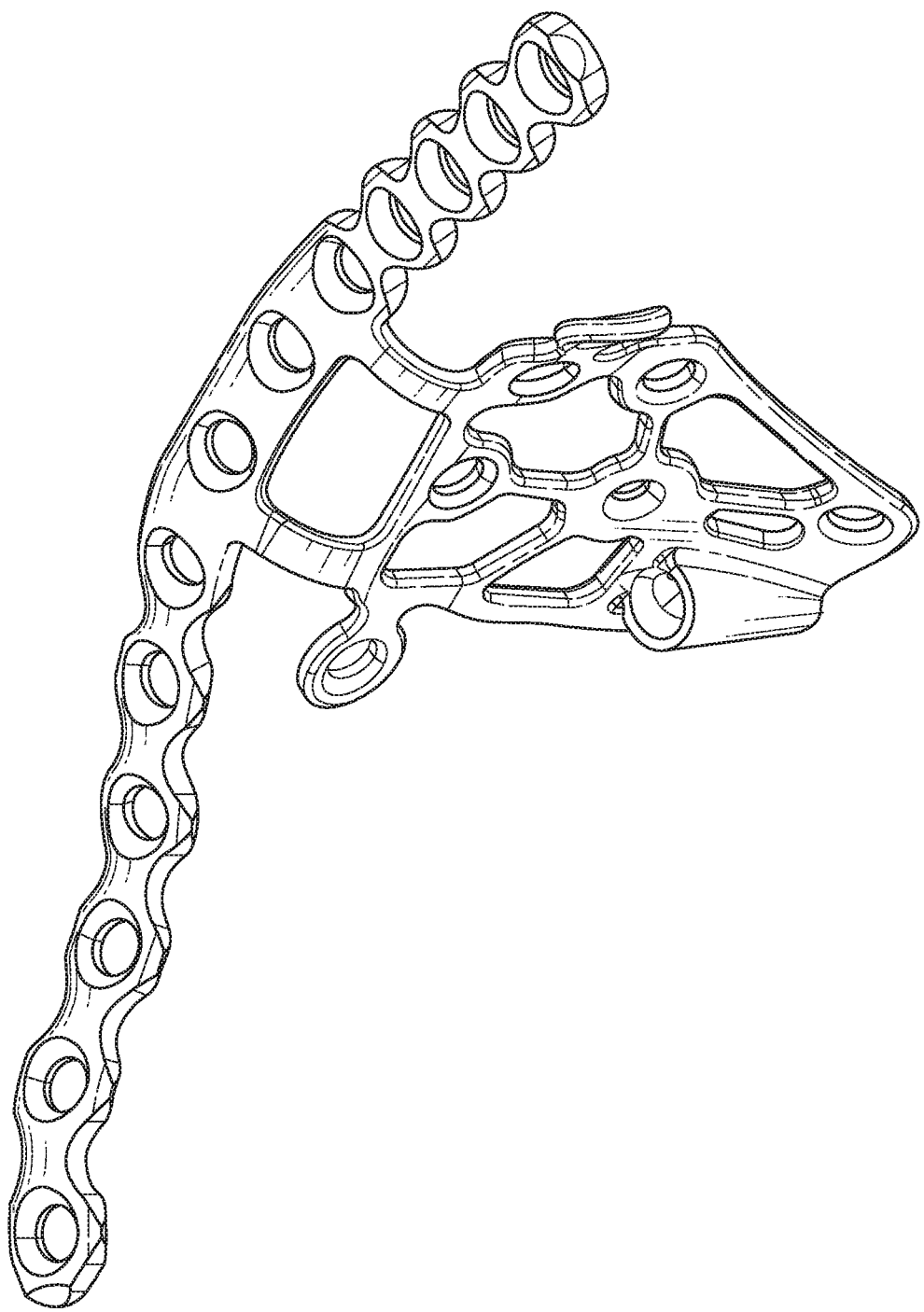
FIG. 13A is a perspective view of an alternative embodiment of a bone plating system of the present disclosure.
Figure 13B:
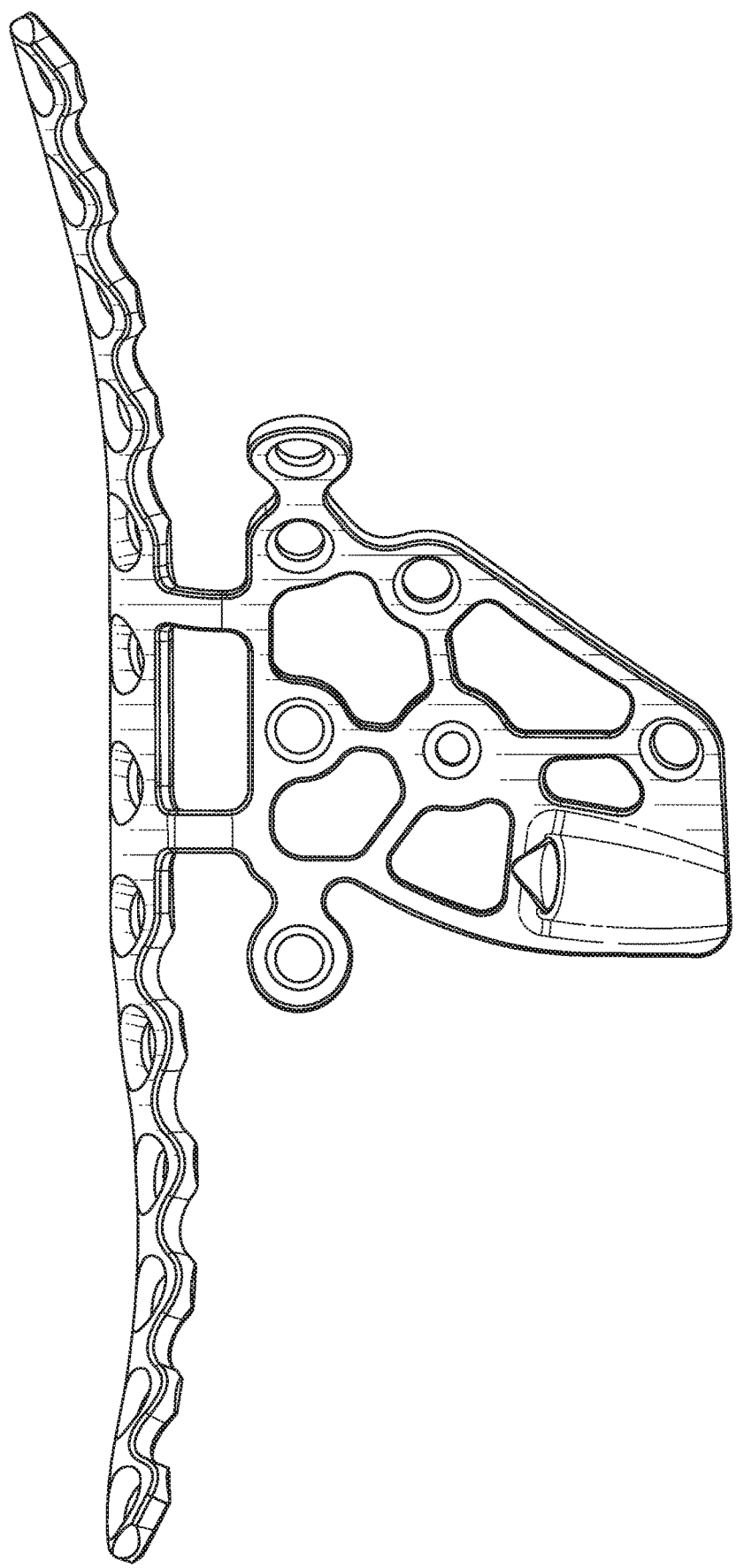
FIG. 13B is a front perspective view of the bone plating system of the present disclosure as shown in FIG. 13A.
Figure 13C:
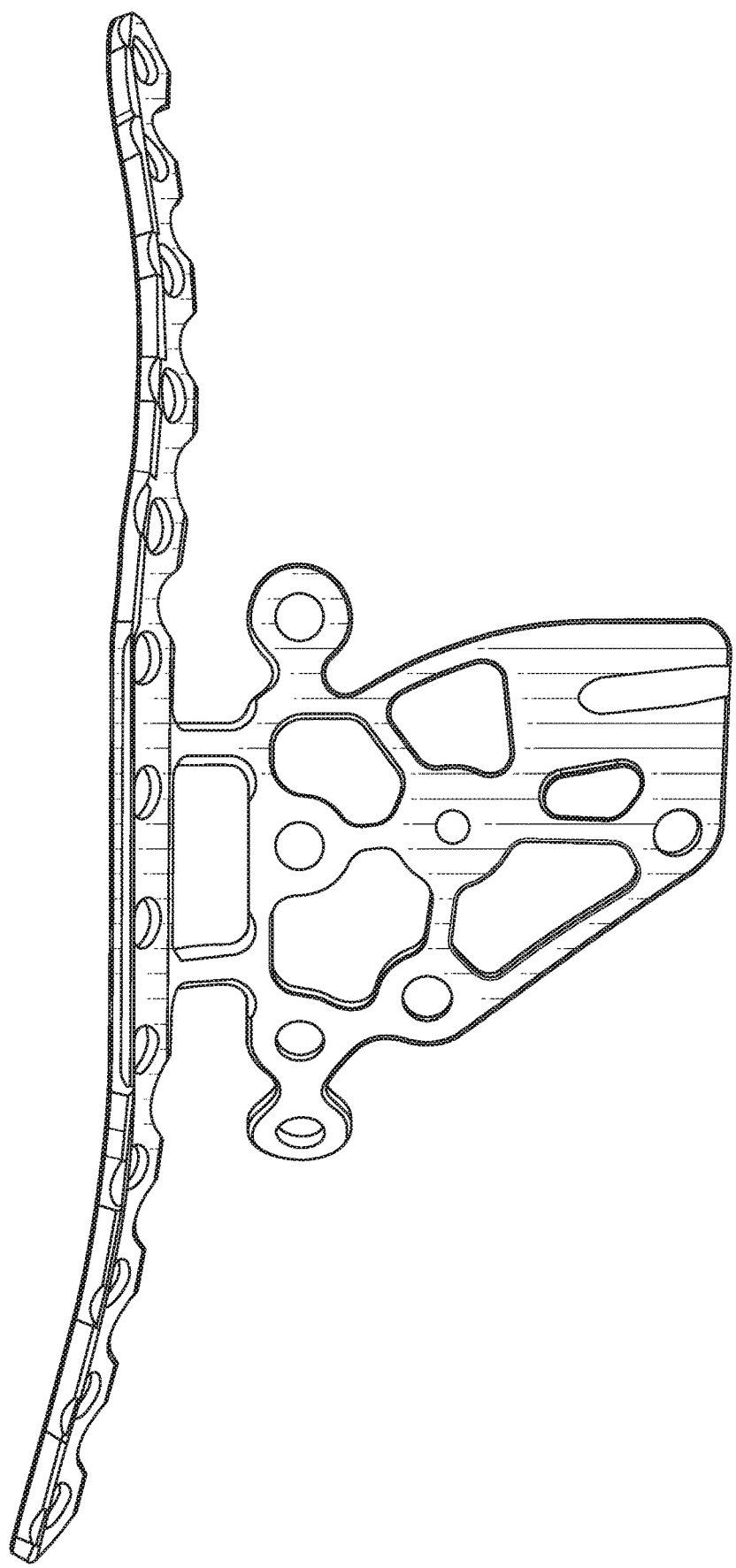
FIG. 13C is a rear perspective view of the bone plating system of the present disclosure as shown in FIG. 13A.
Figure 13D:
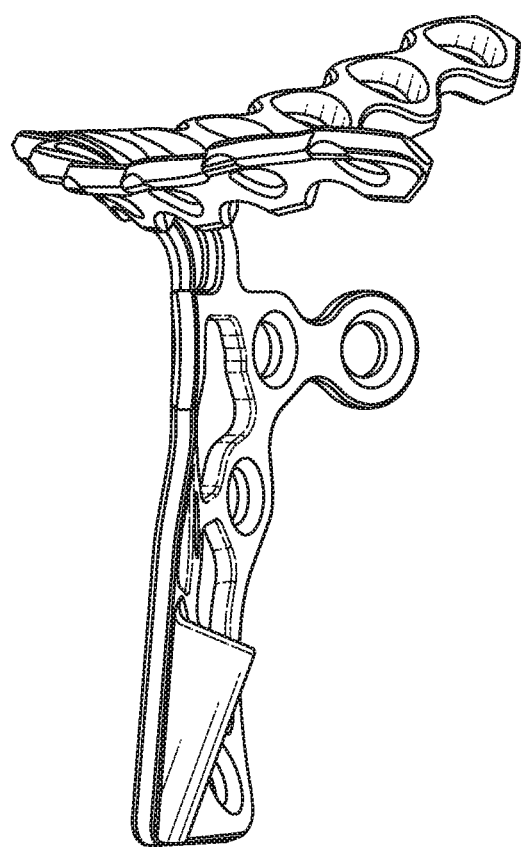
FIG. 13D is a first side perspective view of the bone plating system of the present disclosure as shown in FIG. 13A.
Figure 13E:
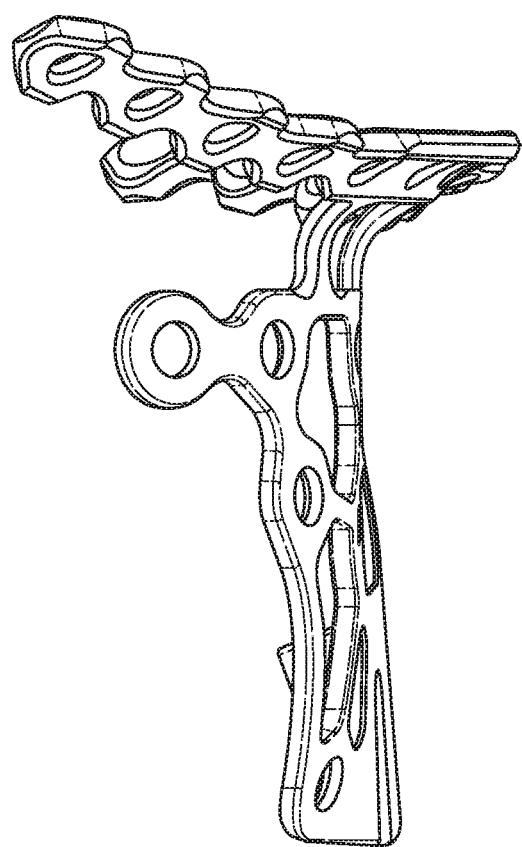
FIG. 13E is a second side perspective view of the bone plating system of the present disclosure as shown in FIG. 13A.
Figure 13F:
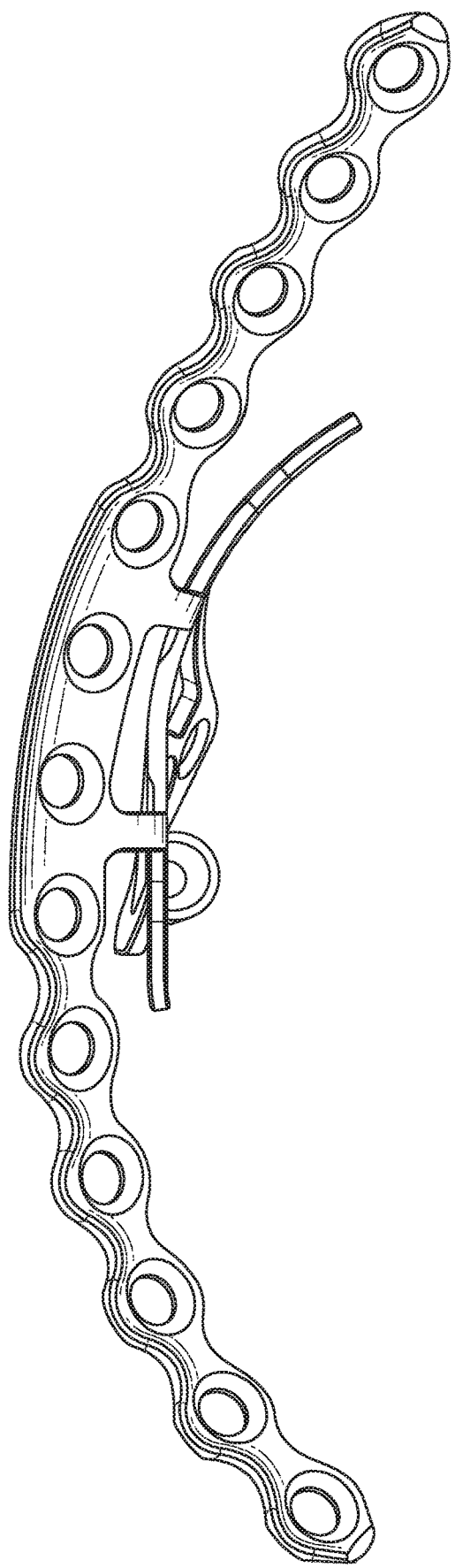
FIG. 13F is a top perspective view of the bone plating system of the present disclosure as shown in FIG. 13A.
Figure 13G:
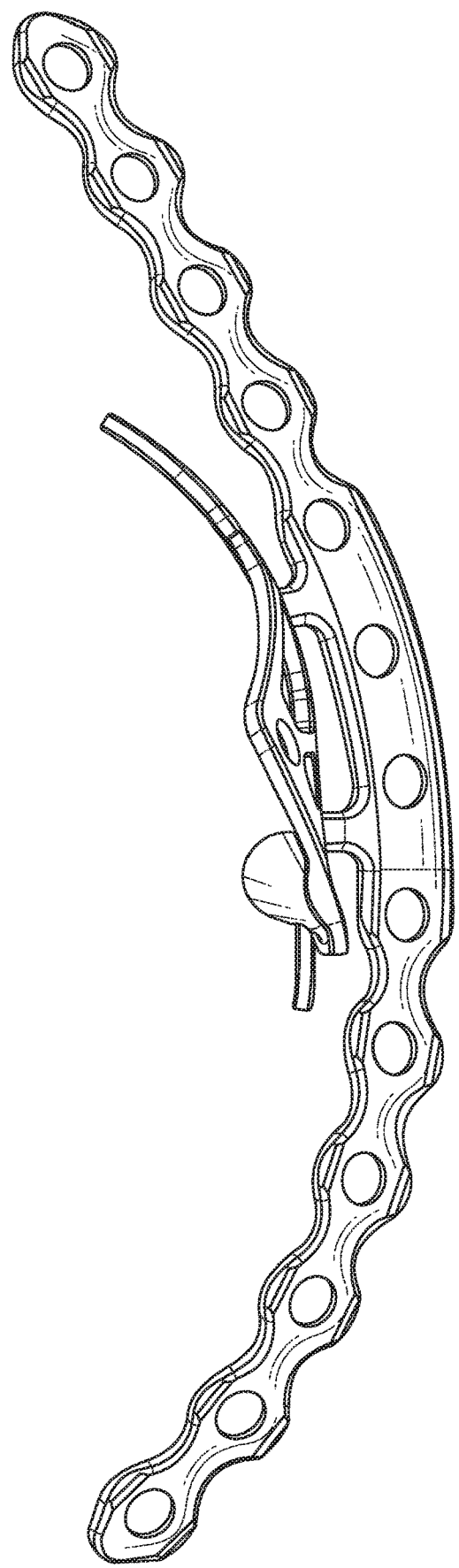
FIG. 13G is a bottom perspective view of the bone plating system of the present disclosure as shown in FIG. 13A.
Figure 14A:
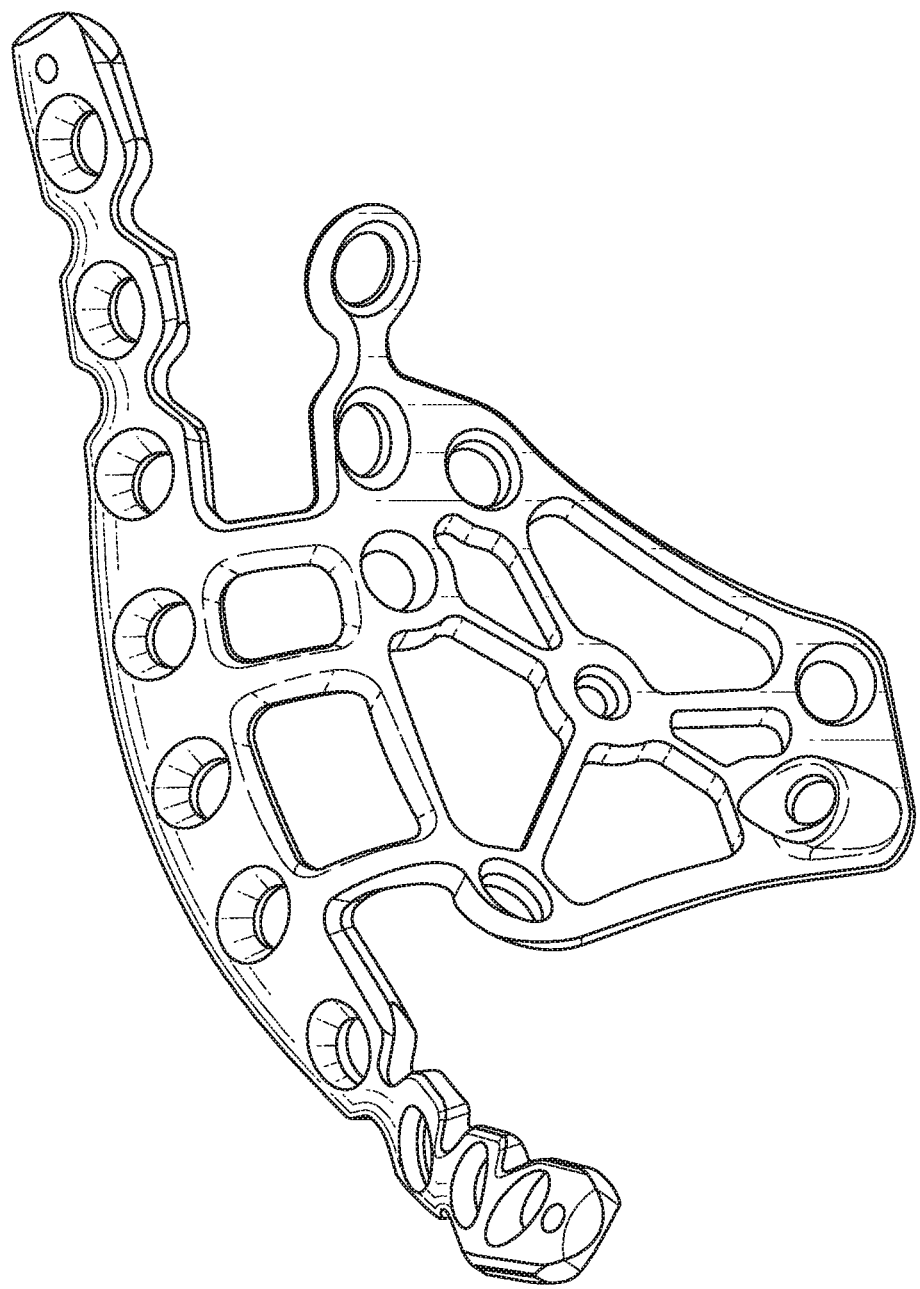
FIG. 14A is a perspective view of an alternative embodiment of a bone plating system of the present disclosure.
Figure 14B:
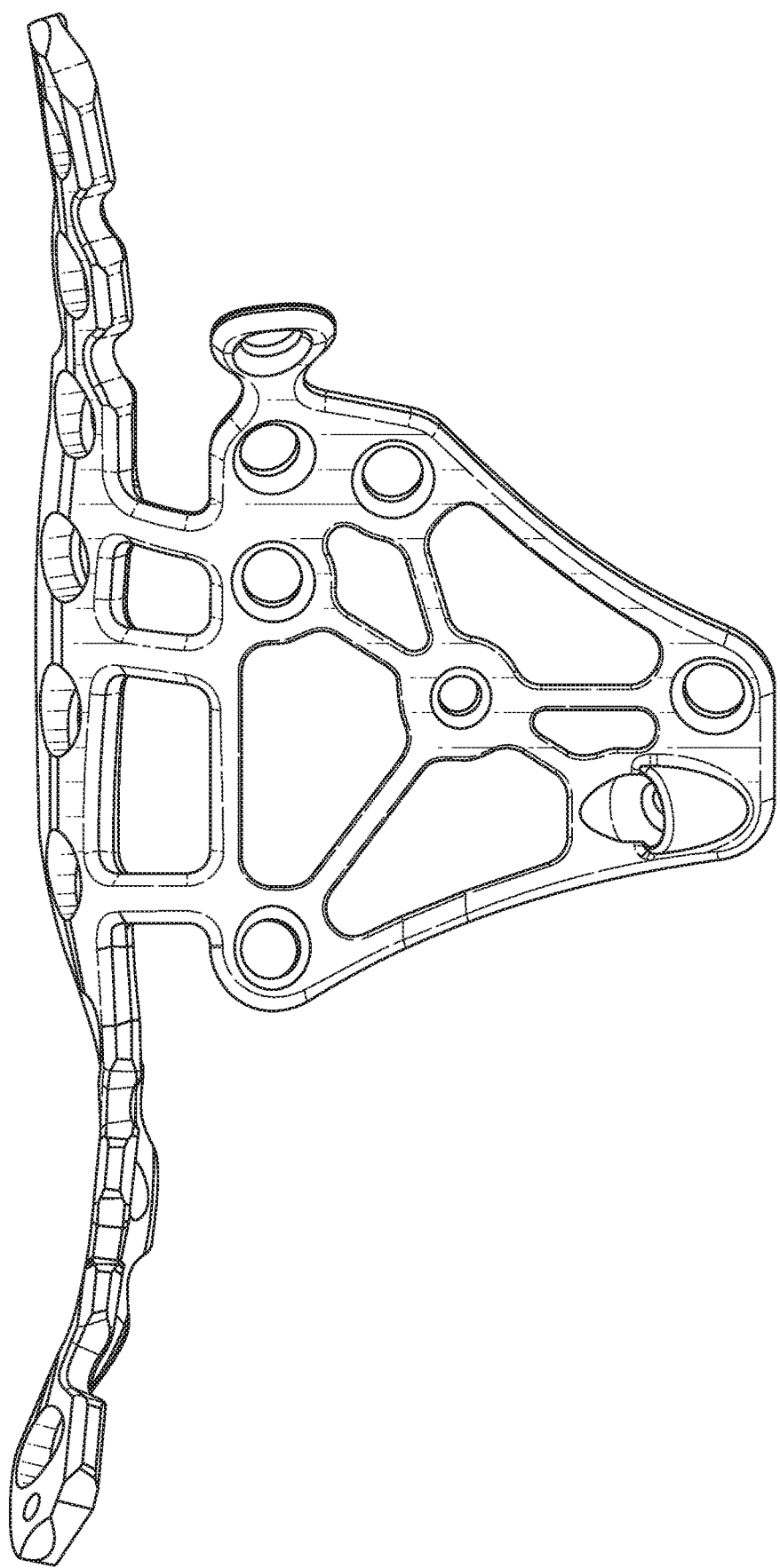
FIG. 14B is a front perspective view of the bone plating system of the present disclosure as shown in FIG. 14A.
Figure 14C:
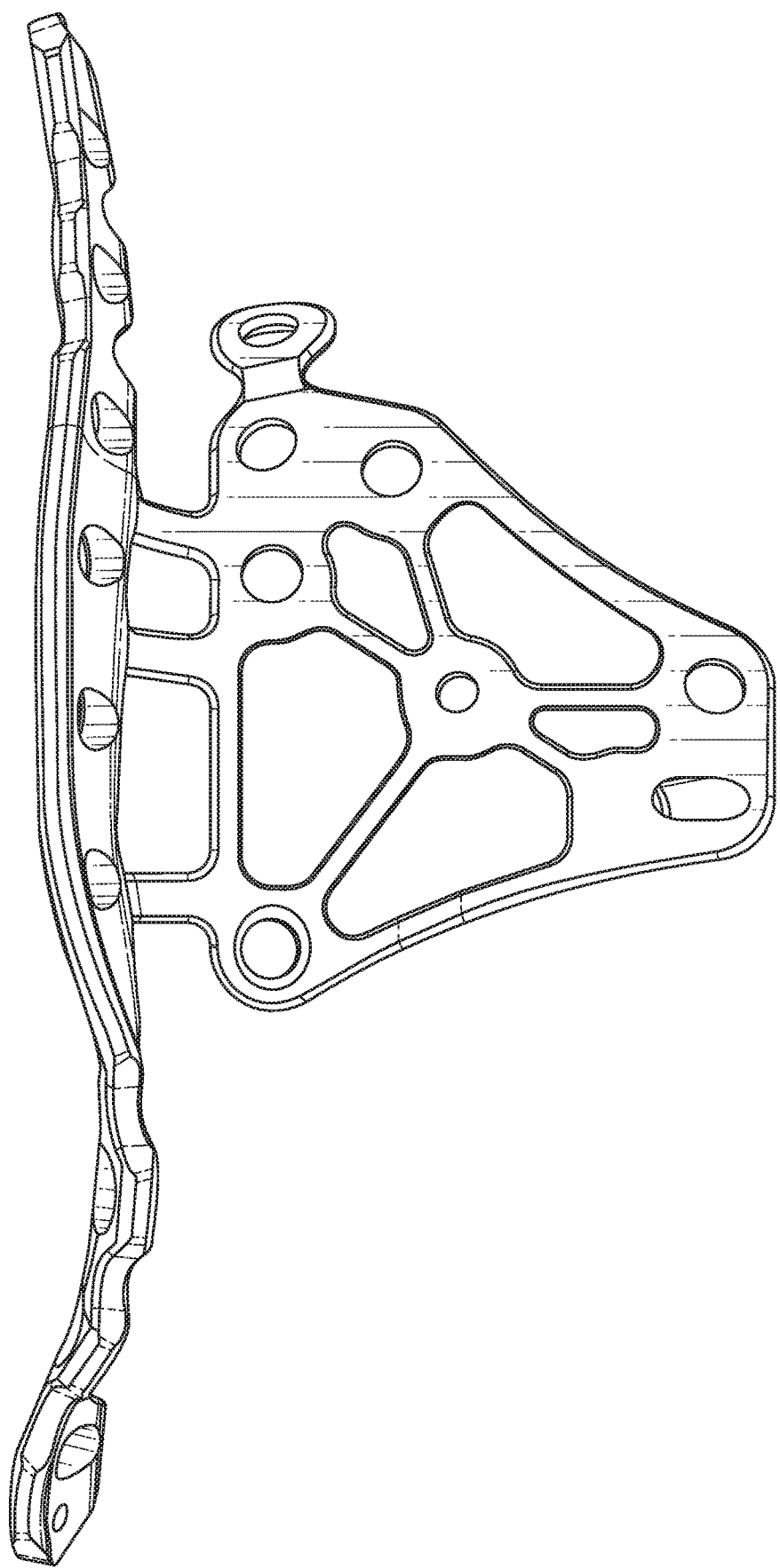
FIG. 14C is a rear perspective view of the bone plating system of the present disclosure as shown in FIG. 14A.
Figure 14D:
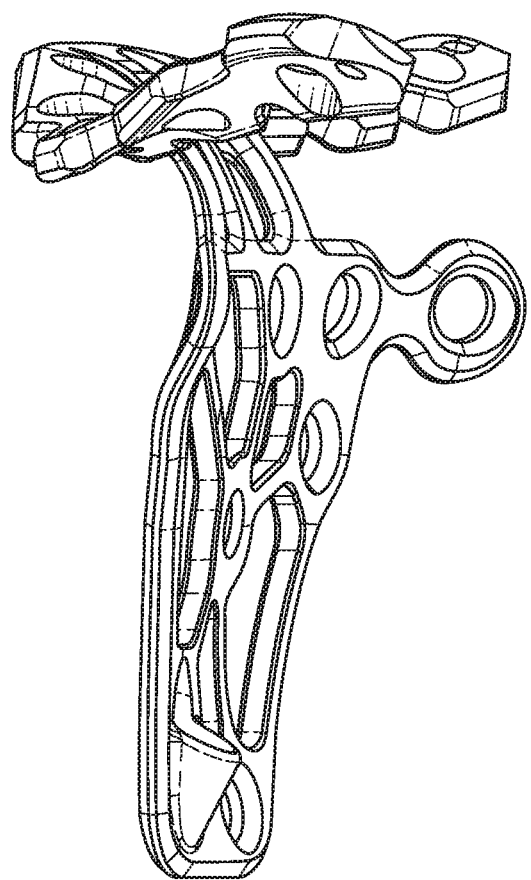
FIG. 14D is a first side perspective view of the bone plating system of the present disclosure as shown in FIG. 14A.
Figure 14E:
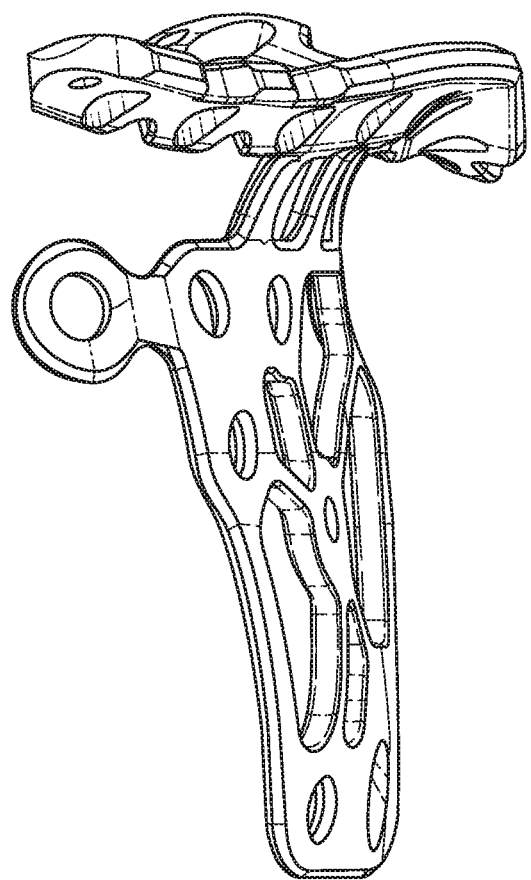
FIG. 14E is a second side perspective view of the bone plating system of the present disclosure as shown in FIG. 14A.
Figure 14F:
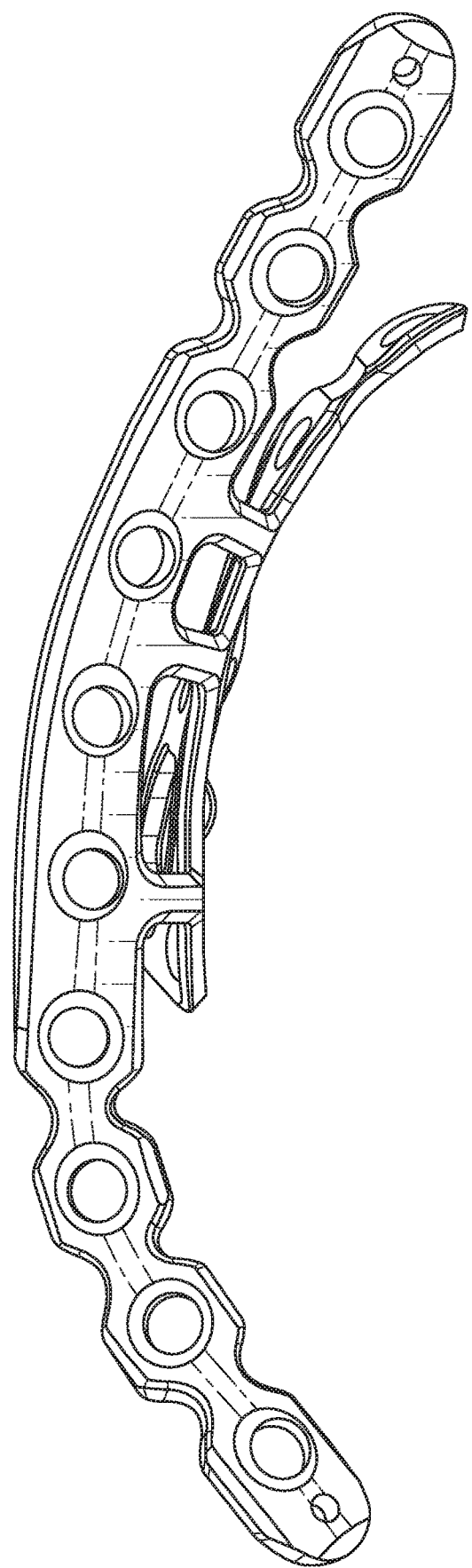
FIG. 14F is a top perspective view of the bone plating system of the present disclosure as shown in FIG. 14A.
Figure 14G:
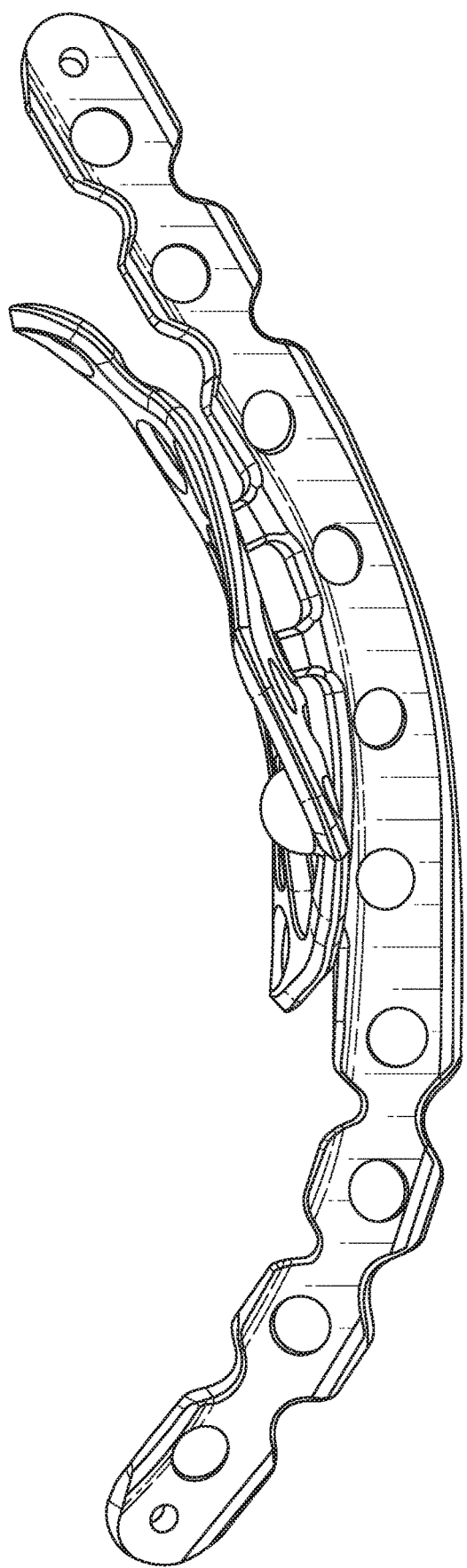
FIG. 14G is a bottom perspective view of the bone plating system of the present disclosure as shown in FIG. 14A.
Figure 15A:
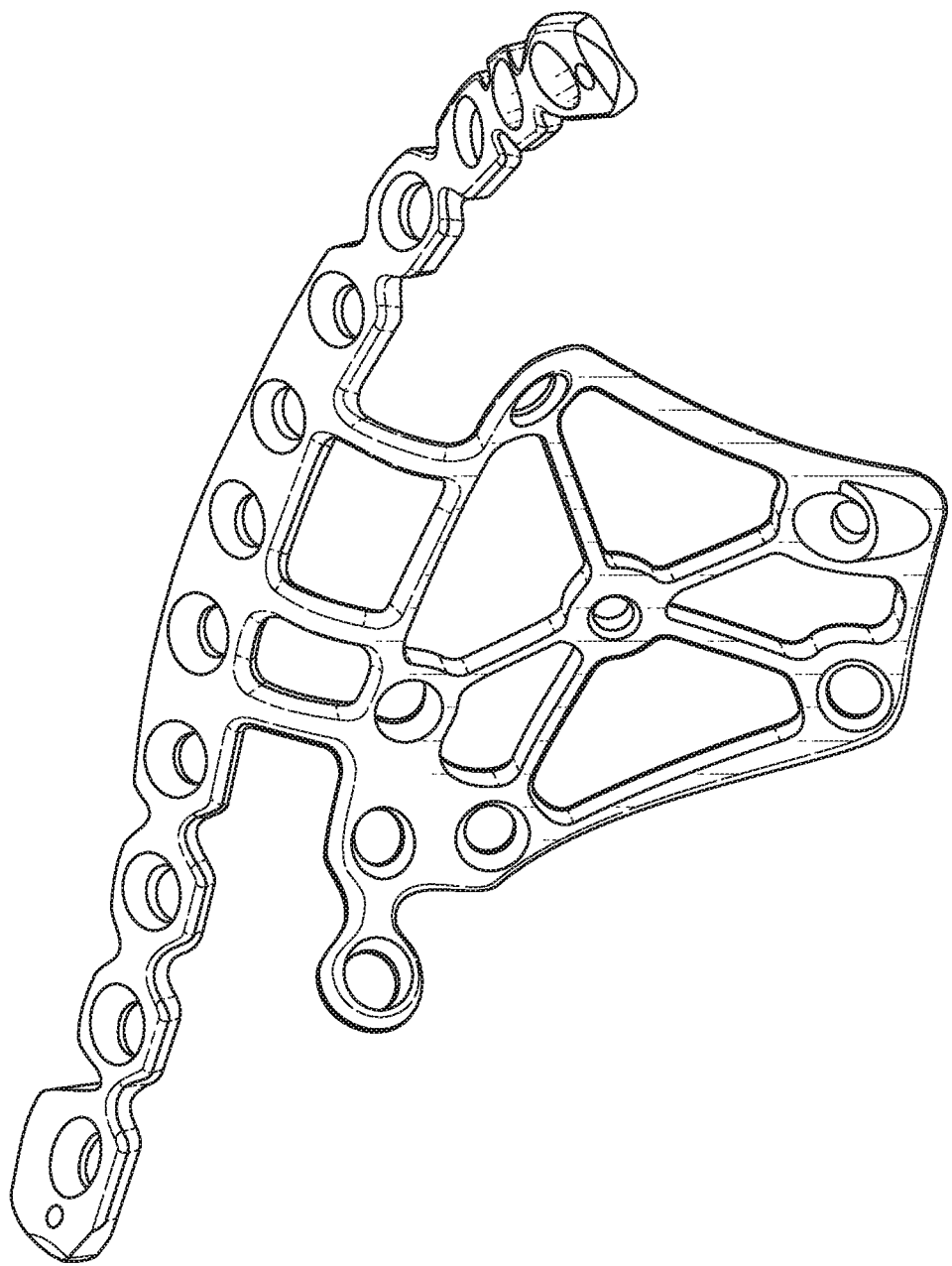
FIG. 15A is a perspective view of an alternative embodiment of a bone plating system of the present disclosure.
Figure 15B:
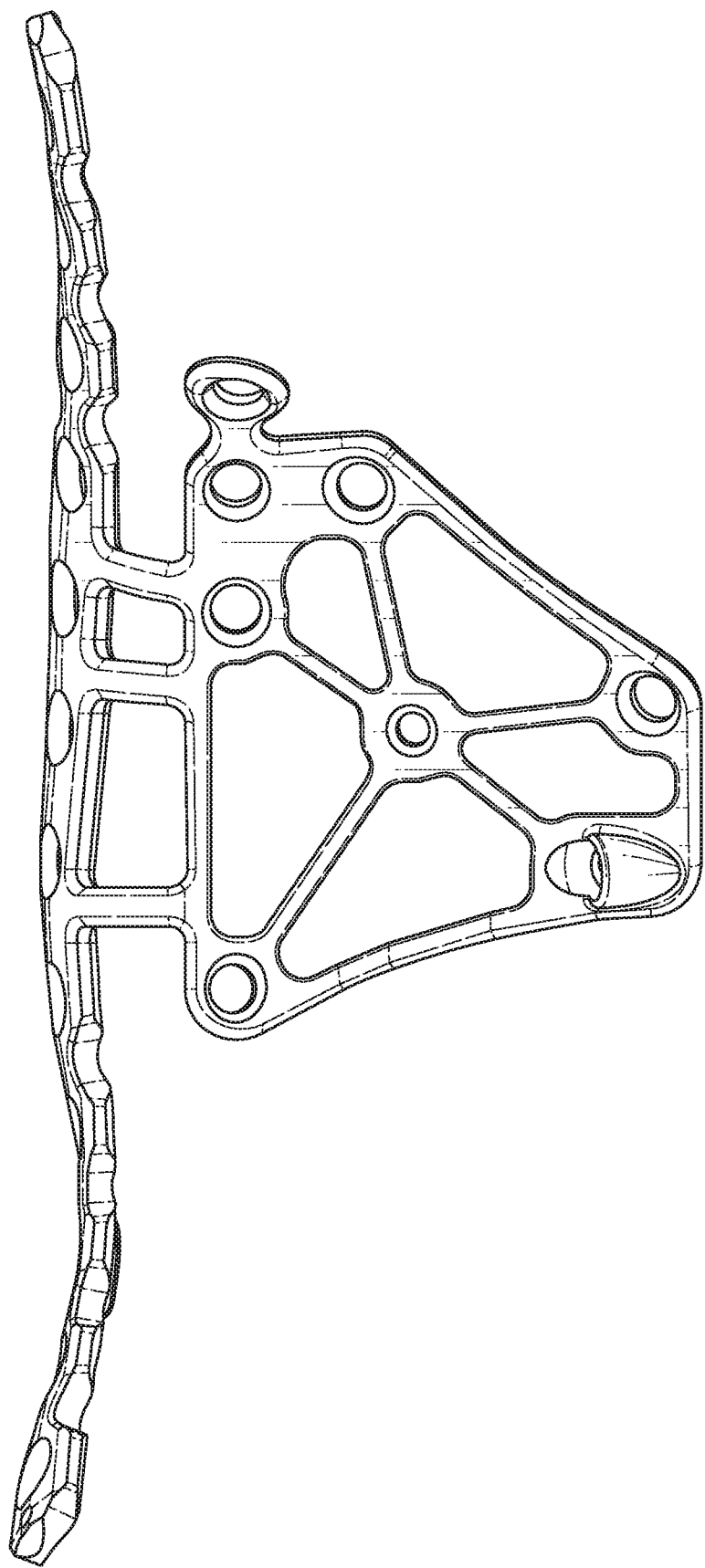
FIG. 15B is a front perspective view of the bone plating system of the present disclosure as shown in FIG. 15A.
Figure 15C:
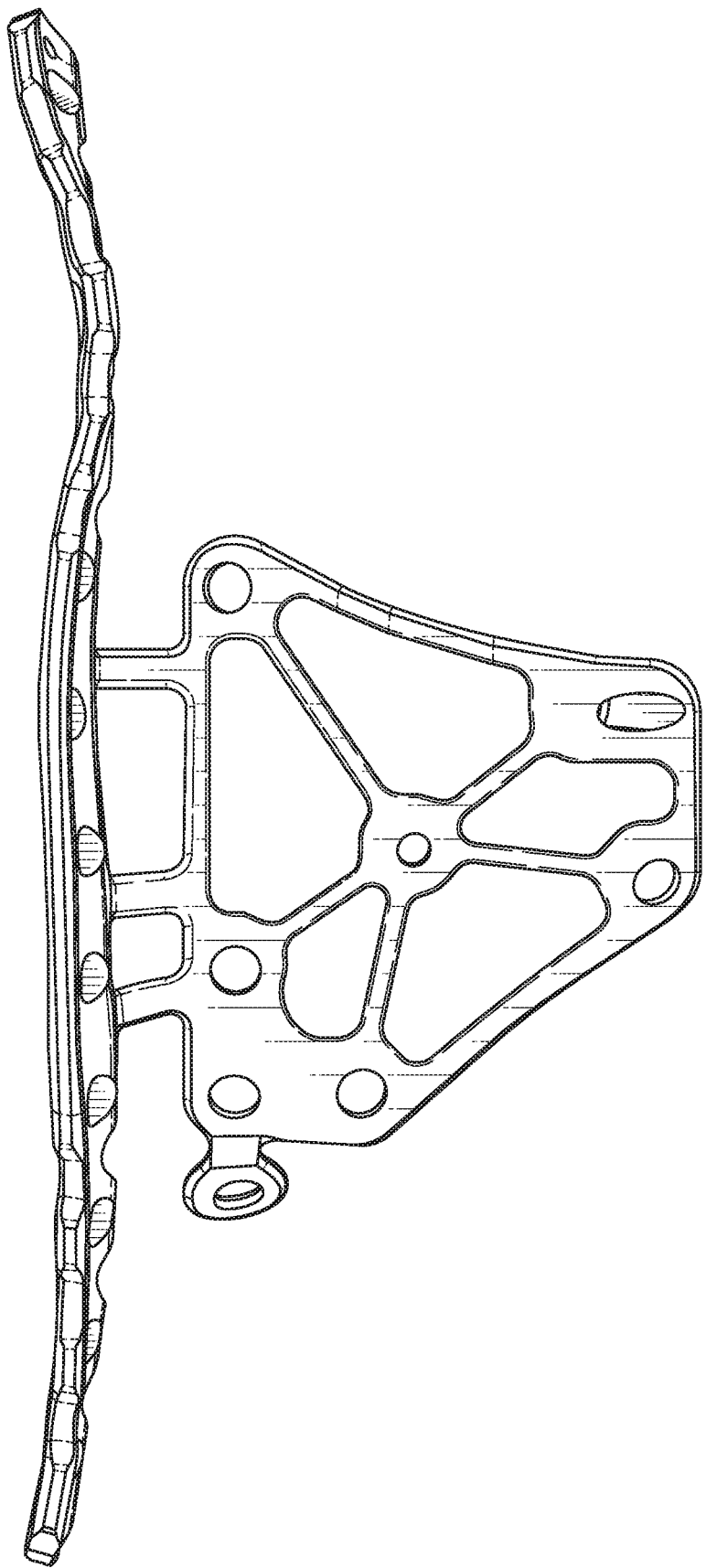
FIG. 15C is a rear perspective view of the bone plating system of the present disclosure as shown in FIG. 15A.
Figure 15D:
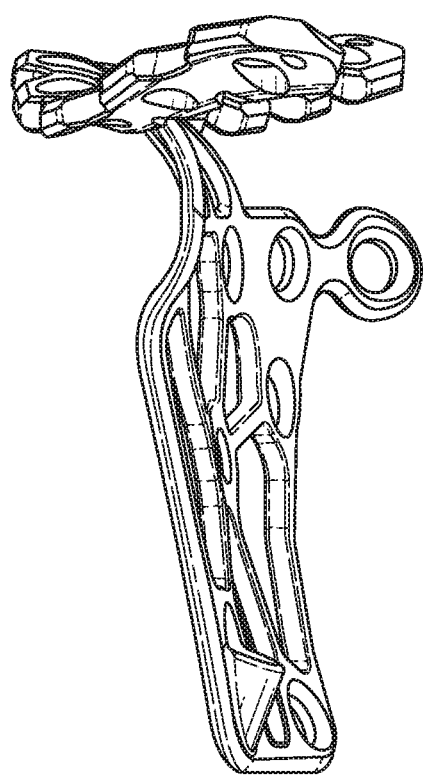
FIG. 15D is a first side perspective view of the bone plating system of the present disclosure as shown in FIG. 15A.
Figure 15E:
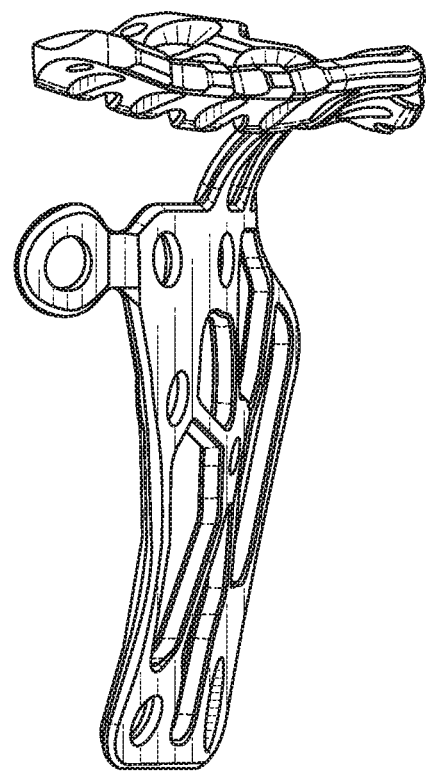
FIG. 15E is a second side perspective view of the bone plating system of the present disclosure as shown in FIG. 15A.
Figure 15F:
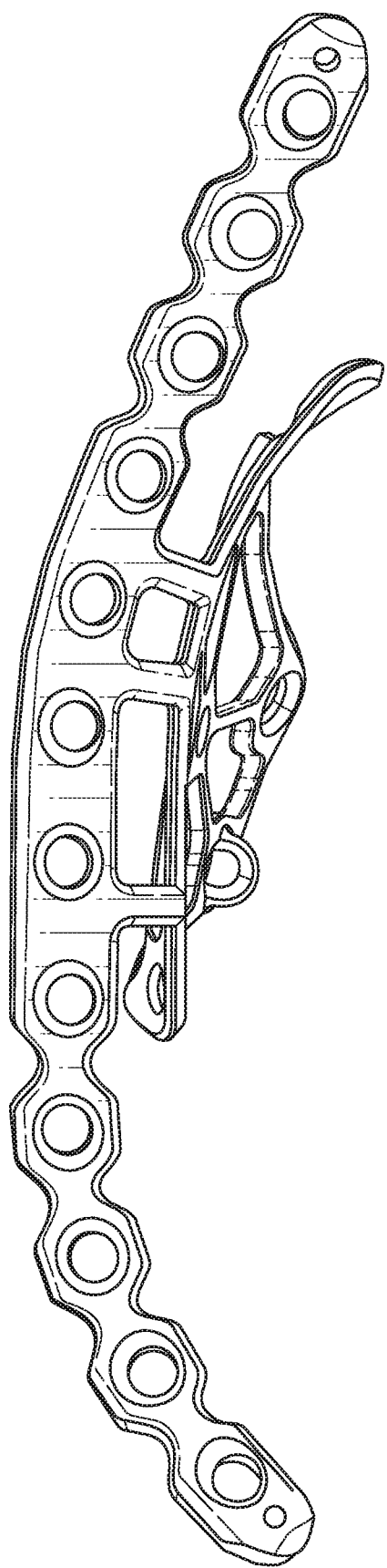
FIG. 15F is a top perspective view of the bone plating system of the present disclosure as shown in FIG. 15A.
Figure 15G:
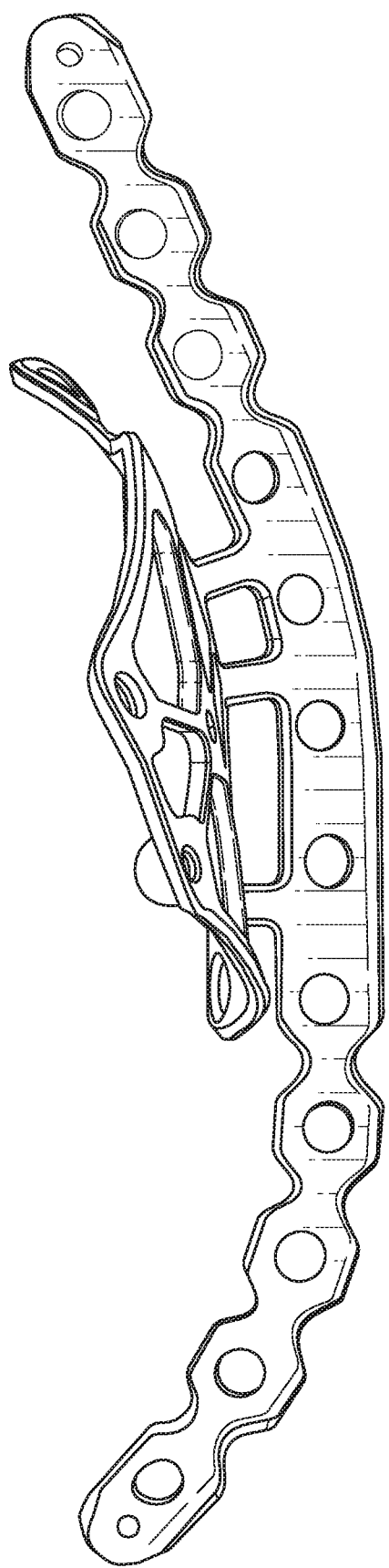
FIG. 15G is a bottom perspective view of the bone plating system of the present disclosure as shown in FIG. 15A.
Figure 16A:
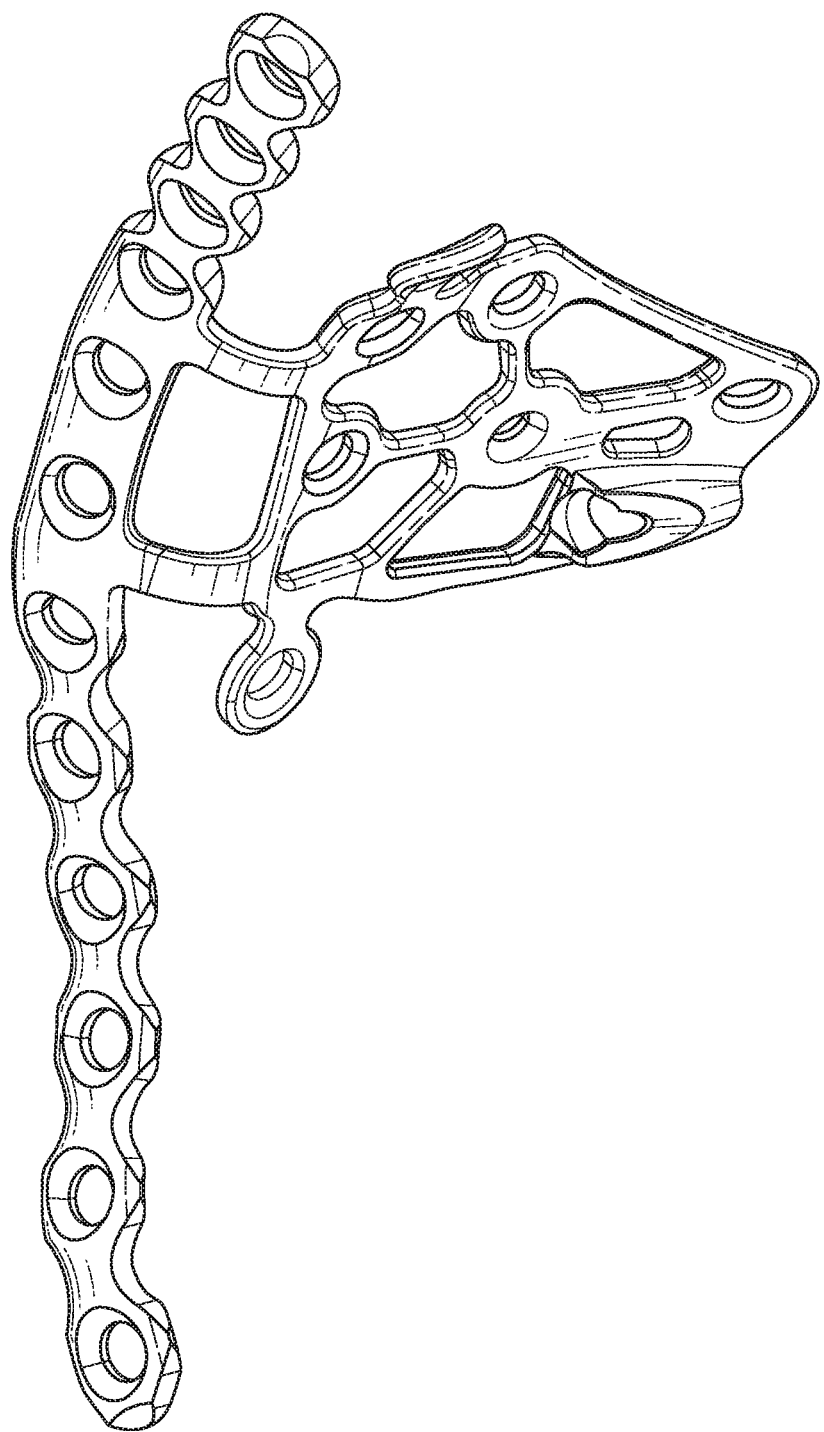
FIG. 16A is a perspective view of an alternative embodiment of a bone plating system of the present disclosure.
Figure 16D:
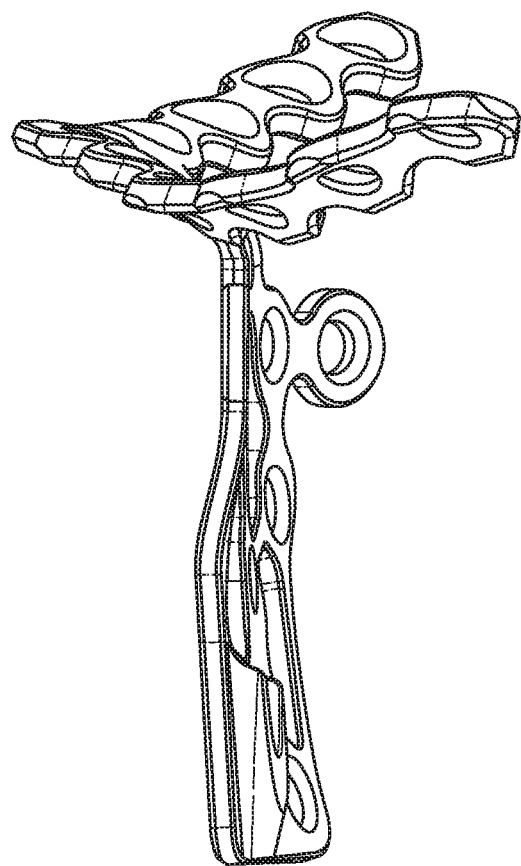
FIG. 16D is a first side perspective view of the bone plating system of the present disclosure shown in FIG. 16A.
Figure 16E:
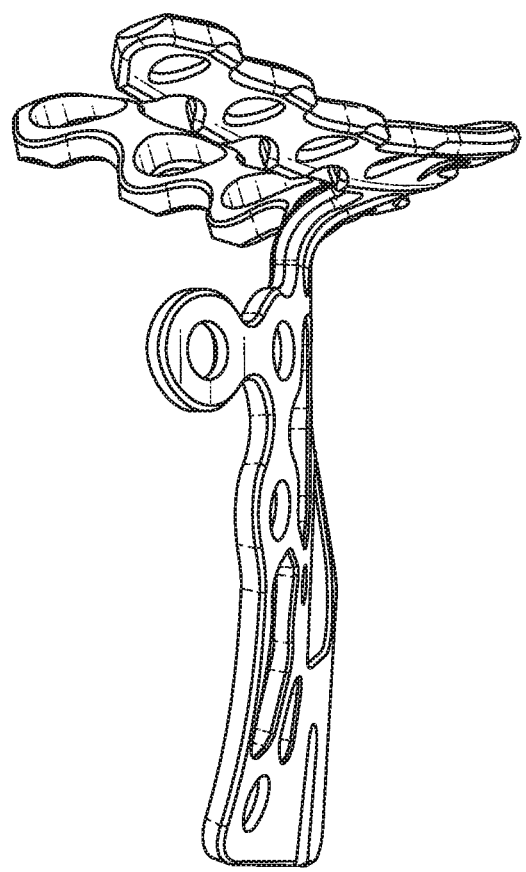
FIG. 16E is a second side perspective view of the bone plating system of the present disclosure shown in FIG. 16A.
Figure 16F:
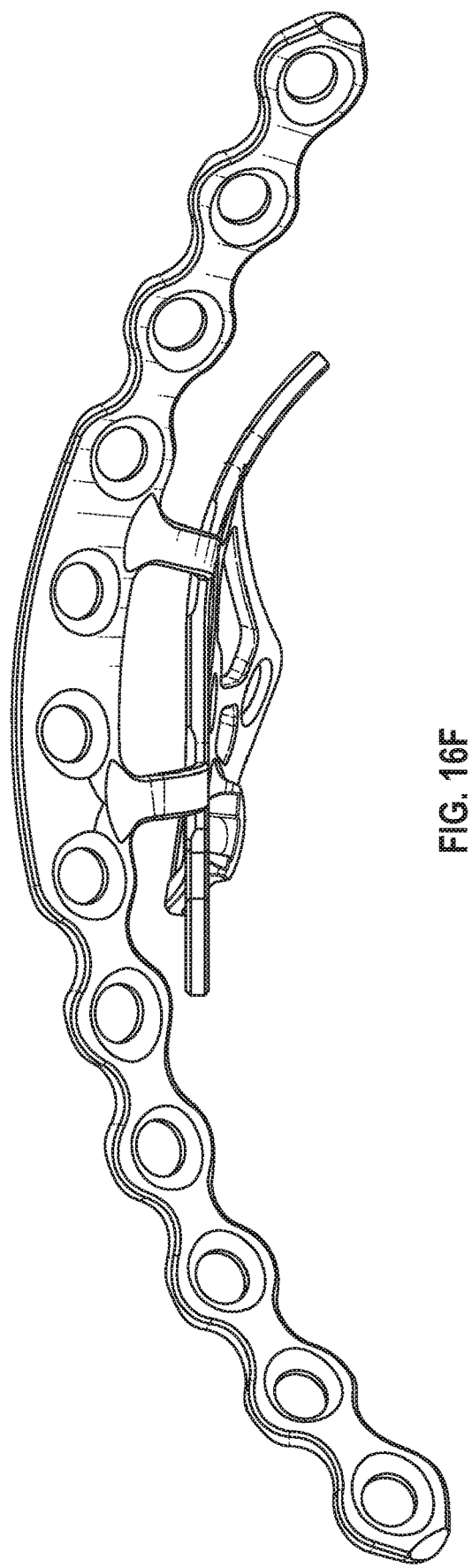
FIG. 16F is a top perspective view of the bone plating system of the present disclosure shown in FIG. 16A.
Figure 16G:
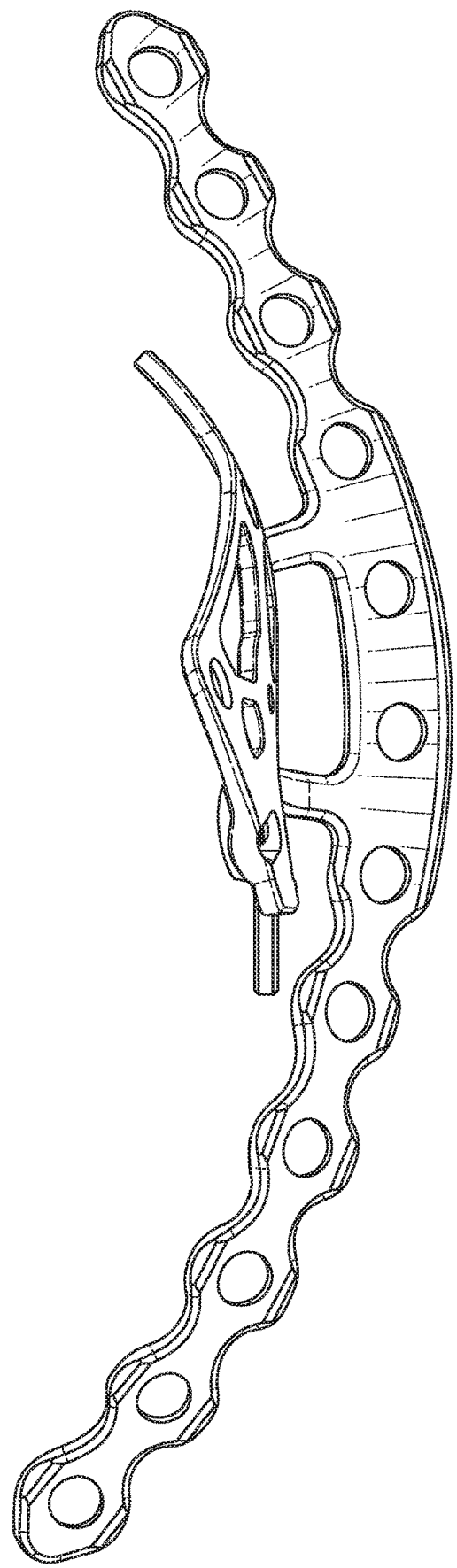
FIG. 16G is a bottom perspective view of the bone plating system of the present disclosure shown in FIG. 16A.
Figure 17A:
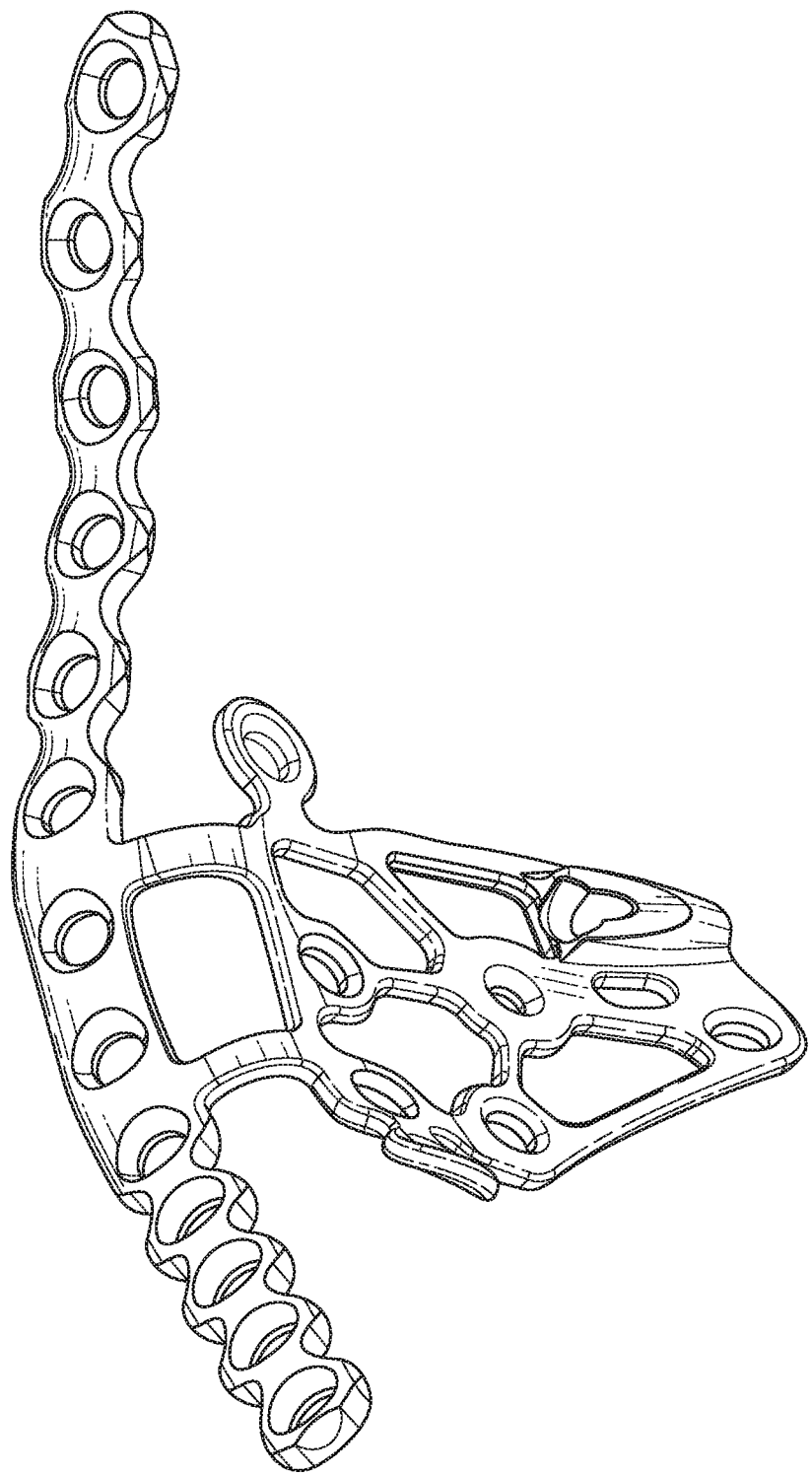
FIG. 17A is a perspective view of an alternative embodiment of a bone plating system of the present disclosure.
Figure 17B:
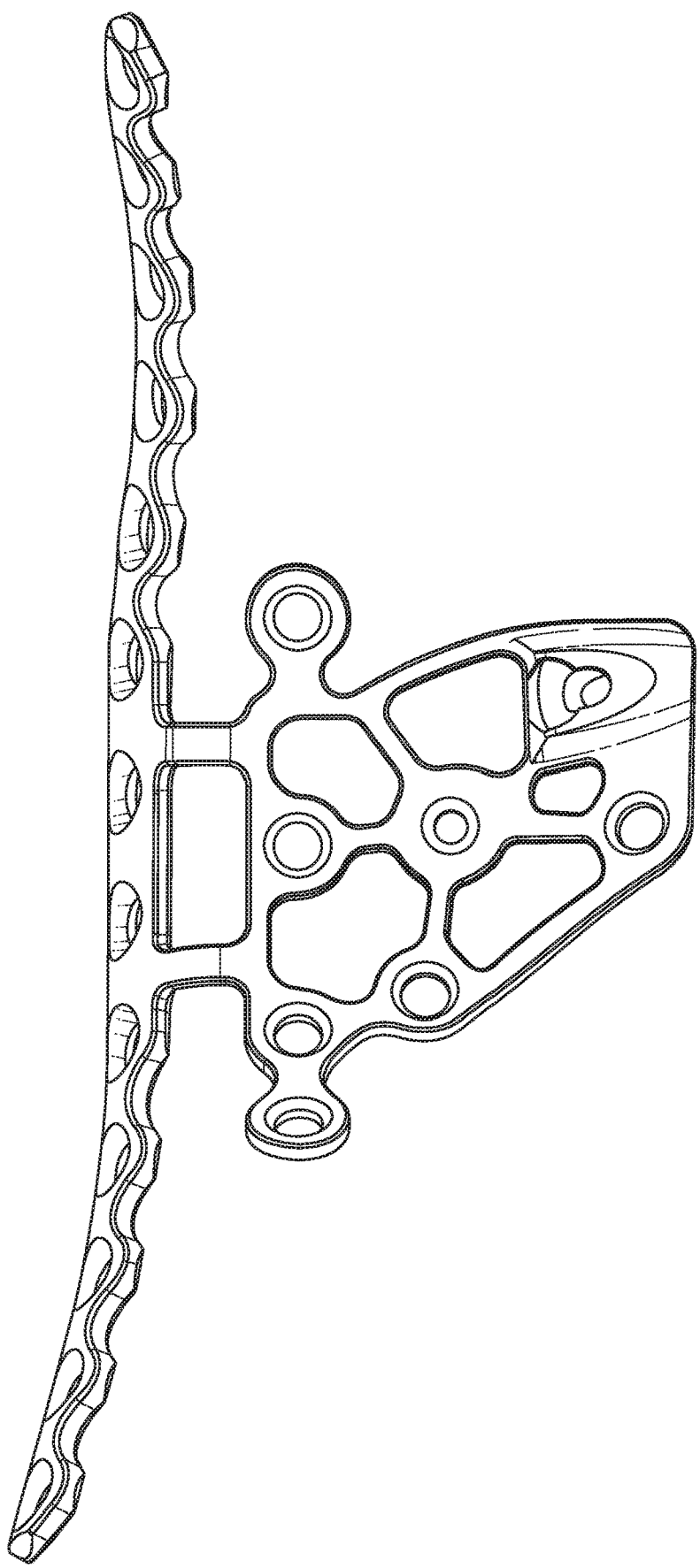
FIG. 17B is a front perspective view of the bone plating system of the present disclosure shown in FIG. 17A.
Figure 17C:
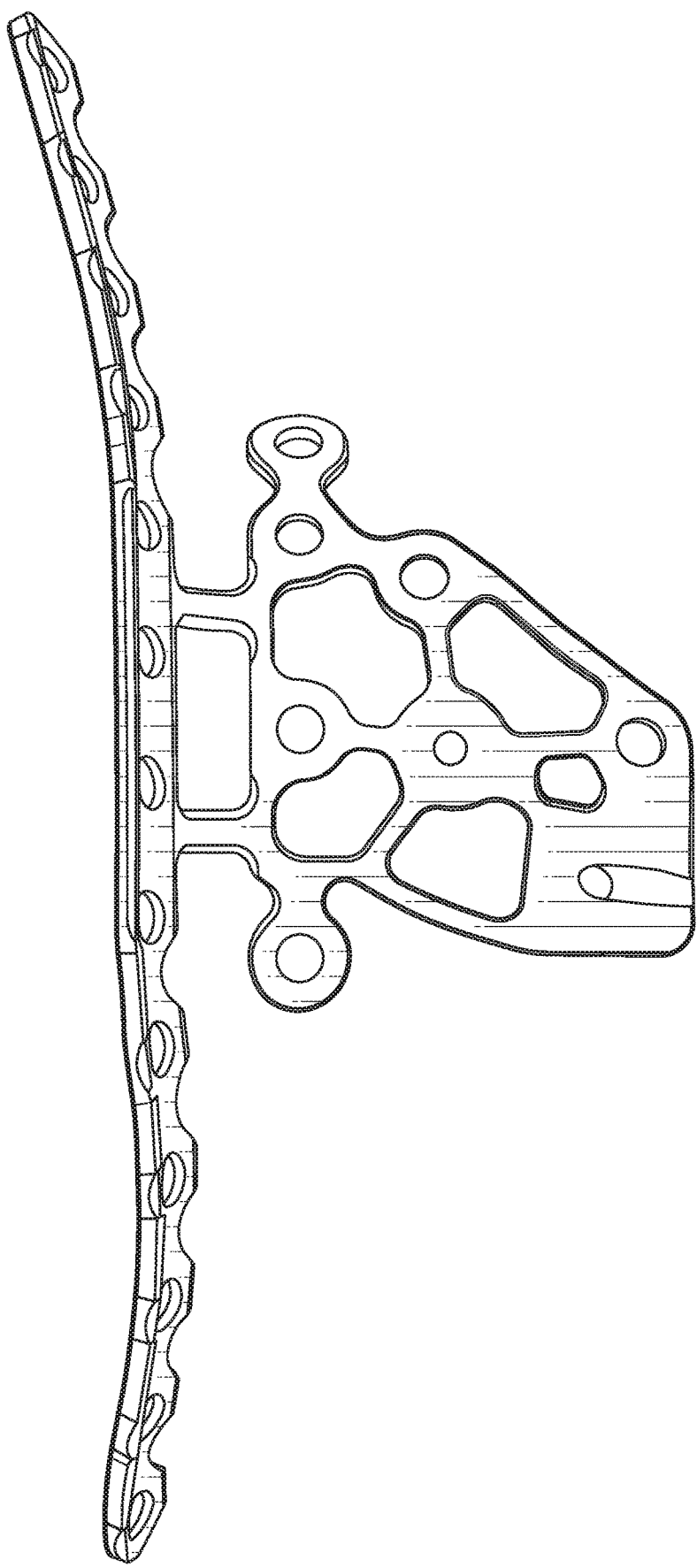
FIG. 17C is a rear perspective view of the bone plating system of the present disclosure shown in FIG. 17A.
Figure 17D:
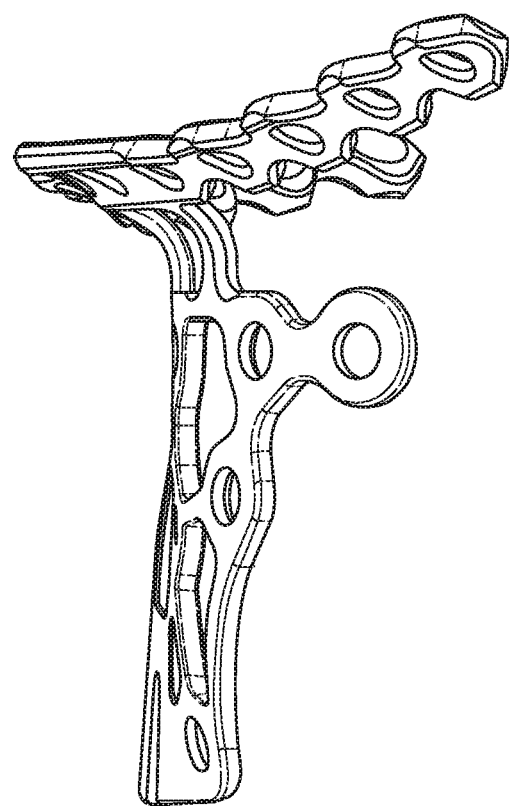
FIG. 17D is a first side perspective view of the bone plating system of the present disclosure shown in FIG. 17A.
Figure 17E:
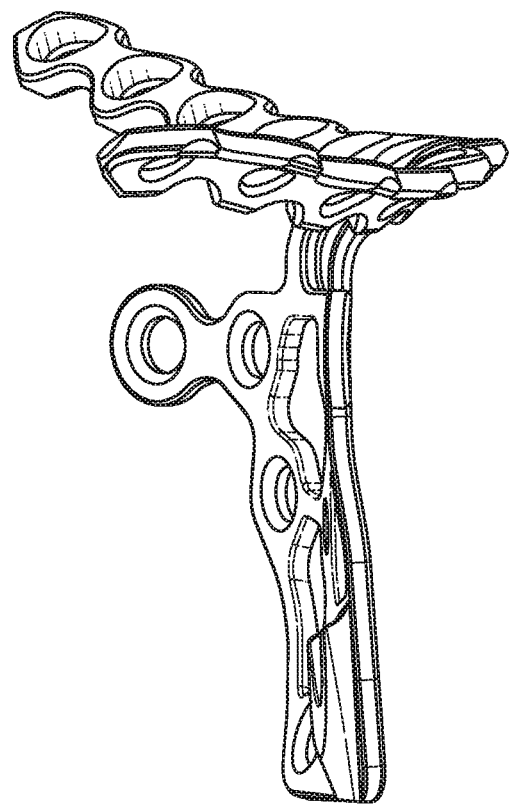
FIG. 17E is a second side perspective view of the bone plating system of the present disclosure shown in FIG. 17A.
Figure 17F:
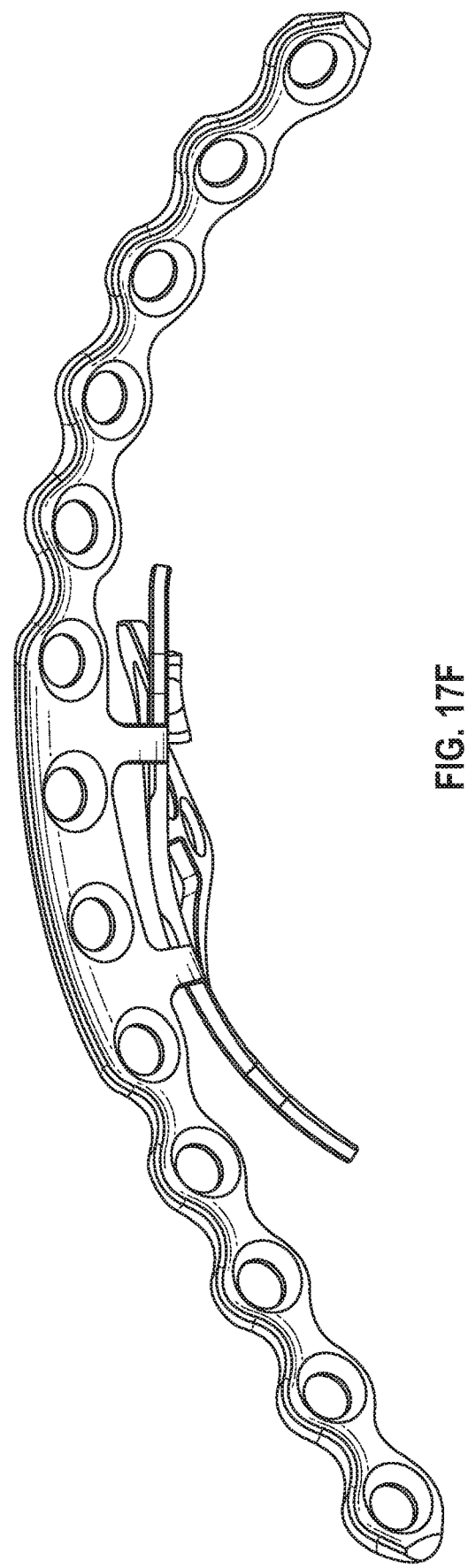
FIG. 17F is a top perspective view of the bone plating system of the present disclosure shown in FIG. 17A.
Figure 17G:
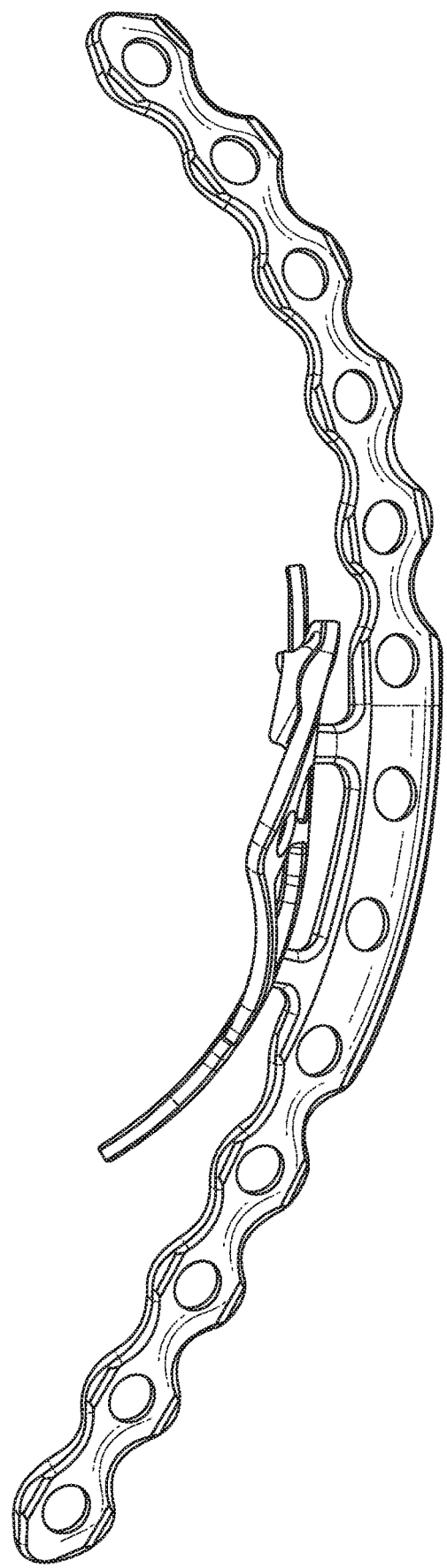
FIG. 17G is a bottom perspective view of the bone plating system of the present disclosure shown in FIG. 17A.

The bone plating system 10c shown in FIGS. 9A-9C includes a first bone plate 100c, a second bone plate 200c, two tertiary fastening members designated 400a and 400b, and two connecting bridge members 500. The first bone plate 100c includes a first bone engaging surface 105, a tissue engaging surface 110, a first edge 115, a second edge 120, a first end 125, and a second end 130. A length 135 extends from the first end 125 to the second end 130 of the first bone plate 100c. Spaced equally along a longitudinal axis running along the length 135 of the first bone plate 100c are a plurality of screw apertures 600 and forming bridges 605 generally placed between the screw apertures 600. In the embodiment of FIGS. 9A-9C, the first bone plate 100c comprises eleven screw apertures 600 and seven forming bridges 605. The screw apertures 600 are identical to the screw apertures 145, and the forming bridges 605 are identical to the forming bridges 155 in shape, function, structure, and positioning considering the differences in the number of each.

The second bone plate 200c includes a second bone engaging surface 205, a second tissue engaging surface 210, a proximal end 215, and a distal end 220. The second bone plate 200c further includes internal struts 240c, through holes 245c, and secondary screw apertures 250. The internal struts 240c are generally identical to internal struts 240 albeit the internal struts 240c are arranged in a different web-like pattern than internal struts 240. Likewise, the through holes 245c are generally identical to through holes 245 albeit the through holes 245c are shaped and sized differently than the through holes 245. The second bone plate 200c also includes at least one securing port 270c and at least one tertiary fastening member 400 connected to the second bone plate 200c via an external strut 402. Further, the bone plating system 10c includes a plurality of connecting bridge members 500 connecting the first bone plate 100c to the second bone plate 200c with two such connecting bridge members 500 shown in the embodiment of the bone plating system 10c shown in FIGS. 9A-9C. In use, the bone plating system 10c is placed within the pelvis A of a patient 15 in the same manner using the same tools and screws 30, 40, 50 and fastener 271 as bone plating system 10 with the one difference being the structure of the at least one securing port 270c.

The at least one securing port 270c of the second bone plate 200c includes a bore 290c extending from the second tissue engaging surface 210 generally towards the second bone engaging surface 205. A bore central axis 292c runs through a center of the bore 290c—i.e., the bore central axis 292c is a line extending longitudinally through a center of the bore 290c in a direction substantially oriented toward the distal end 220 and away from the proximal end 215 of the second bone plate 200c. As shown in FIG. 9C, when the fastener 271 is within the at least one securing port 270c in at least one configuration, the fastener central axis 276 is adjacent to and/or coextensive with the bore central axis 292c. In some embodiments, the bore 290c may not be a perfect circle and have, rather, a slightly elongated oval or ellipse shape. For example, when the bore 290c has an ellipse shape a length along the major radius may be from about 3 mm to about 9 mm with a length along the minor radius of from about 3 mm to about 6 mm.

In alternative embodiments, the fastener 271 can be inserted into the bore 290c of the at least one securing port 270c at an angle less than or greater than that of the bore central axis 292c—i.e., at an angle from about 1 degree to about 75 degrees. As such, the angle at which the fastener 271 can be inserted through the bore 290c can be +/−75 degrees from the bore central axis 292c as indicated generally by fastener insertion vectors 294c, 296c. The degree by which the fastener 271 can deviate from the bore central axis 292c is identical to the degree by which the fastener can deviate from the bore central axis 292. In particular, it is contemplated that insertion of the fastener 271 can deviate from the bore central axis 292c in an amount ranging from where insertion vector 296c is at an angle of about 10 degrees measured from the bone engaging axis 265 and insertion vector 294c is at an angle of about 90 degrees measured from the bone engaging axis 265. In an alternate embodiment, insertion of fastener 271 can deviate from the bore central axis 292c in an amount ranging from where insertion vector 296c is at an angle of about 15 degrees measured from the bone engaging axis 265 and insertion vector 294c is at an angle of about 33 degrees measured from the bone engaging axis 265.

In further detail, the at least one securing port 270c has a wall 295c surrounding at least a portion of the bore 290c with the wall 295c having an upper surface 700 and a lower surface 705. The wall 295c defines a fastener head support surface 300c defining a fastener head receiving volume 305c of the bore 290c disposed a predetermined distance above the second tissue engaging surface 210 as shown in FIG. 9C. The at least one securing port 270c further including a port through passage 710 shown in particular in FIG. 9B wherein the port through passage 710 has a first width 715 adjacent the lower surface 705 of the wall 295c that tapers toward a point 720 adjacent the distal end 220 of the second bone plate 200c. As shown in FIG. 9B, the port through passage 710 has a generally wish-bone configuration. One of ordinary skill in the art would appreciate, however, that the port through passage 710 could have any shape desired by the surgeon that allows the fastener 271 to move through the bore 290c, through the second bone plate 200c, and into the second bone portion 35 of the patient 15 at an angle measured from the bone engaging axis as described hereinabove. In use, when the fastener 271 is placed within the bore 290c, the head 274 of the fastener 271 is in a shrouded configuration—i.e., the head 274 of the fastener 271 is at least partially nested within the fastener head receiving volume 305c and at least a portion of the head 274 does not extend into tissue adjacent the second tissue engaging surface 210 of the second bone plate 200c. In this manner, the fastener head receiving volume 305c is formed as a countersunk hole. This "countersunk hole" configuration is such that the fastener head support surface 300c is provided with a curved fillet in one embodiment or a conical chamfer in an alternative embodiment—i.e., the fastener head support surface 300c can be of any shape that corresponds to the underside of the head 274 of the fastener 271. In such a "countersunk hole" configuration of the fastener head receiving volume 305c, the head 274 of the fastener 271 is generally seated within the fastener head receiving volume 305c and does not interact or engage substantially with tissue that may come into contact with the second tissue engaging surface 210 of the second bone plate 200c.

The fastener head support surface 300c is adjacent to the lower surface 705 of the at least one securing port 270c such that the fastener head support surface 300c and the lower surface 705 have a bore vertex 320c extending around at least a portion of the bore 290c. The fastener head support surface 300c has a fastener support axis 325c adjacent to the bore vertex 320c. The fastener support axis 325c extends at a first angle 330c that is less than or equal to 90 degrees relative to the bone engaging axis 265. In one embodiment, the first angle 330c can be between 1 and 15 degrees. In other embodiments, the first angle 330c can be between 15 and 35 degrees, 35 and 60 degrees, 60 and 75 degrees, and 75 and 90 degrees. In a preferred embodiment, the first angle 330c is between 45 and 80 degrees, preferentially being between 55 and 75 degrees. The fastener head support surface 300c has a spherical diameter from about 6 mm to about 9 mm.

Figure 5A:
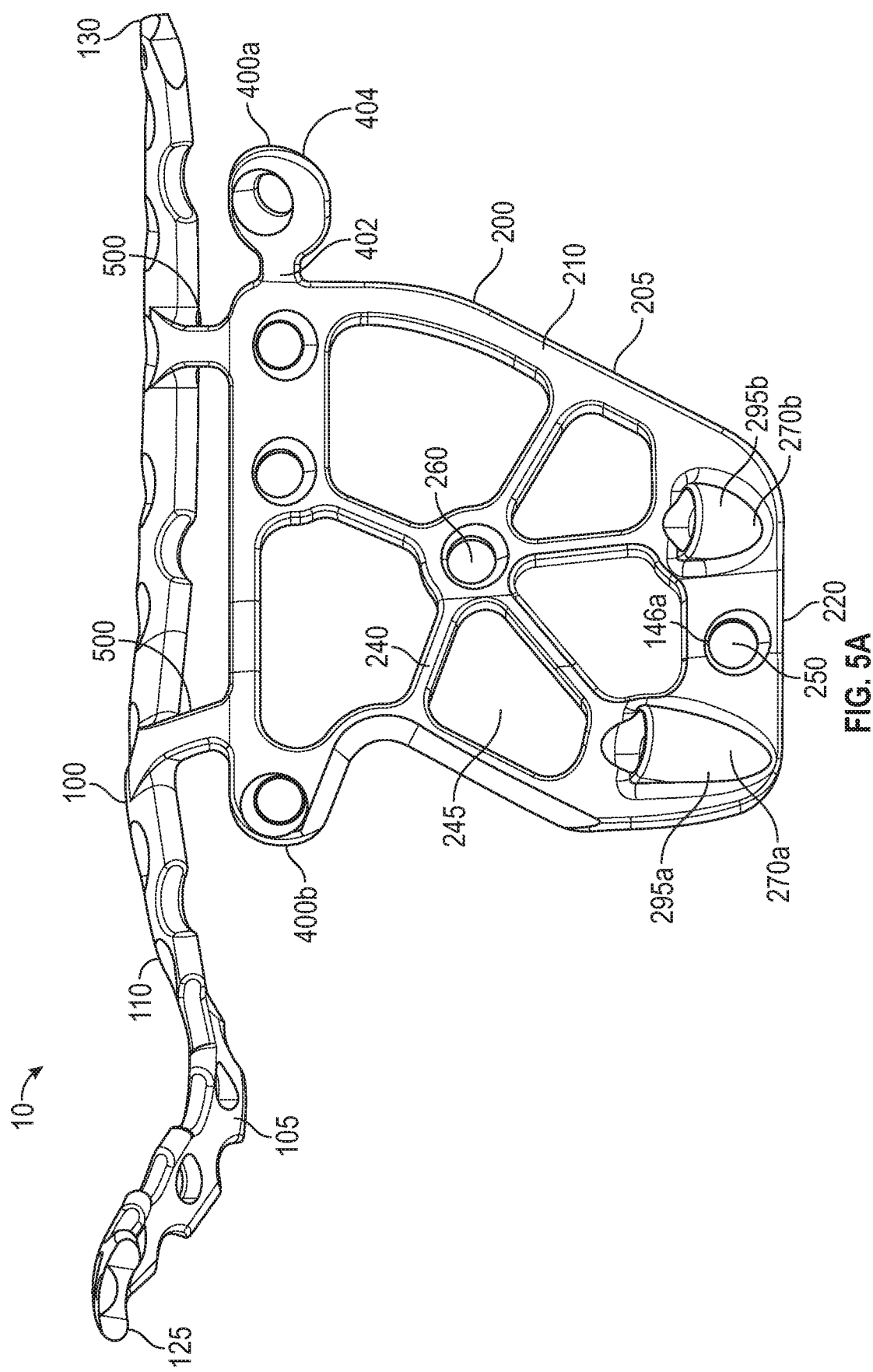
FIG. 5A is a front perspective view of an alternative embodiment of a bone plating system of the present disclosure.
Figure 5B:
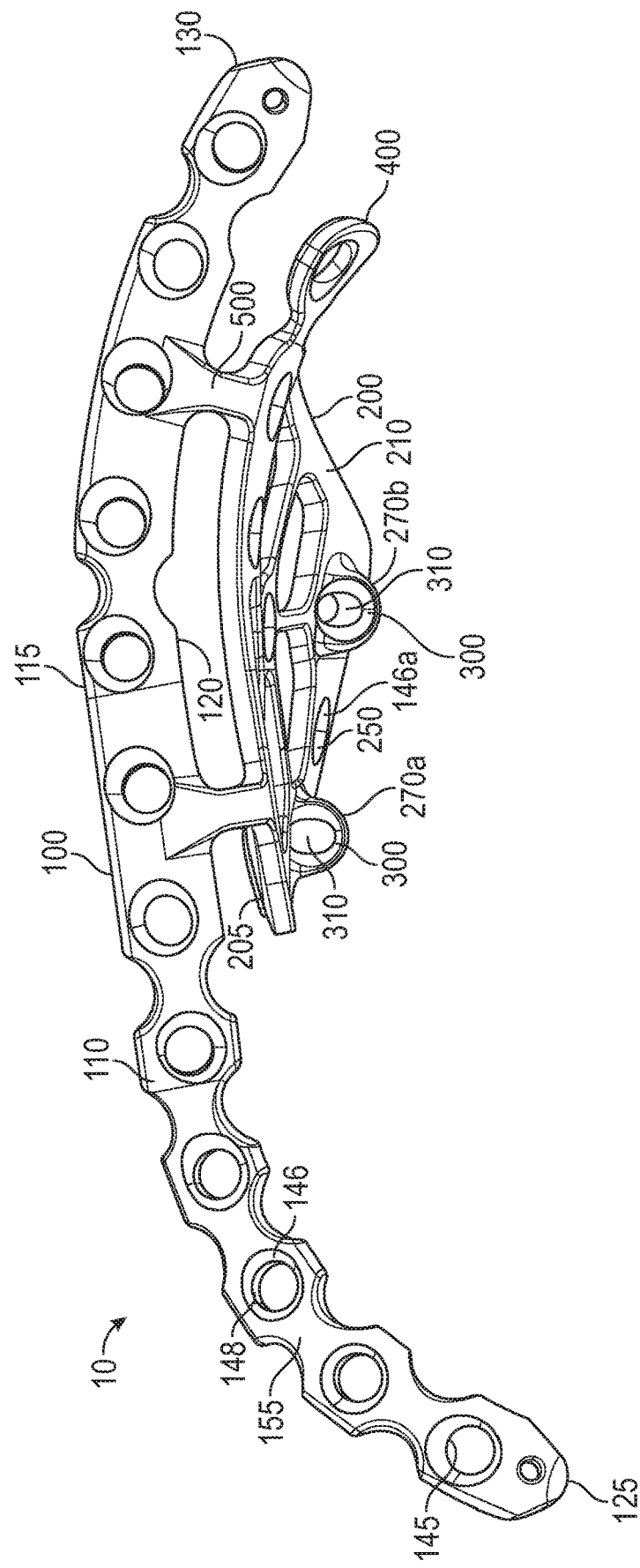
FIG. 5B is a top perspective view of the bone plating system of the present disclosure as shown in FIG. 5A.
Figure 5C:
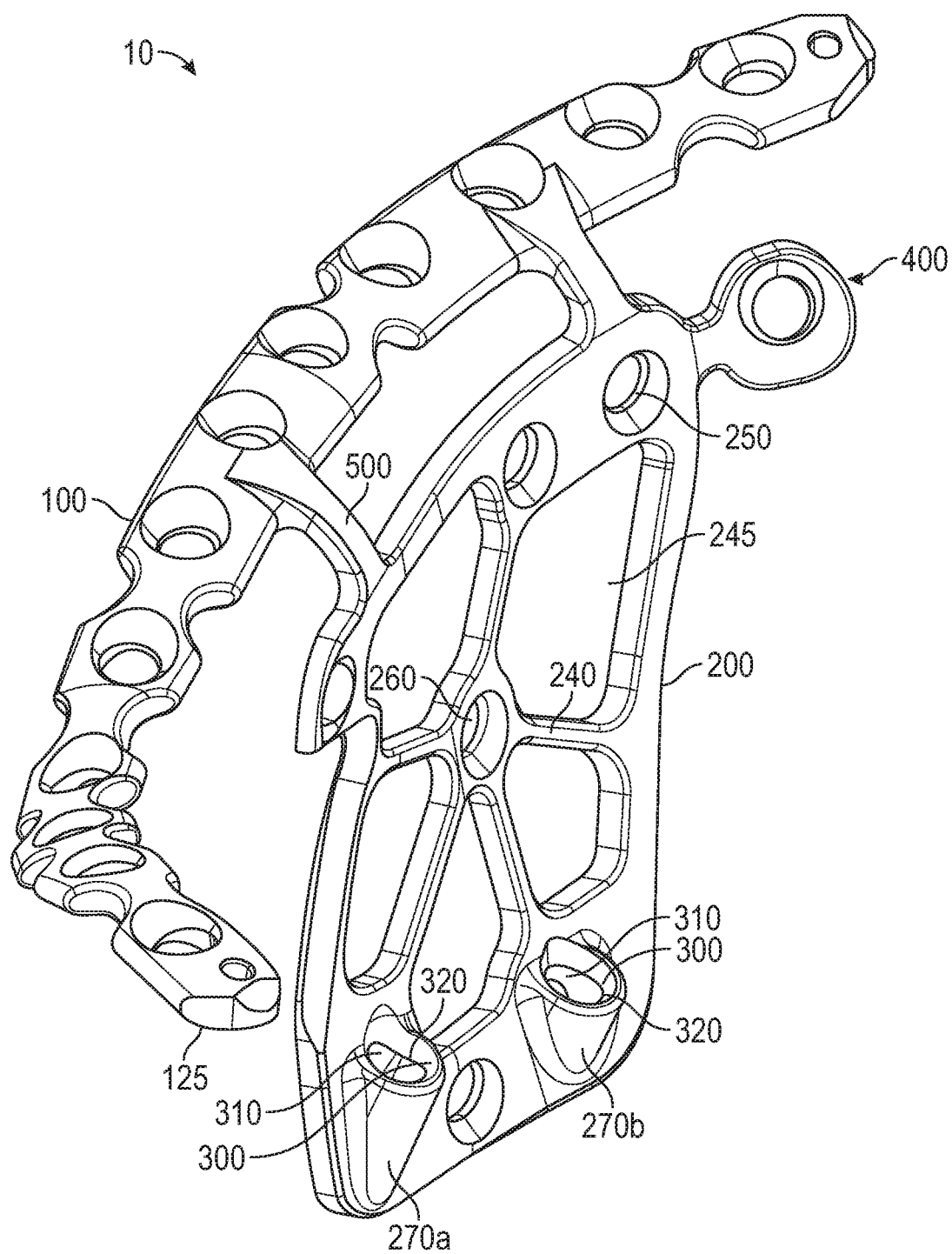
FIG. 5C is a side perspective view of the bone plating system of the present disclosure as shown in FIG. 5A.
Figure 5D:
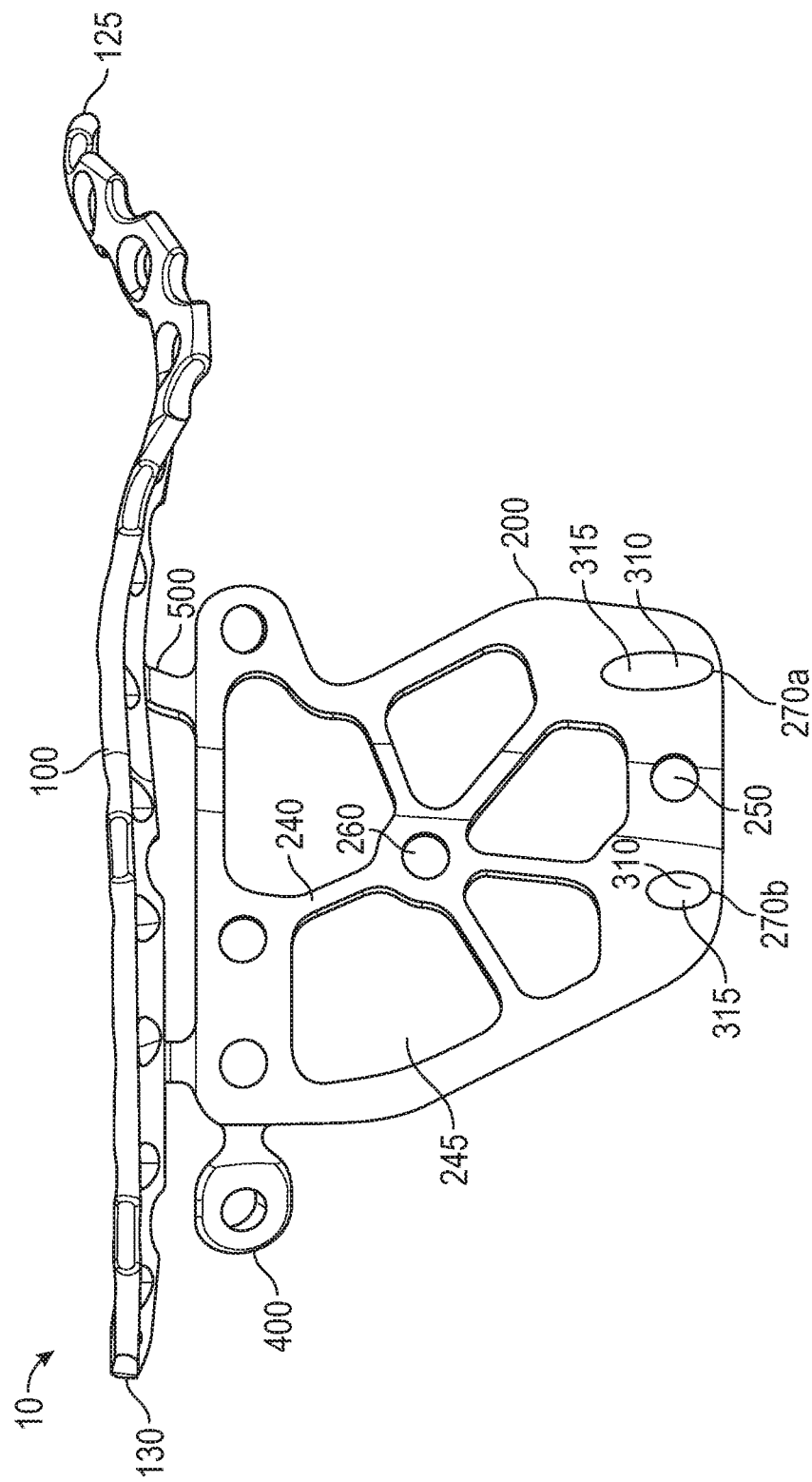
FIG. 5D is a rear perspective view of the bone plating system of the present disclosure as shown in FIG. 5A.
Figure 5E:
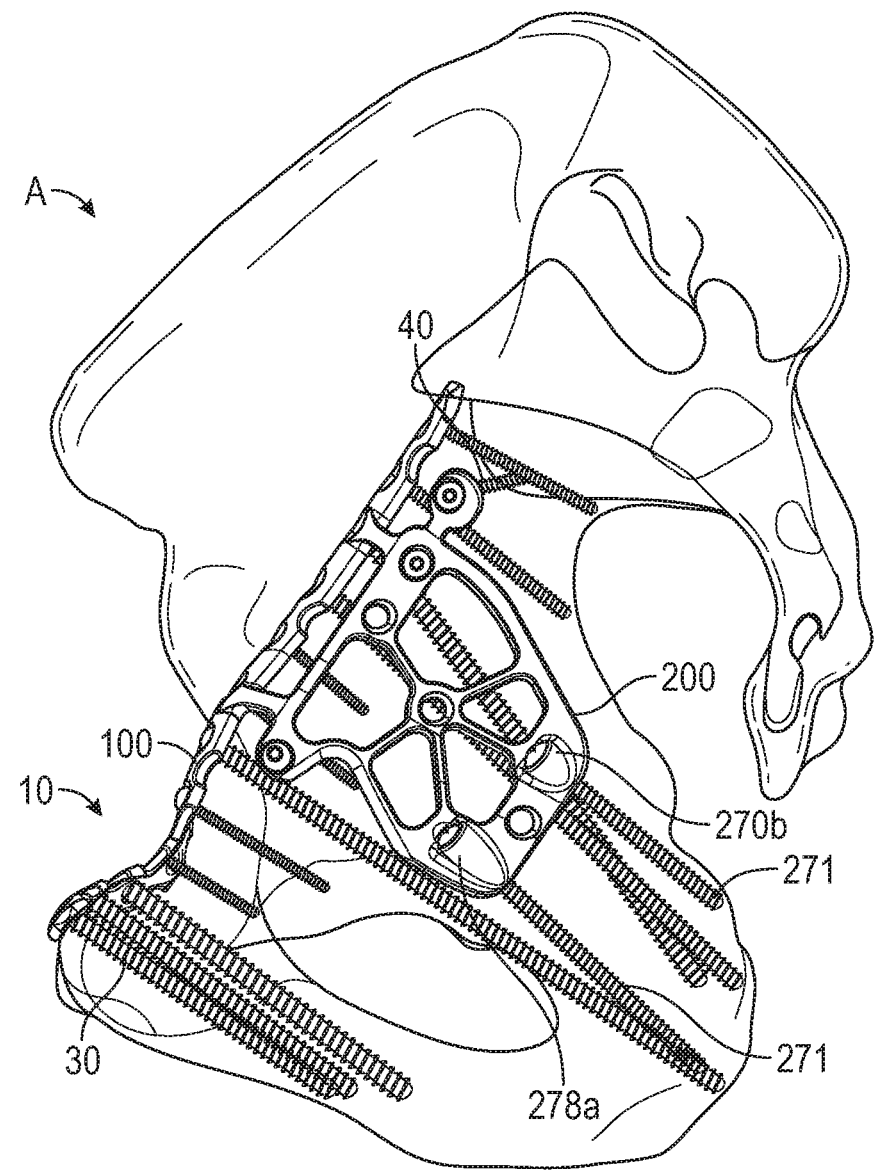
FIG. 5E is a three-dimensional view of the bone plating system of the present disclosure as shown in FIG. 5A intraoperatively placed within a patient's pelvis and showing the insertion of a plurality bone screws in combination with the bone plating system.

In use, and as more particularly shown in FIGS. 3, 4, and 5E, the surgeon configures the bone plating system 10 to generally conform to the patient's anatomy. In particular, after achieving initial reduction of the fracture intra-operatively the surgeon can insert a bending template (not shown) into the portion of the pelvis A where placement of the bone plating system 10 is intended. A bending template is typically thin and easy to shape to the configuration of the bones in the pelvis A. Oftentimes such bending templates are made from a very ductile aluminum alloy less than a millimeter in thickness. Alternatively, the surgeon may place the bone plating system 10 generally into position within the pelvis A-fitting the bone plating system 10 visually and by feel— with the first bone plate 100 adjacent the first bone portion 20 (e.g., the pelvic brim B as shown in FIGS. A, 3, 4, and 5E), the second bone plate 200 adjacent the second bone portion 35 (e.g., the quadrilateral surface C as shown in FIGS. A, 3, 4, and 5E), and with the connecting bridge members 500 connecting the first bone plate 100 to the second bone plate 200. In this placement, the first bone engaging surface 105 of the first bone plate 100 is in at least partial contact with the surface of the pelvic brim B and the second bone engaging surface 205 of the second bone plate 200 is in at least partial contact with the quadrilateral surface C. The bone plating system 10 is bent into shape in conformity with the bending template or according to trial and error intra-operatively against the actual anatomical structures of the patient.

In alternate embodiments, the bone plating system 10 will be provided to the surgeon as a kit comprising one or more "sizing trials" of the bone plating system 10. Such sizing trials of the bone plating system 10 are generally identical to the bone plating system 10 albeit having different sizes and/or three-dimensional configurations to fit the differing size and shape of the patient's anatomy. The sizing trials are generally more rigid, less detailed, and non-implantable versions of the bone plating system 10. In use, a surgeon would select a sizing trial of the bone plating system 10 from a kit containing a plurality of sizing trials that appears to match most closely to the patient's size and anatomy. The surgeon thereafter places the chosen sizing trial adjacent the patient's anatomy to gauge the appropriateness (or lack thereof) of the fit of the sizing trial to the patient's anatomy and/or the pattern of fracture F (FIG. A). Once a sizing trial is found to most closely approximate the patient's anatomy, a bone plating system 10 that best approximates the size and shape of the sizing trial is selected for implantation within the patient adjacent the first bone portion 20 and the second bone portion 35.

At least one of the plurality of screw apertures 145 of the first bone plate 100—for example, but not by way of limitation, the screw aperture 145$k$ (FIG. 1A)—can be chosen by the surgeon to place a first screw 30 for securing the first bone plate 100 to the first bone portion 20. Although this embodiment contemplates the insertion of the screw 30 through at least one of the screw apertures 145, alternative embodiments contemplate that the surgeon may elect to forego inserting the screw 30 in any of the secondary screw apertures 145. In particular, the surgeon places the screw 30 into screw aperture 145$k$ generally along its central axis 151 such that a tip of a shaft of screw 30 enters and moves through the screw head receiving volume 147, through the screw shaft receiving volume 149, and into contact with the first bone portion 20. The surgeon continues to move the screw 30 along the central axis 151 such that the shaft of the screw 30 enters the first bone portion 20. The screw 30 is further tightened by the surgeon such that threads of the screw 30 further enter the first bone portion 20, thereby pulling the first bone engaging surface 105 adjacent the screw aperture 145$k$ into intimate and engaging contact with the first bone portion 20.

When the first bone engaging surface 105 adjacent the screw aperture 145$k$ is in such intimate and engaging contact with the first bone portion 20, an outer surface of a head of the screw 30 is tightly disposed against the screw head support surface 146 of the screw aperture 145$k$. As the screw apertures 145 have a variety of angles of approach for screw 30 to enter into the first bone portion 20 (i.e., between insertion vectors 152, 153), the surgeon can select an angle of approach to the first bone portion 20 for placing the screw 30 through screw aperture 145$k$ and into the first bone portion 20 that is appropriate for the patient's anatomy (e.g., that best matches the access to the surgical site offered by the approach chosen by the surgeon), best reduces the fracture F of the patient, achieves the greatest purchase of bone across the length the screw 30, and/or is a best compromise factoring all of the above-noted considerations.

For example, the surgeon can select an angle of approach of the screw 30 through the screw aperture 145$k$ to the first bone portion 20 between insertion vectors 152, 153 that allows the screw 30 to bridge two sides of a fracture line (such as fracture F) and thereby reduce the fracture by pulling portions of bone adjacent the fracture toward one another. Additionally, the screw 30 can be of any size, shape, or material suitable for the use in attaching the first bone plate 100 to the first bone portion 20 and, in some cases, reducing the fracture F within the acetabulum E of the pelvis A. The surgeon can thereafter insert additional screws 30 within screw apertures 145$a$-145$j$ in a sequential or other ordered manner such that the first bone plate 100 is secured to the first bone portion 20 (e.g., the pelvic brim B, FIG. A) of the patient. It will be understood by those of ordinary skill in the art that not all screw apertures 145$a$-145$k$ need have screws 30 inserted therein.

As shown in FIGS. 4, and 5E, the screws 30 are shown inserted through the plurality of screw apertures 145 in the first bone plate 100 and into the first bone portion 20. As can be appreciated in particular from FIGS. 4 and 5E, the placement of screws 30 within the screw apertures 145 can be at any number of insertion vectors deviating from the central axis 151 and between insertion vectors 152, 153. The choice of the placement of screws 30 within the screw apertures 145 is within the skill and judgment of the surgeon and may be dictated, generally, by the anatomy of the patient's pelvis A (FIG. A) in that the screws 30 are generally placed through the screw apertures 145 in a manner to join pieces of fractured bone and/or gain sufficient purchase in the bone along the length of the screws 30 to hold the first bone plate 100 securely to the first bone portion 20 of the patient.

At least one of the secondary screw apertures 250 of the second bone plate 200—for example, but by way of limitation, the secondary screw aperture 250$a$ (shown in FIG. 1B)—can be chosen by the surgeon to place a screw 40 for securing the second bone plate 200 to the second bone portion 35. Although this embodiment contemplates the insertion of the screw 40 through at least one of the secondary apertures 250, alternative embodiments contemplate that the surgeon may elect to forego inserting the screw 40 in any of the secondary screw apertures 250. In particular, the surgeon places the screw 40 into secondary screw aperture 250$a$ generally along its secondary central axis 251 such that a tip of a shaft of screw 40 enters and moves through the screw head receiving volume 147$a$, through the screw shaft receiving volume 149$a$, and into contact with the second bone portion 35. The surgeon continues to move the screw 40 along the secondary central axis 251 such that the shaft of the screw 40 enters the second bone portion 35. The screw 40 is further tightened by the surgeon such that threads of the screw 40 further enter the second bone portion 35, thereby pulling the second bone engaging surface 205 adjacent the secondary screw aperture 250$a$ into intimate and engaging contact with the second bone portion 35.

When the second bone engaging surface 205 adjacent the secondary screw aperture 250$a$ is in such intimate and engaging contact with the second bone portion 35, an outer surface of a head of the screw 40 is tightly disposed against the screw head support surface 146$a$ of the secondary screw aperture 250$a$. As the secondary screw apertures 250 have a variety of angles of approach for screw 40 to enter the second bone portion 35 (i.e., between secondary insertion vectors 252, 253), the surgeon can select an angle of approach to the second bone portion 35 for placing the screw 40 through secondary screw aperture 250$a$ and into the second bone portion 35 that is appropriate for the patient's anatomy (e.g., that best matches the access to the surgical site offered by the approach chosen by the surgeon), best reduces the fracture F of the patient, achieves the greatest purchase of bone across the length the screw 40, and/or is a best compromise factoring all of the above-noted considerations.

For example, the surgeon can select an angle of approach of the screw 40 through the secondary screw aperture 250$a$ to the second bone portion 35 between secondary insertion vectors 252, 253 that allows the screw 40 to bridge two sides of a fracture line (such as fracture F, FIG. A) and thereby reduce the fracture by pulling portions of bone adjacent the fracture toward one another. Additionally, the screw 40 can be of any size, shape, or material suitable for use in attaching the second bone plate 200 to the second bone portion 35 and, in some cases, reducing the fracture F within the acetabulum E of the pelvis A (FIG. A). The surgeon can thereafter insert additional screws 40 within secondary screw apertures 250b-250d in a sequential or other ordered manner such that the second bone plate 200 is secured to the second bone portion 35 (e.g., the acetabular surface C, FIG. A) of the patient. It will be understood by those of ordinary skill in the art that not all second screw apertures 250b-250d need have screws 40 inserted therein.

As shown in FIGS. 4 and 5E, the screws 40 are shown inserted through the plurality of secondary screw apertures 250 in the second bone plate 200 and into the second bone portion 35. As can be appreciated in particular from FIGS. 4 and 5E, the placement of screws 40 within the secondary screw apertures 250 can be at any number of insertion vectors deviating from the secondary central axis 251 and between insertion vectors 252, 253. The choice of the placement of screws 40 within the secondary screw apertures 250 is within the skill and judgment of the surgeon and may be dictated, generally, by the anatomy of the patient's pelvis A (FIG. A) in that the screws 40 are generally placed through the secondary screw apertures 250 in a manner to join pieces of fractured bone and/or gain sufficient purchase in the bone along the length of the screw 40 to hold the second bone plate 200 securely to the second bone portion 35 of the patient.

At least one of the tertiary fastening members 400 of the second bone plate 200, as shown in FIGS. 4 and 5E, can be chosen by the surgeon to place a screw 50 for further securing the second bone plate 200 to the second bone portion 35. Although this embodiment contemplates the insertion of the screw 50 through at least one of the tertiary screw apertures 406, alternative embodiments contemplate that the surgeon may elect to forego inserting the screw 50 in any of the tertiary screw apertures 406. In particular, the surgeon places the screw 50 in the tertiary screw aperture 406 generally along its tertiary central axis 405 such that a tip of a shaft of the screw 50 enters and moves through the screw head receiving volume 147b, through the screw shaft receiving volume 149a, and into contact with the second bone portion 35. The surgeon continues to move the screw 50 along the tertiary central axis 405 such that the shaft of the screw 50 enters the second bone portion 35. The screw 50 is further tightened by the surgeon such that threads of the screw 50 further enter the second bone portion 35, thereby pulling the bone contact surface 404 adjacent the tertiary screw aperture 406 of the tertiary fastening member 400 into intimate and engaging contact with the second bone portion 35.

When the bone contact surface 404 adjacent the tertiary screw aperture 406 is in such intimate and engaging contact with the second bone portion 35, an outer surface of a head of the screw 50 is tightly disposed against the screw head support surface 146b of the tertiary screw aperture 406. As the tertiary screw aperture 406 have a variety of angles of approach for screw 50 to enter the second bone portion 35 (i.e., between tertiary insertion vectors 407, 409), the surgeon can select an angle of approach to the second bone portion 35 for placing the screw 50 through the tertiary screw apertures 406 and into the second bone portion 35 that is appropriate for the patient's anatomy (e.g., that best matches the access to the surgical site offered by the approach chosen by the surgeon), best reduces the fracture F of the patient, achieves the greatest purchase of bone across the length the screw 40, and/or is a best compromise factoring all of the above-noted considerations.

For example, the surgeon can select an angle of approach of the screw 50 through the tertiary screw aperture 406 to the second bone portion 35 between tertiary insertion vectors 407, 409 that allows the screw 50 to bridge two sides of a fracture line (such as fracture F) and thereby reduce the fracture by pulling portions of bone adjacent the fracture F toward one another. Additionally, the screw 50 can be of any size, shape, or material suitable for use in further attaching the second bone plate 200 to the second bone portion 35 and, in some cases, further reducing the fracture F within the acetabulum E of the pelvis A (FIG. A). The surgeon can thereafter insert additional screws 50 within other tertiary screw apertures 406 associated with the second bone plate 200 in a sequential or other ordered manner such that the second bone plate 200 is further secured to the second bone portion 35 (e.g., the acetabular surface C or other bone surfaces or prominences of the pelvis A, for example) of the patient. It will be understood by those of ordinary skill in the art that not all tertiary screw apertures 406 need have screws inserted therein as is shown specifically in FIG. 4. Again, it should be understood that a surgeon may choose to not insert screws through any of the screw apertures 145, the secondary screw apertures 250, and/or the tertiary screw apertures 406.

Although the use of the bone plating system 10 hereinabove has been described with respect to insertion of screws 30 through the first bone plate 100 and, once complete, thereafter inserting screws 40 and the screws 50 through the second bone plate 200, one of ordinary skill in the art would appreciate that a surgeon can take a step-wise approach of inserting screws 30, 40, 50 into the first bone plate 100 and the second bone plate 200, respectively. For example, the surgeon can elect to insert the screws 30, 40, 50 in an alternating fashion of 30-40-50-30-40-50 until all the screw apertures 145, secondary screw apertures 250, and tertiary screw apertures 406 have screws 30, 40, 50 respectively inserted therethrough. Additionally, the surgeon can elect to insert screws 30, 40, 50 in any other pattern—for example, but not by way of limitation, 30-40-40-50-30-30-30-40-50—in the surgeon's discretion. The surgeon may even elect to insert screws 40 or screws 50 prior to insertion of screws 30. All of the foregoing is to illustrate that the manner and order in which screws 30, 40, 50 are inserted into the screw apertures 145, the secondary screw apertures 250, and tertiary screw apertures 406 should not be considered as limiting to the present disclosure. In particular and with reference to FIGS. 1A and 8, a preferred particular sequence for inserting screws 30, 40, 50 into the screw apertures 145, the secondary screw apertures, 250, the tertiary screw apertures 406, and the securing port 270 would be as follows: (1) 145k; (2) 145a; (3) 145b; (4) 145i; (5) 145j; (6) 270a (and/or 270b); and (7) 400a. Once again with respect to FIG. 8, an alternative preferred particular sequence for inserting screws 30, 40, 50 into the screw apertures 145, the secondary screw apertures, 250, the tertiary screw apertures 406, and the securing port 270 would be as follows: (1) 145k; (2) 400a; (3) 145j; (4) 145i; (5) 145d; (6) 145a; and (7) 270a (and/or 270b).

Once the surgeon has inserted a desired number of screws 30, 40, and 50 (which may be some number less than all of screws 30, 40, and 50) or at some intermediate point during the insertion of screws 30, 40 and 50, a fastener 271 can be placed within the at least one securing port 270 and into the second bone portion 35. An exemplary method for insertion of fastener 271 follows but the example should not be considered as limiting as to the order or sequence of steps. As an example, when (a) the first bone plate 100 is positioned adjacent to, in contact with, or along the first bone portion 20 of the patient with at least one screw 30 disposed through at least one of the screw apertures 145, and (b) the second bone plate 200 is positioned adjacent to, in contact with, or along the second bone portion 35 of the patient with at least one screw 40 disposed through at least one of the secondary screw apertures 250, a fastener 271 can be disposed through the bore 290 of the at least one securing port 270 and into at least a portion of the second bone portion 35. When the fastener 271 is disposed through the bore 290 and into at least a portion of the second bone portion 35, the head 274 of the fastener 271 engages the fastener head support surface 300 and applies a first force vector 700 (FIG. 2) generally along the fastener central axis 276 to the second bone plate 200. In this manner, the first force vector 700 draws the second bone plate 200 further against the second bone portion 35 of the patient (and/or draws the first bone plate 100 against or further against the first bone portion 20, and/or compresses fragments of the first or second bone portions 20, 35 together) thereby further reducing the second bone portion 35—in particular, the quadrilateral surface C—in a substantially fixed and surgically treated configuration.

The fastener 271 is generally disposed through the bore 290 of the at least one securing port 270 along the bore central axis 292 and into at least a portion of the second bone portion 35. As the at least one securing port 270 has a variety of angles of approach for fastener 271 to enter and pass through the bore 290 and into at least a portion of the second bone portion 35 (i.e., between fastener insertion vectors 294, 296), the surgeon can select an angle of approach to the second bone portion 35 for placing the fastener 271 through the at least one securing port 270 and into the second bone portion 35 that is appropriate for the patient's anatomy (e.g., that best matches the access to the surgical site offered by the approach chosen by the surgeon), best reduces the fracture F of the patient, achieves the greatest purchase of bone across the length of the fastener 271, and/or is a best compromise factoring all of the above-noted considerations.

For example, the surgeon can select an angle of approach of the fastener 271 through the bore 290 of the at least one securing port 270 to the second bone portion 35 between fastener insertion vectors 294, 296 that allows the fastener 271 to bridge two sides of a fracture line (such as fracture F) and thereby reduce the fracture by pulling portions of the bone adjacent the fracture toward one another.

Additionally, the angle of approach of the fastener 271 through the bore 290 of the at least one securing port 270 can also be selected by the surgeon to gain as much purchase through the second bone portion 35 as possible and thereby provide additional stability and post-operative strength to the bone plating system 10 as shown in FIGS. 4 and 5E. Additionally, the fastener 271 can be of any size, shape, and material suitable for use in further attaching the second bone plate 200 to the second bone portion 35 and, in some cases, further reducing the fracture F within the acetabulum E of the pelvis A of the patient 15. Further, although the fastener 271 is generally disclosed as being inserted through the bore 290 of the at least one securing port 270 after screws 30, 40, 50 have been inserted into the first bone portion 20 and the second bone portion 35, respectively, the surgeon can decide to insert the fastener 271 through the bore 290 of the at least one securing port 270 at any point in time of the surgical procedure—i.e., before, after, or during the insertion of any of the screws 30, 40, and 50. It is also contemplated that the surgeon may elect to forego inserting the fastener 271 altogether and/or elect to insert the fastener 271 before or after any of the insertion of screws 30, 40, and/or 50.

While the invention(s) of the present disclosure has been illustrated and described in detail in the drawings and foregoing description, such illustration and description are to be considered illustrative or exemplary and not restrictive and it is not intended to limit the invention(s) of the present disclosure to the disclosed embodiments. The mere fact that certain measures are recited in mutually different dependent claims does not indicate that a combination of these measures cannot be used advantageously.

What I claim is:

1. A bone plating system for a patient, comprising:
    a first bone plate sized and shaped to conform to a first bone portion of a patient;
    a second bone plate sized and shaped to conform to a second bone portion of the patient, wherein the second bone plate includes at least one securing port for receiving a fastener at an angle less than about 90 degrees with respect to a surface of the second bone plate,
        wherein the at least one securing port further comprises a bore extending from a second tissue engaging surface of the second bone plate to a second bone engaging surface of the second bone plate where the bore further comprises a bore central axis extending through a center of the bore in a direction substantially oriented toward a distal end of the second bone plate and away from a proximal end of the second bone plate, and
        wherein the at least one securing port further comprises a wall surrounding the bore, wherein the wall defines (i) a fastener support surface defining a head receiving volume adjacent the second tissue engaging surface, and (ii) a shaft clearance surface defining a generally frustoconical shaped shaft receiving volume, whereby the head receiving volume is generally spherically shaped and the shaft clearance surface is generally ellipse shaped; and
    at least one connecting bridge member configured to attach the first bone plate to the second bone plate.

2. The bone plating system of claim 1, wherein the second bone plate is generally trapezoid shaped and further includes a first side, and a second side wherein the distal end and proximal end are generally parallel to one another, and the first side and the second side generally diverge from one another.

3. The bone plating system of claim 2, wherein the second bone plate further comprises a plurality of secondary screw apertures.

4. The bone plating system of claim 3, wherein the plurality of secondary screw apertures further include a screw head support surface and a screw shaft clearance surface, with the screw head support surface defining a screw head receiving volume and the screw shaft clearance surface defining a screw shaft receiving volume.

5. The bone plating system of claim 2, wherein the second bone plate is defined by a plurality of internal struts defining a plurality of through-holes extending from the second bone engaging surface to the second tissue engaging surface of the second bone plate.

6. The bone plating system of claim 1, wherein the second bone plate further includes at least one reduction engaging aperture for receiving a surgical instrument capable of applying a force to the second bone plate.

7. The bone plating system of claim 1, wherein the fastener support surface is adjacent and abuts the shaft clearance surface at a bore vertex extending generally the entire circumference of the bore.

8. The bone plating system of claim 7, wherein the at least one securing port further comprises a fastener support axis generally adjacent the bore vertex, wherein the fastener support axis extends at a first angle that is less than or equal to 90 degrees relative to a bone engaging axis of the second bone plate.

9. The bone plating system of claim 8, wherein the first angle is from about 1 to about 90 degrees.

10. A bone plating system for a patient, comprising:
   a substantially rectangular shaped first bone plate sized and shaped to conform to a first bone portion of the patient, the first bone plate having a first bone engaging surface, a first tissue engaging surface, a first edge, and a second edge;
   a substantially trapezoidal shaped second bone plate sized and shaped to conform to a second bone portion of the patient, the second bone plate having a second bone engaging surface, a second tissue engaging surface, proximal end, a distal end, and an outer peripheral edge; and
   at least one connecting bridge member having a first end and a second end, wherein the first end of the at least one connecting bridge member is connected to the second edge of the first bone plate and the second end of the at least one connecting bridge member is connected to the proximal end of the second bone plate, wherein
      the proximal end of the second bone plate is spaced a first distance away from the second edge of the first bone plate, and the distal end of the second bone plate is spaced a second distance away from the second edge of the first bone plate with the second distance being larger than the first distance,
      the second bone engaging surface of the second bone plate has a hone engaging axis extending from the proximal end of the second bone plate to the distal end of the second bone plate, the bone engaging axis being a straight line fit to a series of data points representing the second bone engaging surface of the second bone plate,
      the second bone plate having at least one securing port for receiving a fastener, the at least one securing port having a bore extending from the second tissue engaging surface to the second bone engaging surface in a direction substantially oriented toward the outer peripheral edge and away from an interior portion of the second bone plate,
         the at least one securing port having a wall surrounding the bore, the wall having a fastener support surface defining a head receiving volume of the bore adjacent to the second tissue engaging surface, and a shaft clearance surface defining a substantially frustoconical shaped shaft receiving volume of the bore adjacent to the second bone engaging surface,
         the fastener support surface being adjacent to the shaft clearance surface such that the fastener support surface and the shaft clearance surface have a common vertex extending around at least a portion of the bore, the fastener support surface having a fastener support axis adjacent to the common vertex, the fastener support axis extending at an angle less than or equal to 90 degrees relative to the bone engaging axis,
   further wherein when the first bone plate is positioned on the first bone portion, the second bone plate is positioned on the second bone portion, and a shaft of a fastener is disposed through the bore and into the second bone portion, a head of the fastener engages the fastener support surface and applies a first force vector to the second bone plate thereby drawing the second bone engaging surface against the second bone portion of the patient's bone.

11. A method of implanting a bone plating system into a patient, comprising the step of surgically accessing a pelvic cavity of the patient and implanting a bone plating system in the patient, wherein the bone plating system further comprises
   a substantially rectangular shaped first bone plate sized and shaped to conform to a first bone portion of the patient, the first bone plate having a first bone engaging surface, a first tissue engaging surface, a first edge, and a second edge;
   a substantially trapezoidal shaped second bone plate sized and shaped to conform to a second bone portion of the patient, the second bone plate having a second bone engaging surface, a second tissue engaging surface, a proximal end, a distal end, and an outer peripheral edge; and
   at least one connecting bridge member having a first end and a second end, wherein the first end of the at least one connecting bridge member is connected to the second edge of the first bone plate and the second end of the at least one connecting bridge member is connected to the proximal end of the second bone plate, wherein
      the proximal end of the second bone plate is spaced a first distance away from the second edge of the first bone plate, and the distal end of the second bone plate is spaced a second distance away from the second edge of the first bone plate, with the second distance being larger than the first distance,
      the second bone engaging surface of the second bone plate has a bone engaging axis extending from the proximal end of the second bone plate to the distal end of the second bone plate, the bone engaging axis being a straight line fit to a series of data points representing the second bone engaging surface of the second bone plate,
      the second bone plate having at least one securing port for receiving a fastener, the at least one securing port having a bore extending from the second tissue engaging surface to the second bone engaging surface in a direction substantially oriented toward the outer peripheral edge and away from an interior portion of the second bone plate,
         the at least one securing port having a wall surrounding the bore, the wall having a fastener support surface defining a head receiving volume of the bore adjacent to the second tissue engaging surface, and a shaft clearance surface defining a substantially frustoconical shaped shaft receiving volume of the bore adjacent to the second bone engaging surface,
         the fastener support surface being adjacent to the shaft clearance surface such that the fastener support surface and the shaft clearance surface have a common vertex extending around at least a portion of the bore, the fastener support surface having a fastener support axis adjacent to the common vertex, the fastener support axis extending at an angle less than or equal to 90 degrees relative to the bone engaging axis, further wherein when the first bone plate is positioned on the first bone portion, the second bone plate is positioned on the second bone portion, and a shaft of a fastener is disposed through the bore and into the second bone portion, a head of the fastener engages the fastener support surface and applies a first force vector to the second bone plate thereby drawing the second bone engaging surface against the second bone portion of the patient's bone.

* * * * *